(12) United States Patent
Waxman et al.

(10) Patent No.: US 10,921,243 B2
(45) Date of Patent: *Feb. 16, 2021

(54) SYSTEMS AND METHODS FOR MULTISPECTRAL IMAGING AND GAS DETECTION USING A SCANNING ILLUMINATOR AND OPTICAL SENSOR

(71) Applicant: MultiSensor Scientific, Inc., Cambridge, MA (US)

(72) Inventors: Allen M. Waxman, Newton, MA (US); Terrence K. Jones, Sharon, MA (US); Jason M. Bylsma, Boston, MA (US); Stefan Bokaemper, Newton, MA (US)

(73) Assignee: MultiSensor Scientific, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/426,054

(22) Filed: May 30, 2019

(65) Prior Publication Data

US 2019/0277753 A1 Sep. 12, 2019

Related U.S. Application Data

(63) Continuation of application No. 16/129,731, filed on Sep. 12, 2018, now Pat. No. 10,371,627.
(Continued)

(51) Int. Cl.
*G01N 21/3504* (2014.01)
*G01N 33/22* (2006.01)
(Continued)

(52) U.S. Cl.
CPC ......... *G01N 21/3504* (2013.01); *G01F 1/661* (2013.01); *G01J 3/021* (2013.01);
(Continued)

(58) Field of Classification Search
None
See application file for complete search history.

(56) References Cited

U.S. PATENT DOCUMENTS 3,517,190 A 6/1970 Astheimer
3,662,171 A 5/1972 Brengman et al.
(Continued)

FOREIGN PATENT DOCUMENTS

CN 101680833 A 3/2010
CN 103503135 A 1/2014
(Continued)

OTHER PUBLICATIONS

Benson, R. et al., Standoff passive optical leak detection of volatile organic compounds using a cooled InSb based infrared imager, Proceedings of the Air & Waste Management Assoc. Conf. Extended Abstract No. 06-A-131-AQMA, pp. 1-10 (2006).
(Continued)

*Primary Examiner* — Shawn Decenzo
(74) *Attorney, Agent, or Firm* — Choate, Hall & Stewart LLP; William R. Haulbrook; Ronen Adato

(57) ABSTRACT

Presented herein are systems and methods directed to a multispectral absorption-based imaging approach that provides for rapid and accurate detection, localization, and quantification of gas leaks. The imaging technology described herein utilizes a scanning optical sensor in combination with structured and scannable illumination to detect and image spectral signatures produced by absorption of light by leaking gas in a quantitative manner over wide areas, at distance, and in the presence of background such as ambient gas and vapor. Moreover, the specifically structured and scannable illumination source of the systems and methods described herein provides a consistent source of illumination for the scanning optical sensor, allowing imaging to be performed even in the absence of sufficient natural light,
(Continued)

such as sunlight. The imaging approaches described herein can, accordingly, be used for a variety of gas leak detection, emissions monitoring, and safety applications.

22 Claims, 35 Drawing Sheets
(26 of 35 Drawing Sheet(s) Filed in Color)

Related U.S. Application Data

(60) Provisional application No. 62/587,304, filed on Nov. 16, 2017.

(51) Int. Cl.

| | |
|---|---|
| *G01F 1/66* | (2006.01) |
| *G01J 3/02* | (2006.01) |
| *G01J 3/06* | (2006.01) |
| *G01J 3/10* | (2006.01) |
| *G01J 3/28* | (2006.01) |
| *G01J 3/42* | (2006.01) |
| *G01M 3/20* | (2006.01) |
| *G01M 3/38* | (2006.01) |
| *G01N 33/00* | (2006.01) |
| *G01N 21/359* | (2014.01) |
| *E21B 41/00* | (2006.01) |
| *G01J 3/12* | (2006.01) |
| *G01N 21/17* | (2006.01) |

(52) U.S. Cl.
CPC ............... *G01J 3/0208* (2013.01); *G01J 3/06* (2013.01); *G01J 3/10* (2013.01); *G01J 3/2803* (2013.01); *G01J 3/2823* (2013.01); *G01J 3/42* (2013.01); *G01M 3/20* (2013.01); *G01M 3/38* (2013.01); *G01N 33/0036* (2013.01); *G01N 33/225* (2013.01); *E21B 41/0021* (2013.01); *G01J 2003/1213* (2013.01); *G01J 2003/1221* (2013.01); *G01J 2003/2806* (2013.01); *G01J 2003/2826* (2013.01); *G01N 21/359* (2013.01); *G01N 2021/1795* (2013.01); *G01N 2021/3513* (2013.01); *G01N 2201/101* (2013.01)

(56) References Cited

U.S. PATENT DOCUMENTS

| | | | |
|---|---|---|---|
| 4,264,209 A | 4/1981 | Brewster | |
| 4,490,613 A | 12/1984 | Brame | |
| 4,543,481 A | 9/1985 | Zwick | |
| 4,555,627 A | 11/1985 | McRae, Jr. | |
| 4,864,127 A | 9/1989 | Brame | |
| 4,999,498 A | 3/1991 | Hunt et al. | |
| 5,103,675 A | 4/1992 | Komninos | |
| 5,281,816 A | 1/1994 | Jacobson et al. | |
| 5,306,913 A | 4/1994 | Noack et al. | |
| 5,656,813 A | 8/1997 | Moore et al. | |
| 6,061,141 A | 5/2000 | Goldenberg et al. | |
| 6,680,778 B2 | 1/2004 | Hinnrichs et al. | |
| 6,690,472 B2 | 2/2004 | Kulp et al. | |
| 7,075,653 B1 | 7/2006 | Rutherford | |
| 7,486,399 B1* | 2/2009 | Reichardt | G01M 3/20 |
| | | | 250/330 |
| 7,649,174 B2 | 1/2010 | Mammen et al. | |
| 7,977,639 B2 | 7/2011 | Maillart et al. | |
| 8,193,496 B2 | 6/2012 | Furry | |
| 8,426,813 B2 | 4/2013 | Furry | |
| 8,730,477 B2* | 5/2014 | Ruhland | G01S 7/4813 |
| | | | 356/4.01 |
| 9,228,938 B2* | 1/2016 | Hager | G01N 21/3504 |
| 9,955,910 B2* | 5/2018 | Fright | A61B 5/1077 |
| 10,031,040 B1* | 7/2018 | Smith | G01N 21/00 |
| 10,190,976 B2 | 1/2019 | Waxman et al. | |
| 10,197,470 B2 | 2/2019 | Waxman et al. | |
| 10,330,593 B1 | 6/2019 | Dobler et al. | |
| 10,371,627 B2* | 8/2019 | Waxman | G01J 3/06 |
| 10,436,710 B2 | 10/2019 | Waxman et al. | |
| 2002/0071122 A1* | 6/2002 | Kulp | G01N 21/53 |
| | | | 356/437 |
| 2006/0202122 A1 | 9/2006 | Gunn et al. | |
| 2006/0203248 A1 | 9/2006 | Reichardt et al. | |
| 2010/0127173 A1 | 5/2010 | Schmidt | |
| 2010/0231722 A1 | 9/2010 | Hill, Jr. et al. | |
| 2010/0241361 A1 | 9/2010 | Hofvander et al. | |
| 2012/0062697 A1* | 3/2012 | Treado | H04N 5/332 |
| | | | 348/42 |
| 2012/0062740 A1* | 3/2012 | Treado | G01J 3/0264 |
| | | | 348/144 |
| 2013/0327942 A1 | 12/2013 | Silny | |
| 2014/0002667 A1 | 1/2014 | Cheben et al. | |
| 2014/0008526 A1 | 1/2014 | Zeng et al. | |
| 2014/0104607 A1* | 4/2014 | Treado | G01J 3/0264 |
| | | | 356/301 |
| 2014/0118722 A1* | 5/2014 | Treado | G01J 3/02 |
| | | | 356/51 |
| 2014/0160479 A1 | 6/2014 | Hager et al. | |
| 2014/0268104 A1* | 9/2014 | Treado | G02B 21/361 |
| | | | 356/51 |
| 2015/0069239 A1 | 3/2015 | Kester et al. | |
| 2015/0316473 A1 | 11/2015 | Kester et al. | |
| 2015/0323449 A1 | 11/2015 | Jones et al. | |
| 2016/0069743 A1 | 3/2016 | McQuilkin et al. | |
| 2016/0131576 A1 | 5/2016 | Cabib et al. | |
| 2016/0334538 A1 | 11/2016 | Rieker et al. | |
| 2016/0345835 A1 | 12/2016 | Darty | |
| 2016/0349228 A1 | 12/2016 | Kester et al. | |
| 2017/0234761 A1 | 8/2017 | Augusto | |
| 2017/0284891 A1 | 10/2017 | Miranda | |
| 2017/0336281 A1* | 11/2017 | Waxman | G01N 33/0036 |
| 2017/0336320 A1 | 11/2017 | Yalin | |
| 2018/0045596 A1 | 2/2018 | Prasad et al. | |
| 2018/0266944 A1 | 9/2018 | Waxman et al. | |
| 2019/0137390 A1 | 5/2019 | Waxman et al. | |
| 2019/0145891 A1 | 5/2019 | Waxman et al. | |
| 2019/0170900 A1 | 6/2019 | Rieker et al. | |
| 2020/0240906 A1 | 7/2020 | Waxman et al. | |

FOREIGN PATENT DOCUMENTS

| | | |
|---|---|---|
| WO | WO-02/27297 A1 | 4/2002 |
| WO | WO-2017/201194 A1 | 11/2017 |
| WO | WO-2019/099096 A1 | 5/2019 |
| WO | WO-2020/154619 A2 | 7/2020 |

OTHER PUBLICATIONS

Buchwitz, M. et al., Atmosphere methane and carbon dioxide from SCIAMACHY satellite data, Atmos. Chem. Phys., 5:941-962 (2005).
Byer, R. L. and Shepp, L. A., Two-dimensional remote air-pollution monitoring via tomography, Optics Letters, 4(3):75-77 (1979).
Clark, R. N. et al., Reflectance spectroscopy of organic compounds: Alkanes, J. Geophysical Research. 114:E030001:1-19, (2009).
Epperson, D. et al., Equivalent Leak Definitions for Smart LDAR (Leak Detection and Repair) When Using Optical Imaging Technology, Journal of the Air & Waste Management Association. 57(9):1050-1060, (2007).
Furry, D. et al., Detection of Volatile Organic Compounds (VOC's) with a Spectrally Filtered Cooled Mid-Wave Infrared Camera, Information Proceedings, Document No. ITC 108A Jun. 1, 2005, 6 pages, (2005).
Gottwald, M. et al., The Instrument, Chapter 3 in SCHIAMACHY—Exploring the Changing Earth's Atmosphere, pp. 29-46, (2006).
Gross, W. et al., Localization of Methane Distributions by Spectrally Tuned Infrared Imaging, SPIE, Part of the SPIE Conference on Air Monitoring and Detection of Chemical and Biological Agents, 3533:234-240, (1998).
Inada, H. et al., Uncooled SWIR InGaAs/GaAsSb type II quantum wells focal plane array, Proc. of SPIE, Infrared Technology and Applications XXXVI. 7660:76603N-1-76603N-7 (2010).

(56) References Cited

OTHER PUBLICATIONS

International Search Report and Written Opinion, International Application No. PCT/US2017/033157 (Hydrocarbon Leak Imaging and Quantification Sensor, filed May 17, 2017), issued by ISA/US, Commissioner for Patents, 12 pages, dated Sep. 14, 2017.
International Search Report, International Application No. PCT/US18/22943 (Scanning IR Sensor for Gas Safety and Emissions Monitoring, filed Mar. 16, 2018), issued by ISA/US, Commissioner for Patents, 4 pages, dated Aug. 8, 2018.
International Search Report, International Application No. PCT/US2018/050760 (Systems and Methods for Multispectral Imaging and Gas Detection Using a Scanning Illuminator and Optical Sensor, filed Sep. 12, 2018), issued by ISA/European Patent Office, 7 pages, dated Mar. 8, 2019.
Shulz, M. et al., High-resolution thermophysical measurements using staring infrared detector arrays, High Temperatures—High Pressures, 32:547-556 (2000).
Van Den Bosch. C. J. H. and Duijm, N. J., Overflow and Spray release, Chapter 2, Methods for Calculation of Physical Effects: Due to Release of Hazardous Materials (Liquids & Gases)., EDS: Van den Bosch et al., 3rd Ed. 2nd Printing, CPR 14E, TNO—The Netherlands Organization of Applied Scientific Research, pp. 2.1-2.179 (2005).
Written Opinion, International Application No. PCT/US18/22943 (Scanning IR Sensor for Gas Safety and Emissions Monitoring, filed Mar. 16, 2018), issued by ISA/US, Commissioner for Patents, 9 pages, dated Aug. 8, 2018.
Written Opinion, International Application No. PCT/US2018/050760 (Systems and Methods for Multispectral Imaging and Gas Detection Using a Scanning Illuminator and Optical Sensor, filed Sep. 12, 2018), issued by ISA/European Patent Office, 12 pages, dated Mar. 8, 2019.

\* cited by examiner

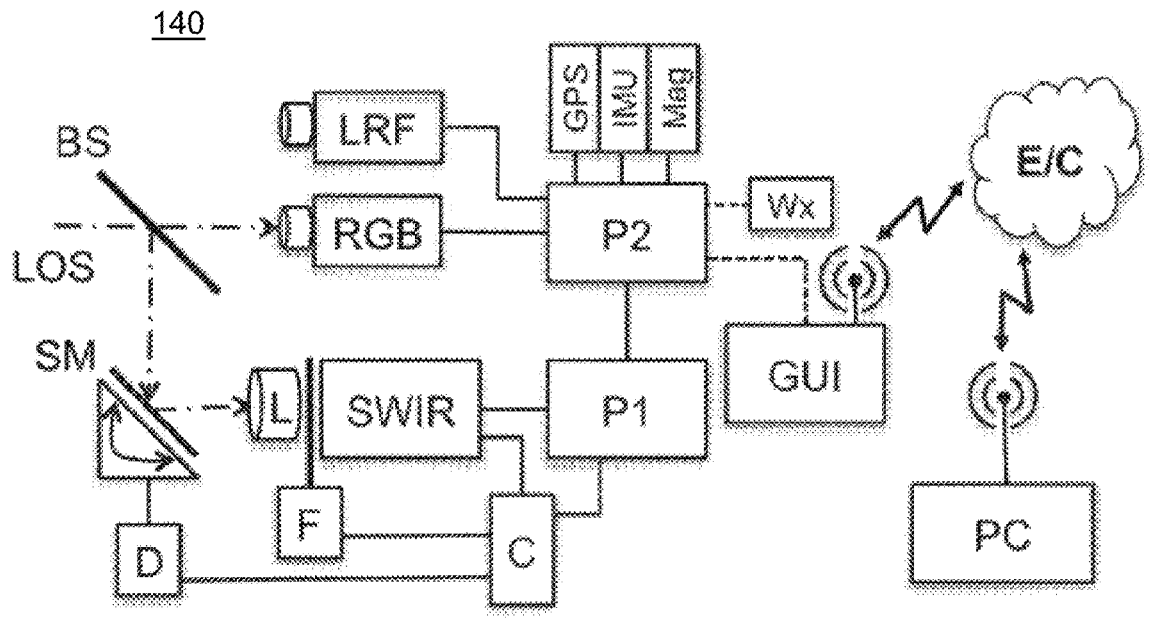

FIG. 1C

| | |
|---|---|
| SWIR – | SWIR photo-detector array with read-out imaging electronics |
| L – | Lens for SWIR photo-detector array (located in front of filters) |
| RGB – | Color visible micro-camera with lens |
| LRF – | Laser Range Finder |
| LOS – | Line of sight from coincident optical axes of imagers |
| BS – | Beam Splitter (dichroic) |
| SM – | Scanning mirror |
| D – | Driver electronics for scanning mirror |
| F – | Filter changer (as required for moving filter holder) |
| C – | micro-Controller for synchronization signals |
| P1 – | micro-Processor #1 (real-time SWIR processor) |
| P2 – | micro-Processor #2 (all other sensors & GUI requests) |
| GPS – | Global Positioning System receiver |
| IMU – | Inertial Measurement Unit (6 degrees-of-freedom) |
| Mag – | Magnetometer compass |
| Wx – | Weather sensors (T, P, RH, wind speed & direction) |
| GUI – | Graphical User Interface on touchscreen tablet |
| E/C – | Ethernet / Cloud |
| PC – | Personal Computer remotely running system via cloud |

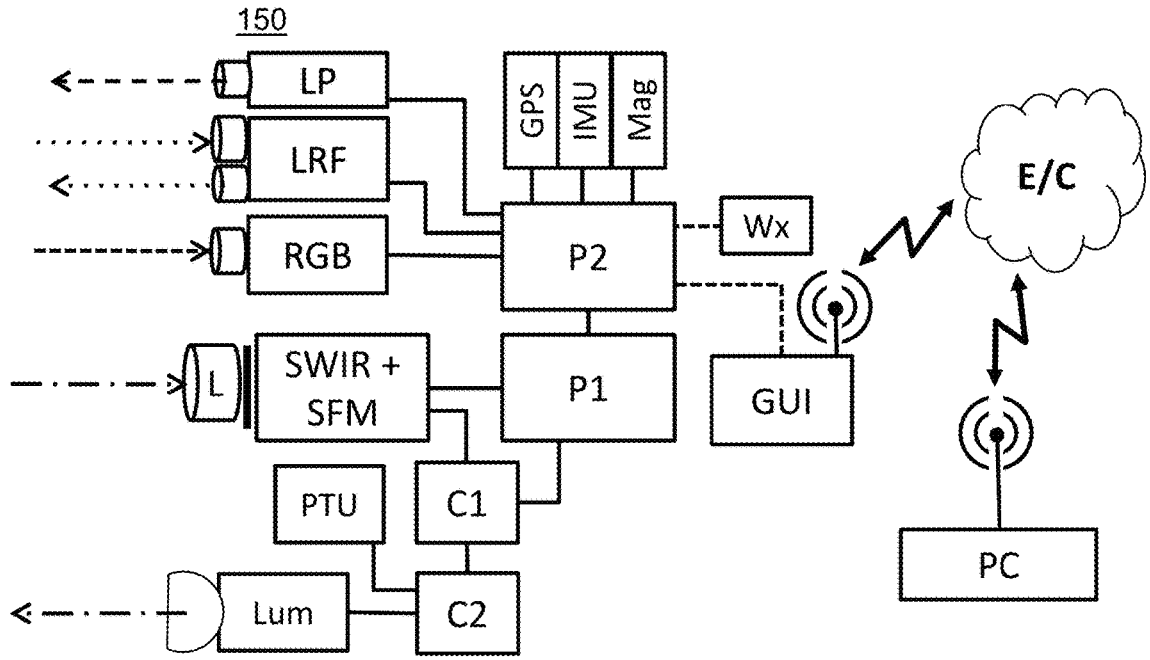

FIG. 1D

| | |
|---|---|
| SWIR – | SWIR photo-detector array with read-out electronics |
| SFM – | Spectral Filter Matrix located over SWIR detector array |
| L – | Lens for SWIR photo-detector array (located in front of SFM) |
| RGB – | Color visible micro-camera with lens |
| LRF – | Laser Range Finder (near-IR) |
| LP – | Laser Pointer (visible "red dot") |
| PTU – | Pan-Tilt Unit scans sensors across site in two-dimensions |
| Lum – | SWIR broadband Illuminator to augment solar illumination |
| C1 – | micro-Controller with A/D converter samples SWIR signals |
| C2 – | micro-Controller controls PTU motion and illuminator brightness |
| P1 – | micro-Processor #1 (real-time SWIR signal processor) |
| P2 – | micro-Processor #2 (all other sensors & GUI requests/display) |
| GPS – | Global Positioning System receiver |
| IMU – | Inertial Measurement Unit (6 degrees-of-freedom) |
| Mag – | Magnetometer compass |
| Wx – | Weather sensors (T, P, RH, wind speed & direction) |
| GUI – | Graphical User Interface on touchscreen tablet |
| E/C – | Ethernet / Cloud |
| PC – | Personal Computer remotely running system via cloud |

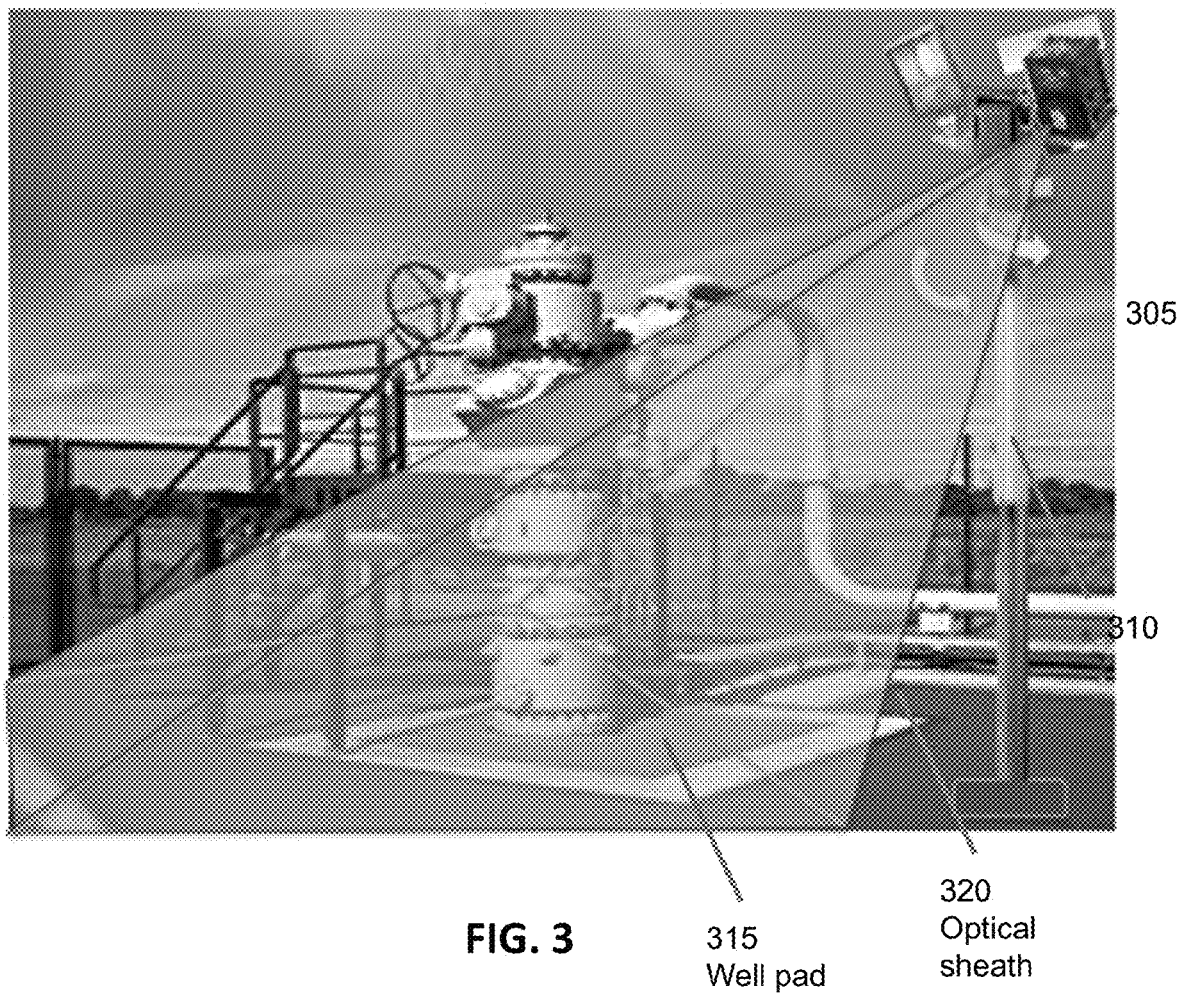
FIG. 3    315 Well pad    320 Optical sheath

400

420

1300

1350

5-Element Array of Discrete Photo-Detectors
With a 5-Band Spectral Filter Overlay 9-Element Array of Macro-Pixel Photodiodes
Covered by a 9-Band Spectral Filter Mosaic Methane Jet from a 1mm Orifice at 1300psi Profiles of Differential Optical Depth
Along the Axis of a Methane Jet

SYSTEMS AND METHODS FOR MULTISPECTRAL IMAGING AND GAS DETECTION USING A SCANNING ILLUMINATOR AND OPTICAL SENSOR

CROSS-REFERENCE TO RELATED APPLICATIONS

This application is a continuation of U.S. Non-Provisional patent application Ser. No. 16/129,731, filed Sep. 12, 2018 (now U.S. Pat. No. 10,371,627, issued Aug. 6, 2019), which claims priority to and benefit of U.S. Provisional Patent Application No. 62/587,304, filed Nov. 16, 2017, the content of each of which is hereby incorporated by reference herein in its entirety.

FIELD OF THE INVENTION

This invention relates generally to methods, systems, and architectures for multispectral imaging. In particular, in certain embodiments, this invention relates to systems and methods for obtaining a multispectral absorption image of a scene using a structured illumination beam that is scanned in a synchronized fashion with an instantaneous field of view (ifov) of an optical sensor.

BACKGROUND OF THE INVENTION

Natural gas leaks create both safety and environmental hazards, and occur along the entire gas supply chain from the well to the street (so-called upstream, midstream, and downstream sectors). Methane, the primary constituent of natural gas is combustible in air, and is also a potent greenhouse gas. Other hydrocarbons found in natural gas, as well vapors emanating from liquids separated from gas and oil include ethane, propane, butane, pentane, hexane, octane, and heavier hydrocarbons, which form volatile organic compounds that generate smog which is a health hazard. Thus, there are compelling reasons to detect leaks of gases comprising, for example, methane and other hydrocarbons, so that such leaks can be repaired.

Beyond merely detecting presence of leaking gas, localizing leaks and quantifying their leak rate (e.g., emission flux of leaking gas) are important for allowing repair of leaks to be performed rapidly, and in a prioritized fashion. Quantification of leak rate also allows the impact (e.g., environmental impact) of leaking gas to be assessed. Detection, localization, and quantification of gas leaks is challenging, since leak monitoring and/or inspection typically need to be performed over wide areas, and from a safe and practical standoff distance The presence of naturally occurring ambient gases and vapors, such as water vapor, also poses challenges, since leaking gas of specific compounds of interest needs to be distinguished from such ambient gases.

Accordingly, there exists a need for improved systems and methods for detection, localization, and quantification of gas leaks. In particular, there is a need for systems and methods that allow for effective gas leak monitoring and/or inspection to be performed over wide areas, and even in the presence of interfering background signals. Cost effective solutions are particularly important, as they can be broadly adopted and utilized.

SUMMARY OF THE INVENTION

Presented herein are systems and methods directed to a multispectral absorption-based imaging approach that provides for rapid and accurate detection, localization, and quantification of gas leaks. The imaging technology described herein utilizes a scanning optical sensor in combination with structured and scannable illumination to detect and image spectral signatures produced by absorption of light by leaking gas in a quantitative manner over wide areas, at distance, and in the presence of background such as ambient gas and vapor. Moreover, the specifically structured and scannable illumination source of the systems and methods described herein provides a consistent source of illumination for the scanning optical sensor, allowing imaging to be performed even in the absence of sufficient natural light, such as sunlight. The imaging approaches described herein can, accordingly, be used for a variety of gas leak detection, emissions monitoring, and safety applications.

In particular, in certain embodiments, the systems and methods described herein utilize a structured illumination beam to provide a source of illumination for a scanning optical sensor. The scanning optical sensor detects light from a scene to be imaged, such as a site to be monitored, which is reflected by objects on a target surface within the scene (e.g., ground), and captured within an instantaneous field of view (ifov) of the optical sensor. As light travels to the sensor, it may be absorbed by intervening gas. e.g., produced by a leak present in the scene. Absorption of light by gas produces spectral signatures that are indicative of and specific to various compounds (e.g., hydrocarbons) that are present in the gas. Accordingly, by detecting light absorption in a spectrally sensitive manner, e.g., using various spectral filters placed in front of one or more detectors, different gases and compounds present therein can be detected and identified. By scanning (e.g., raster scanning) the ifov of the optical sensor across the scene, and detecting absorption of light in a spectrally sensitive manner at multiple locations, multispectral absorption images of the scene can be created. Such images can be used to map concentrations of various compounds of interest across the scene, and analyzed to detect, localize, and quantify gas leaks.

In certain embodiments, the illumination beam is structured to provide a substantially uniform illumination spot that covers a portion of the target surface, such that light from the illumination spot is reflected back, towards the optical sensor, for detection. The illumination beam is structured to produce an illumination spot that has a long dimension (e.g., a length) that is substantially larger than the projection of ifov of the optical sensor onto the target surface. For example, the illumination spot may be a narrow, approximately rectangular stripe or ellipsoidal in shape. The ifov of the optical sensor can then be scanned, rapidly, along the length of the illumination spot (the fast axis), while both the ifov of the optical sensor and the illumination spot are scanned, together, at a slower rate in an approximately orthogonal direction (the slow axis). This allows the ifov of the optical sensor to be raster scanned across the scene, to form a multispectral absorption image.

Scanning of the illumination spot with the ifov of the sensor so as to maintain overlap between the two can be accomplished by using separate, synchronized scanners for slow scanning of the illumination spot and ifov. A single scanner, such as a rotational stage, on which both the illumination source and optical sensor along with its scanner (responsible for scanning along the fast axis) are mounted and maintained in fixed alignment, may also be used to maintain overlap and scan the illumination spot with the ifov along the slow axis.

In this manner, consistent illumination can be provided, and imaging performed even in the absence of sufficient natural light. Notably, the approach of using a structured and scannable illumination source to provide artificial illumination is significantly more cost effective, energy efficient, and practical than illuminating an entire site (e.g., at the same time), and accordingly allows large areas to be monitored. This approach also allows for portable, battery powered systems, such as a handcart-mounted system, and generator powered truck or airborne vehicle mounted systems that include both the illuminator and optical sensor, and fixed-site installed and relocatable systems.

Imaging systems designed in accordance with the approaches described herein can, accordingly, be used for gas emission monitoring of various sites of interest. For example, mobile truck-mounted or fixed mast-mounted systems can image obliquely down and outwards over various sites of interest, such as well pads, compressors, or regions of ground above buried pipelines to detect gas leaks therefrom. Portable and relocatable systems can be moved from site to site. The approaches described herein can thus be used for detecting, localizing, and quantifying leaks from components along the entire gas supply chain, from well head to compressors, transmission pipelines, gate stations, and underground distribution networks. Similar approaches may also be used for detection of liquid oil spills on land, sand, seawater, and sea ice, as well as detecting oil emulsions at sea and tar balls contamination on beaches.

In certain embodiments, the imaging technologies described herein operate in the short-wave infrared (SWIR) spectral range (e.g., ranging from approximately 1.0 to 2.5 microns). Spectral absorption signatures in the SWIR region are particularly useful for detection of compounds including, but not limited to, hydrocarbons such as methane, ethane, propane, butane, as well as other gases such as carbon dioxide and ammonia. Use of SWIR light is unconventional, and offers several advantages over other conventional infrared spectral ranges.

In particular, while detection in other infrared spectral ranges often relies on a temperature difference between leaked gas and background, spectrally sensitive absorption imaging in the SWIR region does not, and accordingly allows for gas leaks to be detected even if the leaked gas is at a similar temperature to the background. Interference from ambient gas, such as water vapor is also less significant in the SWIR region than in other spectral regions, such as the mid- and long-wave infrared. This allows for imaging to be performed in humid air, steam, and fog, which would otherwise dramatically degrade performance of or prohibit use of imaging in other infrared spectral ranges. Use of SWIR light also reduces cost of and simplifies system components, particularly detectors. Unlike detectors operating at longer infrared wavelengths, detectors responsive to SWIR light typically do not require cryogenic cooling (e.g., Stirling engines, liquid nitrogen). Instead, detectors used in the systems and methods described herein may be used with less expensive and more reliable thermo-electric cooling approaches.

Use of the scanning illuminator and optical sensor techniques described herein with SWIR light based imaging thus provides a particularly advantageous approach. Other wavelength ranges, such as the visible spectral range (e.g., ranging from about 400 to 700 nanometers) may also be used. Visible imaging is particularly relevant to detection of leaking hydrogen. By illuminating and imaging in the visible spectrum, one can exploit the electronic transitions of molecular hydrogen to detect a leak. In the case of projecting visible illumination, it may be preferred to use a shuttering source so that ambient visible light may be subtracted from the combined ambient plus artificial illumination.

Accordingly, by providing imaging technologies capable of performing rapid and effective multi-spectral absorption-based imaging over wide areas, at distance, and which are compatible with portable implementations, the systems and methods described herein overcome a number of challenges associated with previous systems and methods for detecting gas leaks and facilitate a variety of gas leak, emissions, and safety monitoring applications.

In one aspect, the invention is directed to a system for obtaining a multispectral absorption image of a scene using a structured illumination beam that is scanned in a synchronized fashion with an instantaneous field of view (ifov) of an optical sensor, the system comprising: (a) an illumination source aligned and operable to produce the structured illumination beam and direct the structured illumination beam towards a target surface [e.g., an approximately vertical wall (e.g., upon which structures such as gas plumbing, meters, valves, etc. are mounted); e.g., an approximately horizontal surface (e.g., such as ground of a site to be imaged; e.g., a ceiling above a structure to be inspected, such as a compressor, a well, etc.)] within the scene, thereby illuminating an illumination spot corresponding to a projection of the structured illumination beam onto the target surface, the illumination spot having a length (e.g., a spot size measured along a long axis) and a width (e.g., a spot size measured along a short axis that is approximately orthogonal to the long axis), wherein the length is greater than or equal to the width (e.g., wherein the illumination spot is an approximately rectangular spot; e.g., wherein the illumination spot is an approximately ellipsoidal spot and its length corresponds to a major axis of the approximately ellipsoidal spot); (b) a beam scanner operable to scan the illumination spot in a beam scan direction that is substantially parallel to the width of the illumination spot (e.g., and across a distance greater than or approximately equal to the width of the illumination spot), (c) an optical sensor comprising one or more spectral detectors, each aligned and operable to detect light having wavelengths within a particular associated spectral band, wherein the optical sensor is aligned and operable to capture light from (e.g., emitted and/or reflected by objects within) the scene within a sensor instantaneous field of view (ifov) corresponding to a combined ifov of the one or more spectral detectors (e.g., each spectral detector having an individual ifov wherein light from the scene within a particular spectral detector's ifov is captured and directed onto the particular spectral detector, and wherein the sensor ifov corresponds to a combination of all the individual ifov s of the spectral detectors) and direct the captured light, for detection, onto the one or more spectral detectors, thereby detecting light from a particular sampled image location corresponding to a projection of the sensor ifov onto the target surface [e.g., the detected light having been attenuated (e.g., due to absorption) as it travels from the sampled image location to the optical sensor]; (d) an optical sensor scanner aligned and operable to scan the projection of the sensor ifov across the scene, so as to detect light from a plurality of sampled image locations within the scene, wherein the optical sensor scanner is synchronized with the beam scanner so as to maintain overlap between the projection of the sensor ifov and the illumination spot as both are scanned; (e) a processor of a computing device; and (f) a memory having instructions stored thereon, wherein the instructions, when executed by the processor, cause the processor to: retrieve and/or access data corresponding to the detected light from each of the sampled image locations;

and use the data to create a multispectral absorption image of the scene [e.g., wherein the multispectral absorption image comprises a plurality of image pixels, each (i) corresponding to a particular physical location within the scene (e.g., on the target surface) and (ii) having one or more intensity values each representing a level of absorption within a particular spectral band and determined using the data corresponding to the detected light from each of the sampled image locations].

In certain embodiments, the length of the illumination spot is a factor of approximately 10 or more greater than its width (e.g., a factor of approximately 20 or more greater than its width; e.g., a factor of approximately 50 or more greater than its width; e.g., a factor of approximately 100 or more greater than its width). In certain embodiments, the width of the illumination spot is greater than or approximately equal to a size of the projection of the sensor ifov measured along a same direction (e.g., no less than the size of the projection of the sensor ifov measured along the same direction; e.g., no less than 1.5 times the size of the projection of the sensor ifov measured along the same direction; e.g., no less than 2 times the size of the projection of the sensor ifov measured along the same direction).

In certain embodiments, the optical sensor scanner is aligned and operable to scan the projection of the sensor ifov along a first scan axis (e.g., a fast axis) aligned along the length of the illumination spot and along a second scan axis (e.g., a slow axis) aligned along the width of the illumination spot.

In certain embodiments, the optical sensor scanner is operable to scan the projection of the sensor ifov along the second scan axis in a step-wise fashion, and, for each of a plurality of steps in the step-wise scan along the second scan axis, scan the projection of the sensor ifov along the first scan axis [e.g., wherein the beam scanner is also operable to scan the illumination spot in a step-wise fashion; e.g., wherein the beam scanner is operable to scan the illumination spot in a continuous fashion at a beam scan rate (e.g., less than the rate at which the optical sensor scanner is operable to scan the projection of the sensor ifov along the first scan axis)].

In certain embodiments, the first scan axis is a fast axis along which the optical sensor scanner is operable to scan the projection of the sensor ifov at a fast scan rate (e.g., in a continuous fashion) and the second scan axis is a slow axis along which the optical sensor scanner is operable to scan the projection of the sensor ifov at a slow scan rate (e.g., in a continuous fashion)[e.g., wherein the beam scanner is also operable to scan the illumination spot in a step-wise fashion; e.g., wherein the beam scanner is operable to scan the illumination spot in a continuous fashion at a beam scan rate (e.g., less than the rate at which the optical sensor scanner is operable to scan the projection of the sensor ifov along the first scan axis) comparable to the slow scan rate].

In certain embodiments, the fast scan rate is sufficiently fast in comparison with the slow scan rate so as to allow for the projection of the sensor ifov to be scanned across a desired distance along the fast scan axis before it is moved an appreciable distance (e.g., before it is moved a distance corresponding to a size of an individual ifov of an individual spectral detector of the optical sensor) along the slow scan axis.

In certain embodiments, the fast scan rate is a factor of approximately 10 or more (e.g., a factor of approximately 20; e.g., a factor of approximately 50; e.g., a factor of approximately 100; e.g., a factor of approximately 1000) greater than the slow scan rate.

In certain embodiments, the fast scan rate is sufficiently fast so as to allow for the projection of the sensor ifov to be scanned through multiple (e.g., at least 10; e.g., at least 20; e.g., at least 50; e.g., at least 100; e.g., at least 1000) sampled image locations along the length of the illumination spot before the illumination spot moves the appreciable distance.

In certain embodiments, the target surface is a substantially horizontal surface (e.g., ground of a site to be imaged and on which various structures may be located) and the illumination source is positioned in an elevated position above the target surface (e.g., overlooking the site to be imaged) and aligned to direct the structured beam of illumination towards the target surface and outwards (e.g., obliquely), such that the length of the illumination spot is directed outwards from a location beneath the illumination source.

In certain embodiments, the target surface is a substantially horizontal surface (e.g., a ceiling above a structure to be inspected, such as a compressor, a well, etc.) and the illumination source is positioned below the target surface (e.g., looking upwards at the site to be imaged) and aligned to direct the structured beam of illumination towards the target surface and outwards (e.g., obliquely), such that the length of the illumination spot is directed outwards from a location above the illumination source.

In certain embodiments, the target surface is a substantially vertical surface [e.g., a wall upon which structures (e.g., gas plumbing, meters, valves, etc.) are mounted](e.g., at similar height to the optical sensor and/or illumination source).

In certain embodiments, the length of the illumination spot is greater than or equal to a first dimension of a target region within the target surface, the beam scanner is operable to scan the illumination spot in the beam scan direction across a distance greater than or equal to a second dimension of the target region, and the optical sensor scanner is operable to raster scan the projection of the sensor ifov across the target region (e.g., the optical sensor scanner is operable to scan the projection of the sensor ifov along a first scan axis directed along the length of the illumination spot and over a distance greater than or equal to the first dimension of the target region and operable to scan the projection of the sensor ifov along a second scan axis over a distance greater than or equal to the second dimension of the target region).

In certain embodiments, the beam scanner is repositionable so as to provide for scanning of the illumination spot over multiple target regions [e.g., thereby providing for imaging over a large-scale region having dimensions larger than (i) a length of the illumination spot and/or (ii) a distance over which the beam scanner is operable to scan; e.g., thereby providing for scanning over multiple target regions that are spaced apart from one another].

In certain embodiments, the optical sensor scanner is repositionable so as to provide for scanning of the sensor ifov over multiple target regions [e.g., thereby providing for imaging over a large-scale target region having dimensions larger than a distance over which the optical sensor scanner is operable to scan the sensor ifov].

In certain embodiments, the structured illumination beam is structured spatially to compensate for dilution of projected power with range [e.g., such that an intensity of the illumination spot is substantially uniform along its length; e.g., such that an intensity of the illumination spot is above a predetermined threshold level (e.g., sufficient for providing for imaging at or above a particular signal to noise ratio) across its length].

In certain embodiments, the illumination source comprises a plurality of emitters each of which outputs illumination light, wherein the illumination light output from the plurality of emitters is combined to produce the structured beam of illumination [e.g., wherein the plurality of emitters are arranged in a chain aligned with the length of the illumination spot and each emitter outputs illumination light at a different power level (e.g., the power level increasing along the chain, from one end of the chain to another)].

In certain embodiments, the structured beam of illumination comprises short wave infrared (SWIR) light (e.g., light having wavelengths ranging from approximately 1 to 2.6 microns), and the one or more spectral detectors are responsive to SWIR light [e.g., thereby providing for absorption based imaging using SWIR light, relevant for detection of hydrocarbon compounds].

In certain embodiments, the structured beam of illumination comprises visible light (e.g., light having wavelengths ranging from approximately 400 to 700 nanometers) and the one or more detectors are responsive to visible light [e.g., thereby providing for absorption based imaging using visible light, e.g., relevant for imaging based on electronic transitions of compounds of interest; e.g., relevant for hydrogen detection].

In certain embodiments, the multispectral absorption image comprises a plurality of image pixels, each (i) corresponding to a particular physical location within the scene (e.g., within a target region of the target surface) and (ii) having one or more intensity values each representing a level of absorption within a corresponding particular spectral band and determined using the data corresponding to the detected light from each of the sampled image locations.

In certain embodiments, for each of at least a portion of the intensity values, the corresponding particular spectral band comprises one or more absorption lines of a specific compound of interest [e.g., wherein the particular spectral band is an extended spectral band, spanning approximately 50 nanometers or more (e.g., spanning from 50 to 200 nanometers; e.g., spanning from 50 to 100 nanometers); e.g., spanning approximately 100 nanometers or more (e.g., spanning from 100 to 200 nanometers)].

In certain embodiments, the optical sensor comprises at least one spectral filter positioned in front of at least a portion of the one or more spectral detectors, wherein the at least one spectral filter is substantially transmissive to light having a wavelength within a specific spectral band of the corresponding particular spectral band(s) and substantially opaque to light having a wavelength outside of the specific spectral band.

In certain embodiments, the instructions cause the processor to calibrate the data to account for spectral content of the illumination source (e.g., differences in amount of light at different wavelengths (e.g., within different spectral bands detected by the spectral detectors of the optical sensor) produced by the illumination source)(e.g., based on one or more calibration measurements, each obtained by directing the illumination beam and the sensor ifov to a calibration panel having a known spectral reflectivity and detecting light reflected by the calibration panel).

In certain embodiments, the instructions cause the processor to calibrate the data to account for atmospheric absorption [e.g., based on two or more atmospheric calibration measurements, each obtained by detecting light from the illumination source reflected by a corresponding reflective object (e.g., a reflector panel; e.g., an in-scene reflector (e.g., a natural object such as concrete, wood, asphalt, dirt, grass, and the like, present in the scene, e.g., on the target surface), wherein each corresponding reflective object is at different distance (e.g., a known distance) from the optical sensor and has a same spectral reflectivity, and wherein a location of each corresponding reflective object is such that absorption along a path traversed by light from the corresponding reflective object to the optical sensor is due solely to atmospheric absorption (e.g., the path does not cross any gas clouds of compounds of interest)].

In certain embodiments, the instructions cause the processor to calibrate the data to account for a spectral dependence of reflectivities of in-scene reflective objects [e.g., natural objects (e.g., concrete, wood, asphalt, dirt, grass, etc.) which may have different wavelength dependent reflectivities][e.g., using adaptive gains specific to different materials (e.g., previously determined adaptive gains; e.g., adaptive gains determined using measurement from different spectral filters)].

In another aspect, the invention is directed to a system for obtaining a multispectral absorption image of a scene using a structured illumination beam produced by an illumination source mechanically coupled to a scanning optical sensor, the system comprising: (a) an illumination source aligned and operable to produce a structured illumination beam and direct the structured illumination beam towards a target surface [e.g., an approximately vertical wall (e.g., upon which structures such as gas plumbing, meters, valves, etc. are mounted); e.g., an approximately horizontal surface (e.g., such as ground of a site to be imaged; e.g., a ceiling above a structure to be inspected, such as a compressor, a well, etc.)] within the scene, thereby illuminating an illumination spot corresponding to a projection of the structured illumination beam onto the target surface, the illumination spot having a length (e.g., a spot size measured along a long axis) and a width (e.g., a spot size measured along a short axis that is approximately orthogonal to the long axis), wherein the length is greater than or equal to the width (e.g., wherein the illumination spot is an approximately rectangular spot; e.g., wherein the illumination spot is an approximately ellipsoidal spot and its length corresponds to a major axis of the approximately ellipsoidal spot); (b) an optical sensor comprising one or more spectral detectors, each aligned and operable to detect light having wavelengths within a particular associated spectral band, wherein the optical sensor is aligned and operable to capture light from (e.g., emitted and/or reflected by objects within) the scene within a sensor instantaneous field of view (ifov) corresponding to a combined ifov of the one or more spectral detectors (e.g., each spectral detector having an individual ifov wherein light from the scene within a particular spectral detector's individual ifov is captured and directed onto the particular spectral detector, and wherein the sensor ifov corresponds to a combination of all the individual ifov's of the spectral detectors) and direct it, for detection, onto the one or more detectors, thereby detecting light that from a particular sampled image location corresponding to a projection of the sensor ifov onto the target surface [e.g., the detected light having been attenuated (e.g., due to absorption) as it travels from the sampled image location to the optical sensor]; (c) an optical sensor scanner aligned and operable to scan the projection of the sensor ifov along a first scan axis directed along the length of the illumination spot; (d) a rotational stage on which the illumination source, optical sensor, and optical sensor scanner are mounted and aligned (e.g., in proximity to each other; e.g., vertically on top of each other) such that at least a portion of the first scan axis is held substantially coincident with a long axis directed along the length of the illumination spot, and scanning the projection of the sensor ifov along the first scan axis scans it over the illumination spot, along its length (e.g., such that the projection of the sensor ifov overlaps with the illumination spot as it is scanned along the length of the illumination spot), wherein the rotational stage is operable to rotate about a rotational axis [e.g., substantially parallel to: e.g., inclined (e.g., forward or backwards) with respect to the first scan axis], such that (i) rotation of the rotational stage scans the illumination spot and projection of the sensor ifov together across the scene in a second scan direction that is substantially orthogonal to the first scan axis, and (ii) scanning of the projection of the sensor ifov by the optical scanner in combination with rotation of the rotational stage raster scans the projection of the sensor ifov across the scene, thereby detecting light from a plurality of sampled image locations within the scene, each corresponding to a particular position of the projection of the sensor ifov within the raster scan; (e) a processor of a computing device; and (f) a memory having instructions stored thereon, wherein the instructions, when executed by the processor, cause the processor to: retrieve and/or access data corresponding to the detected light for each of the sampled image locations; and use the data to create a multispectral absorption image of the scene [e.g., wherein the multispectral absorption image comprises a plurality of image pixels, each (i) corresponding to a particular physical location within the scene (e.g., within a target region of the target surface) and (ii) having one or more intensity values each representing a level of absorption within a particular spectral band and determined using the data corresponding to the detected light from each of the sampled image locations].

In certain embodiments, the length of the illumination spot is a factor of approximately 10 or more greater than its width (e.g., a factor of approximately 20 or more greater than its width; e.g., a factor of approximately 50 or more greater than its width; e.g., a factor of approximately 100 or more greater than its width).

In certain embodiments, the width of the illumination spot is greater than or approximately equal to a size of the projection of the sensor ifov measured along a same direction (e.g., no less than the size of the projection of the sensor ifov measured along the same direction; e.g., no less than 1.5 times the size of the projection of the sensor ifov measured along the same direction; e.g., no less than 2 times the size of the projection of the sensor ifov measured along the same direction).

In certain embodiments, the rotation stage is operable rotate in a step-wise fashion [e.g., such that rotation of the rotational stage scans the illumination spot and the projection of the sensor ifov through a plurality of steps along the second scan direction (e.g., and wherein, for each of the plurality of steps along the second scan direction, the optical sensor scanner is operable to scan the projection along the sensor ifov along the first scan axis (e.g., across the length of the illumination spot))].

In certain embodiments, the rotational stage is operable to rotate about the rotational axis in a continuous fashion, at a rotational scan rate (e.g., a slow scan rate), and wherein the optical sensor scanner is operable to scan the projection of the ifov along the first scan axis at a fast scan rate (e.g., in a continuous fashion) that is greater than the rotational rate.

In certain embodiments, the fast scan rate is sufficiently fast in comparison with the rotational scan rate so as to allow for the projection of the sensor ifov to be scanned across a desired distance along the first scan axis before it is moved an appreciable distance (e.g., before it is moved a distance corresponding to a size of an individual ifov of an individual spectral detector of the optical sensor) along the second scan direction.

In certain embodiments, the fast scan rate is a factor of approximately 10 or more (e.g., a factor of approximately 20; e.g., a factor of approximately 50; e.g., a factor of approximately 100; e.g., a factor of approximately 1000) greater than the rotational scan rate.

In certain embodiments, the fast scan rate is sufficiently fast so as to allow for the projection of the sensor ifov to be scanned through multiple (e.g., at least 10; e.g., at least 20; e.g., at least 50; e.g., at least 100; e.g., at least 1000) sampled image locations along the length of the illumination spot before the illumination spot moves the appreciable distance.

In certain embodiments, the target surface is a substantially horizontal surface (e.g., ground of a site to be imaged and on which various structures may be located) and the illumination source is positioned in an elevated position above the target surface (e.g., overlooking the site to be imaged) and aligned to direct the structured beam of illumination towards the target surface and outwards (e.g., obliquely), such that the length of the illumination spot is directed outwards from a location beneath the illumination source.

In certain embodiments, the target surface is a substantially horizontal surface (e.g., a ceiling above a structure to be inspected, such as a compressor, a well, etc.) and the illumination source is positioned below the target surface (e.g., looking upwards at the site to be imaged) and aligned to direct the structured beam of illumination towards the target surface and outwards (e.g., obliquely), such that the length of the illumination spot is directed outwards from a location above the illumination source.

In certain embodiments, the target surface is a substantially vertical surface [e.g., a wall upon which structures (e.g., gas plumbing, meters, valves, etc.) are mounted](e.g., at similar height to the optical sensor and/or illumination source).

In certain embodiments, the length of the illumination spot is greater than or equal to a first dimension of a target region within the target surface, the rotational stage is operable to scan the illumination spot and projection of the ifov in the second scan direction across a distance greater than or equal to a second dimension of the target region, the optical sensor scanner is operable to scan the projection of the sensor ifov along the first scan axis over a distance greater than or equal to the first dimension of the target region.

In certain embodiments, the rotational stage is repositionable so as to provide for scanning of the illumination spot and projection of the ifov over multiple target regions [e.g., thereby providing for imaging over a large-scale region having dimensions larger than at least one of (i) a length of the illumination spot, (ii) a distance over which the rotational stage is operable to scan, and (iii) a distance over which the optical sensor scanner is operable to scan the projection of the ifov; e.g., thereby providing for scanning over multiple target regions that are spaced apart from one another].

In certain embodiments, the structured illumination beam is structured spatially to compensate for dilution of projected power with range [e.g., such that an intensity of the illumination spot is substantially uniform along its length; e.g., such that an intensity of the illumination spot is above a predetermined threshold level (e.g., sufficient for providing for imaging at or above a particular signal to noise ratio) across its length].

In certain embodiments, the illumination source comprises a plurality of emitters each of which outputs illumination light, wherein the illumination light output from the plurality of emitters is combined to produce the structured beam of illumination [e.g., wherein the plurality of emitters are arranged in a chain aligned with the length of the illumination spot and each emitter outputs illumination light at a different power level (e.g., the power level increasing along the chain, from one end of the chain to another)].

In certain embodiments, the structured beam of illumination comprises short wave infrared (SWIR) light (e.g., light having wavelengths ranging from approximately 1 to 2.6 microns), and the one or more spectral detectors are responsive to SWIR light [e.g., thereby providing for absorption based imaging using SWIR light, relevant for detection of hydrocarbon compounds].

In certain embodiments, the structured beam of illumination comprises visible light (e.g., light having wavelengths ranging from approximately 400 to 700 nanometers) and the one or more detectors are responsive to visible light [e.g., thereby providing for absorption based imaging using visible light, e.g., relevant for imaging based on electronic transitions of compounds of interest; e.g., relevant for hydrogen detection].

In certain embodiments, the multispectral absorption image comprises a plurality of image pixels, each (i) corresponding to a particular physical location within the scene (e.g., within a target region of the target surface) and (ii) having one or more intensity values each representing a level of absorption within a corresponding particular spectral band and determined using the data corresponding to the detected light from each of the sampled image locations.

In certain embodiments, for each of at least a portion of the intensity values, the corresponding particular spectral band comprises one or more absorption lines of a specific compound of interest [e.g., wherein the particular spectral band is an extended spectral band, spanning approximately 50 nanometers or more (e.g., spanning from 50 to 200 nanometers; e.g., spanning from 50 to 100 nanometers); e.g., spanning approximately 100 nanometers or more (e.g., spanning from 100 to 200 nanometers)].

In certain embodiments, the optical sensor comprises at least one spectral filter positioned in front of at least a portion of the one or more spectral detectors, wherein the at least one spectral filter is substantially transmissive to light having a wavelength within a specific spectral band of the corresponding particular spectral band(s) and substantially opaque to light having a wavelength outside of the specific spectral band.

In certain embodiments, the instructions cause the processor to calibrate the data to account for spectral content of the illumination source (e.g., differences in amount of light at different wavelengths (e.g., within different spectral bands detected by the spectral detectors of the optical sensor) produced by the illumination source)(e.g., based on one or more calibration measurements, each obtained by directing the illumination beam and the sensor ifov to a calibration panel having a known spectral reflectivity and detecting light reflected by the calibration panel).

In certain embodiments, the instructions cause the processor to calibrate the data to account for atmospheric absorption [e.g., based on two or more atmospheric calibration measurements, each obtained by detecting light from the illumination source reflected by a corresponding reflective object (e.g., a reflector panel; e.g., an in-scene reflector (e.g., a natural object such as concrete, wood, asphalt, dirt, grass, and the like, present in the scene, e.g., on the target surface), wherein each corresponding reflective object is at different distance (e.g., a known distance) from the optical sensor and has a same spectral reflectivity, and wherein a location of each corresponding reflective object is such that absorption along a path traversed by light from the corresponding reflective object to the optical sensor is due solely to atmospheric absorption (e.g., the path does not cross any gas clouds of compounds of interest)].

In certain embodiments, the instructions cause the processor to calibrate the data to account for a spectral dependence of reflectivities of in-scene reflective objects [e.g., natural objects (e.g., concrete, wood, asphalt, dirt, grass, etc.) which may have different wavelength dependent reflectivities][e.g., using adaptive gains specific to different materials (e.g., previously determined adaptive gains; e.g., adaptive gains determined using measurement from different spectral filters)].

In another aspect, the invention is directed to a method of obtaining a multispectral absorption image of a scene using a structured illumination beam that is scanned in a synchronized fashion with an instantaneous field of view (ifov) of an optical sensor, the method comprising: (a) directing the structured illumination beam from an illumination source towards a target surface (e.g., an approximately vertical wall; e.g., an approximately horizontal surface such as ground of a site to be imaged) within the scene, thereby illuminating an illumination spot corresponding to a projection of the structured illumination beam onto the target surface, wherein the illumination spot has a length (e.g., a spot size of measured along a long axis) and a width (e.g., a spot size measured along a short axis that is approximately orthogonal to the long axis), wherein the length is greater than or equal to the width (e.g., wherein the illumination spot is an approximately rectangular spot; e.g., wherein the illumination spot is an approximately ellipsoidal spot and its length corresponds to a major axis of the approximately ellipsoidal spot); (b) scanning (e.g., by a beam scanner) the illumination spot in a beam scan direction that is substantially along its width (e.g., and across a distance greater than or approximately equal to the width of the illumination spot); (c) detecting, with one or more spectral detectors of an optical sensor, light from (e.g., emitted and/or reflected by objects within) the scene and captured within the ifov of the optical sensor, thereby detecting light from a particular sampled image location corresponding to a projection of the sensor ifov onto the target surface [e.g., the detected light having been attenuated (e.g., due to absorption) as it travels from the sampled image location to the optical sensor]; (d) scanning (e.g., by an optical sensor scanner) the projection of the sensor ifov across the scene, so as to detect light from a plurality of sampled image locations within the scene, wherein the optical sensor scanner is synchronized with the beam scanner and so as to maintain overlap between the projection of the sensor ifov and the illumination spot as both are scanned; (e) retrieving and/or accessing, by a processor of a computing device, data corresponding to the detected light for each of the sampled image locations; and (f) creating, by the processor, using the data, a multispectral absorption image of the scene [e.g., wherein the multispectral absorption image comprises a plurality of image pixels, each (i) corresponding to a particular physical location within the scene (e.g., within a target region of the target surface) and (ii) having one or more intensity values each representing a level of absorption within a particular spectral band and determined using the data corresponding to the detected light from each of the sampled image locations].

In certain embodiments, the length of the illumination spot is a factor of approximately 10 or more greater than its width (e.g., a factor of approximately 20 or more greater than its width; e.g., a factor of approximately 50 or more greater than its width; e.g., a factor of approximately 100 or more greater than its width). In certain embodiments, the width of the illumination spot is greater than or approximately equal to a size of the projection of the sensor ifov measured along a same direction (e.g., no less than the size of the projection of the sensor ifov measured along the same direction; e.g., no less than 1.5 times the size of the projection of the sensor ifov measured along the same direction; e.g., no less than 2 times the size of the projection of the sensor ifov measured along the same direction).

In certain embodiments, step (d) comprises scanning the projection of the sensor ifov along a first scan axis (e.g., a fast axis) aligned along the length of the illumination spot and scanning the projection of the ifov along a second scan axis (e.g., a slow axis) aligned along the width of the illumination spot.

In certain embodiments, the method comprises scanning the projection of the sensor ifov along the second scan axis in a step-wise fashion, and, for each of a plurality of steps in the step-wise scan along the second scan axis, scanning the projection of the sensor ifov along the first scan axis [e.g., wherein step (b) comprises scanning the illumination spot in a step-wise fashion; e.g., wherein step (b) comprises scanning the illumination spot in a continuous fashion at a beam scan rate (e.g., less than the rate of the scanning of the projection of the sensor ifov along the first scan axis)].

In certain embodiments, the first scan axis is a fast scan axis and the second scan axis is a slow scan axis and the method comprises: scanning the scanning the projection of the sensor ifov at a fast scan rate along the fast scan axis (e.g., in a continuous fashion); and scanning projection of the sensor ifov at a slow scan rate along the slow scan axis (e.g., in a continuous fashion)[e.g., wherein the beam scanner is also operable to scan the illumination spot in a step-wise fashion; e.g., wherein the beam scanner is operable to scan the illumination spot in a continuous fashion at a beam scan rate (e.g., less than the rate at which the optical sensor scanner is operable to scan the projection of the sensor ifov along the first scan axis) comparable to the slow scan rate].

In certain embodiments, the fast scan rate is sufficiently fast in comparison with the slow scan rate so as to allow for the projection of the sensor ifov to be scanned across a desired distance along the fast scan axis before it is moved an appreciable distance (e.g., before it is moved a distance corresponding to a size of an individual ifov of an individual spectral detector of the optical sensor) along the slow scan axis.

In certain embodiments, the fast scan rate is a factor of approximately 10 or more (e.g., a factor of approximately 20; e.g., a factor of approximately 50; e.g., a factor of approximately 100; e.g., a factor of approximately 1000) greater than the slow scan rate.

In certain embodiments, the fast scan rate is sufficiently fast so as to allow for the projection of the sensor ifov to be scanned through multiple (e.g., at least 10; e.g., at least 20; e.g., at least 50, e.g., at least 100; e.g., at least 1000) sampled image locations along the length of the illumination spot before the illumination spot moves the appreciable distance.

In certain embodiments, the target surface is a substantially horizontal surface (e.g., ground of a site to be imaged and on which various structures may be located) and the illumination source is positioned in an elevated position above the target surface (e.g., overlooking the site to be imaged) and aligned to direct the structured beam of illumination towards the target surface and outwards (e.g., obliquely), such that the length of the illumination spot is directed outwards from a location beneath the illumination source.

In certain embodiments, the target surface is a substantially horizontal surface (e.g., a ceiling above a structure to be inspected, such as a compressor, a well, etc.) and the illumination source is positioned below the target surface (e.g., looking upwards at the site to be imaged) and aligned to direct the structured beam of illumination towards the target surface and outwards (e.g., obliquely), such that the length of the illumination spot is directed outwards from a location above the illumination source.

In certain embodiments, the target surface is a substantially vertical surface [e.g., a wall upon which structures (e.g., gas plumbing, meters, valves, etc.) are mounted](e.g., at similar height to the optical sensor and/or illumination source).

In certain embodiments, the length of the illumination spot is greater than or equal to a first dimension of a target region within the target surface, and wherein the method comprises: at step (b), scanning the illumination spot in the beam scan direction across a distance greater than or equal to a second dimension of the target region, at step (c), raster scanning the projection of the sensor ifov across the target region [e.g., by (i) scanning the projection of the sensor ifov along a first scan axis directed along the length of the illumination spot and over a distance greater than or equal to the first dimension of the target region and (ii) scanning the projection of the sensor ifov along a second scan axis over a distance greater than or equal to the second dimension of the target region].

In certain embodiments, the method comprises: performing steps (a) to (d) to detect light from first set of sampled image locations within a first target region; repositioning (i) a beam scanner operable to scan the illumination spot [e.g., as in step (b)] and/or (ii) an optical sensor scanner operable to scan the projection of the sensor ifov [e.g., as in step (d)]; and performing steps (a) to (d) to detect light from a second set of sampled image locations within a second target region [e.g., so as to image over multiple target regions; e.g., thereby providing for imaging over a large-scale region having dimensions larger than at least one of (i) a length of the illumination spot; (ii) a distance over which the beam scanner is operable to scan; (iii) a distance over which the optical sensor scanner is operable to scan the projection of the ifov; e.g., thereby providing for scanning over multiple target regions that are spaced apart from one another].

In certain embodiments, the structured illumination beam is structured spatially to compensate for dilution of projected power with range [e.g., such that an intensity of the illumination spot is substantially uniform along its length; e.g., such that an intensity of the illumination spot is above a predetermined threshold level (e.g., sufficient for providing for imaging at or above a particular signal to noise ratio) across its length].

In certain embodiments, the illumination source comprises a plurality of emitters each of which outputs illumination light, wherein the illumination light output from the plurality of emitters is combined to produce the structured beam of illumination [e.g., wherein the plurality of emitters are arranged in a chain aligned with the length of the illumination spot and each emitter outputs illumination light at a different power level (e.g., the power level increasing along the chain, from one end of the chain to another)].

In certain embodiments, the structured beam of illumination comprises short wave infrared (SWIR) light (e.g., light having wavelengths ranging from approximately 1 to 2.6 microns), and the one or more spectral detectors are responsive to SWIR light [e.g., thereby providing for absorption based imaging using SWIR light, relevant for detection of hydrocarbon compounds].

In certain embodiments, the structured beam of illumination comprises visible light (e.g., light having wavelengths ranging from approximately 400 to 700 nanometers) and the one or more detectors are responsive to visible light [e.g., thereby providing for absorption based imaging using visible light. e.g., relevant for imaging based on electronic transitions of compounds of interest; e.g., relevant for hydrogen detection].

In certain embodiments, the multispectral absorption image comprises a plurality of image pixels, each (i) corresponding to a particular physical location within the scene (e.g., within a target region of the target surface) and (ii) having one or more intensity values each representing a level of absorption within a corresponding particular spectral band and determined using the data corresponding to the detected light from each of the sampled image locations.

In certain embodiments, for each of at least a portion of the intensity values, the corresponding particular spectral band comprises one or more absorption lines of a specific compound of interest [e.g., wherein the particular spectral band is an extended spectral band, spanning approximately 50 nanometers or more (e.g., spanning from 50 to 200 nanometers; e.g., spanning from 50 to 100 nanometers); e.g., spanning approximately 100 nanometers or more (e.g., spanning from 100 to 200 nanometers)].

In certain embodiments, the optical sensor comprises at least one spectral filter positioned in front of at least a portion of the one or more spectral detectors, wherein the at least one spectral filter is substantially transmissive to light having a wavelength within a specific spectral band of the corresponding particular spectral band(s) and substantially opaque to light having a wavelength outside of the specific spectral band.

In certain embodiments, step (f) comprises calibrating the data to account for spectral content of the illumination source (e.g., differences in amount of light at different wavelengths (e.g., within different spectral bands detected by the spectral detectors of the optical sensor) produced by the illumination source)(e.g., based on one or more calibration measurements, each obtained by directing the illumination beam and the sensor ifov to a calibration panel having a known spectral reflectivity and detecting light reflected by the calibration panel).

In certain embodiments, step (f) comprises calibrating the data to account for atmospheric absorption [e.g., based on two or more atmospheric calibration measurements, each obtained by detecting light from the illumination source reflected by a corresponding reflective object (e.g., a reflector panel. e.g., an in-scene reflector (e.g., a natural object such as concrete, wood, asphalt, dirt, grass, and the like, present in the scene, e.g., on the target surface), wherein each corresponding reflective object is at different distance (e.g., a known distance) from the optical sensor and has a same spectral reflectivity, and wherein a location of each corresponding reflective object is such that absorption along a path traversed by light from the corresponding reflective object to the optical sensor is due solely to atmospheric absorption (e.g., the path does not cross any gas clouds of compounds of interest)].

In certain embodiments, step (f) comprises calibrating the data to account for a spectral dependence of reflectivities of in-scene reflective objects [e.g., natural objects (e.g., concrete, wood, asphalt, dirt, grass, etc.) which may have different wavelength dependent reflectivities][e.g., using adaptive gains specific to different materials (e.g., previously determined adaptive gains; e.g., adaptive gains determined using measurement from different spectral filters)].

In another aspect, the invention is directed to a method for obtaining a multispectral absorption image of a scene using a structured illumination beam produced by an illumination source mechanically coupled to a scanning optical sensor, the method comprising: (a) directing the structured illumination beam from the illumination source towards a target surface (e.g., an approximately vertical wall; e.g., an approximately horizontal surface such as ground of a site to be imaged; e.g., an approximately horizontal surface such as a ceiling above a site to be imaged) within the scene, thereby illuminating an illumination spot corresponding to a projection of the structured illumination beam onto the target surface, wherein the illumination spot has a length (e.g., a spot size of measured along a long axis) greater than or equal to a first dimension of a target region of the target surface (e.g., wherein the illumination spot is an approximately rectangular spot; e.g., wherein the illumination spot is an approximately ellipsoidal spot and its length corresponds to a major axis of the approximately ellipsoidal spot) a width (e.g., a spot size measured along a short axis that is approximately orthogonal to the long axis) less than its length; (b) detecting, with one or more detectors of an optical sensor, light from (e.g., emitted and/or reflected by objects within) the scene and captured within the ifov of the optical sensor, thereby detecting light that originates from a particular sampled image location corresponding to a projection of the sensor ifov onto the target surface [e.g., the detected light having been attenuated (e.g., due to absorption) as it travels from the sampled image location to the optical sensor]; (c) scanning (e.g., by an optical sensor scanner) the projection of sensor ifov along a first scan axis (e.g., a fast axis), substantially parallel to a direction along the length of the illumination spot and at least a portion of which is substantially coincident with a long axis aligned along the length of the illumination spot, such that scanning the projection of the sensor ifov along the first scan axis scans it over the illumination spot, along its length (e.g., such that the projection of the sensor ifov overlaps with the illumination spot as it is scanned along the length of the illumination spot); (d) rotating, via a rotational stage on which both the illumination source and optical sensor are mounted and maintained in substantially fixed alignment with respect to each other, the illumination source and optical sensor about a rotational axis [e.g., wherein the rotational axis is substantially parallel to the first scan axis; e.g., wherein the rotational axis is inclined (e.g., forward or backwards) with respect to the first scan axis], such that (i) rotation of the rotational stage scans the illumination spot and the projection of the sensor ifov together across the scene (e.g., across a target region of the target surface) in a second scan direction that is substantially orthogonal to the first scan axis, and (ii) scanning of the projection of the sensor ifov along the first scan axis in combination with rotation of the rotational stage raster scans the projection of the sensor ifov across the scene (e.g., across a target region of the target surface), thereby providing for detection of light from a plurality of sampled image locations within the scene, each corresponding to a particular position of the projection of the sensor ifov within the raster scan; (e) retrieving and/or accessing, by a processor of a computing device, data corresponding to the detected light for each of the sampled image locations; and (f) creating, by the processor, using the data, a multispectral absorption image of the scene [e.g., wherein the multispectral absorption image comprises a plurality of image pixels, each (i) corresponding to a particular physical location within the scene (e.g., within a target region of the target surface) and (ii) having one or more intensity values each representing a level of absorption within a particular spectral band and determined using the data corresponding to the detected light from each of the sampled image locations]

In certain embodiments, the length of the illumination spot is a factor of approximately 10 or more greater than its width (e.g., a factor of approximately 20 or more greater than its width; e.g., a factor of approximately 50 or more greater than its width; e.g., a factor of approximately 100 or more greater than its width).

In certain embodiments, the width of the illumination spot is greater than or approximately equal to a size of the projection of the sensor ifov measured along a same direction (e.g., no less than the size of the projection of the sensor ifov measured along the same direction; e.g., no less than 1.5 times the size of the projection of the sensor ifov measured along the same direction; e.g., no less than 2 times the size of the projection of the sensor ifov measured along the same direction).

In certain embodiments, step (d) comprises rotating, via the rotational stage, the illumination source and the optical sensor in a step-wise fashion [e.g., such that rotation of the rotational stage scans the illumination spot and the projection of the sensor ifov through a plurality of steps along the second scan direction (e.g., and wherein the method comprises, for each of the plurality of steps along the second scan direction, scanning (e.g., via an optical sensor scanner) the projection along the sensor ifov along the first scan axis (e.g., across the length of the illumination spot))].

In certain embodiments, step (d) comprises rotating, via the rotational stage, the illumination source and the optical sensor in a continuous fashion, at a rotational scan rate (e.g., a slow scan rate), and wherein step (c) comprises scanning the projection of the ifov along the first scan axis at a fast scan rate (e.g., in a continuous fashion) that is greater than the rotational rate.

In certain embodiments, the fast scan rate is sufficiently fast in comparison with the rotational scan rate so as to allow for the projection of the sensor ifov to be scanned across a desired distance along the first scan axis before it is moved an appreciable distance (e.g., before it is moved a distance corresponding to a size of an individual ifov of an individual spectral detector of the optical sensor) along the second scan direction.

In certain embodiments, the fast scan rate is a factor of approximately 10 or more (e.g., a factor of approximately 20; e.g., a factor of approximately 50; e.g., a factor of approximately 100; e.g., a factor of approximately 1000) greater than the rotational scan rate.

In certain embodiments, the fast scan rate is sufficiently fast so as to allow for the projection of the sensor ifov to be scanned through multiple (e.g., at least 10; e.g., at least 20; e.g., at least 50; e.g., at least 100; e.g., at least 1000) sampled image locations along the length of the illumination spot before the illumination spot moves the appreciable distance.

In certain embodiments, the target surface is a substantially horizontal surface (e.g., ground of a site to be imaged and on which various structures may be located) and the illumination source is positioned in an elevated position above the target surface (e.g., overlooking the site to be imaged) and aligned to direct the structured beam of illumination towards the target surface and outwards (e.g., obliquely), such that the length of the illumination spot is directed outwards from a location beneath the illumination source.

In certain embodiments, the target surface is a substantially horizontal surface (e.g., a ceiling above a structure to be inspected, such as a compressor, a well, etc.) and the illumination source is positioned below the target surface (e.g., looking upwards at the site to be imaged) and aligned to direct the structured beam of illumination towards the target surface and outwards (e.g., obliquely), such that the length of the illumination spot is directed outwards from a location above the illumination source.

In certain embodiments, the target surface is a substantially vertical surface [e.g., a wall upon which structures (e.g., gas plumbing, meters, valves, etc.) are mounted](e.g., at similar height to the optical sensor and/or illumination source).

In certain embodiments, the length of the illumination spot is greater than or equal to a first dimension of a target region within the target surface, and wherein the method comprises: at step (c), scanning the projection of the sensor ifov along the first scan axis over a distance greater than or equal to the first dimension of the target region; and at step (d), rotating, via the rotational stage, the illumination source and the optical sensor so as to scan the illumination spot and projection of the ifov in the second scan direction across a distance greater than or equal to a second dimension of the target region.

In certain embodiments, the method comprises: performing steps (a) to (d) to detect light from a first set of sampled image locations within a first target region; repositioning the rotational stage; and performing steps (a) to (d) to detect light from a second set of sampled image locations within a second target region [e.g., so as to provide for scanning of the illumination spot and projection of the ifov over multiple target regions; e.g., thereby providing for imaging over a large-scale region having dimensions larger than at least one of (i) a length of the illumination spot, (ii) a distance over which the rotational stage is operable to scan, and (iii) a distance over which the optical sensor scanner is operable to scan the projection of the ifov; e.g., thereby providing for scanning over multiple target regions that are spaced apart from one another].

In certain embodiments, the structured illumination beam is structured spatially to compensate for dilution of projected power with range [e.g., such that an intensity of the illumination spot is substantially uniform along its length; e.g., such that an intensity of the illumination spot is above a predetermined threshold level (e.g., sufficient for providing for imaging at or above a particular signal to noise ratio) across its length].

In certain embodiments, the illumination source comprises a plurality of emitters each of which outputs illumination light, wherein the illumination light output from the plurality of emitters is combined to produce the structured beam of illumination [e.g., wherein the plurality of emitters are arranged in a chain aligned with the length of the illumination spot and each emitter outputs illumination light at a different power level (e.g., the power level increasing along the chain, from one end of the chain to another)].

In certain embodiments, the structured beam of illumination comprises short wave infrared (SWIR) light (e.g., light having wavelengths ranging from approximately 1 to 2.6 microns), and the one or more spectral detectors are responsive to SWIR light [e.g., thereby providing for absorption based imaging using SWIR light, relevant for detection of hydrocarbon compounds].

In certain embodiments, the structured beam of illumination comprises visible light (e.g., light having wavelengths ranging from approximately 400 to 700 nanometers) and the one or more detectors are responsive to visible light [e.g., thereby providing for absorption based imaging using visible light, e.g., relevant for imaging based on electronic transitions of compounds of interest; e.g., relevant for hydrogen detection].

In certain embodiments, the multispectral absorption image comprises a plurality of image pixels, each (i) corresponding to a particular physical location within the scene (e.g., within a target region of the target surface) and (ii) having one or more intensity values each representing a level of absorption within a corresponding particular spectral band and determined using the data corresponding to the detected light from each of the sampled image locations.

In certain embodiments, for each of at least a portion of the intensity values, the corresponding particular spectral band comprises one or more absorption lines of a specific compound of interest [e.g., wherein the particular spectral band is an extended spectral band, spanning approximately 50 nanometers or more (e.g., spanning from 50 to 200 nanometers; e.g., spanning from 50 to 100 nanometers); e.g., spanning approximately 100 nanometers or more (e.g., spanning from 100 to 200 nanometers)].

In certain embodiments, the optical sensor comprises at least one spectral filter positioned in front of at least a portion of the one or more spectral detectors, wherein the at least one spectral filter is substantially transmissive to light having a wavelength within a specific spectral band of the corresponding particular spectral band(s) and substantially opaque to light having a wavelength outside of the specific spectral band.

In certain embodiments, step (f) comprises calibrating the data to account for spectral content of the illumination source (e.g., differences in amount of light at different wavelengths (e.g., within different spectral bands detected by the spectral detectors of the optical sensor) produced by the illumination source)(e.g., based on one or more calibration measurements, each obtained by directing the illumination beam and the sensor ifov to a calibration panel having a known spectral reflectivity and detecting light reflected by the calibration panel).

In certain embodiments, step (f) comprises calibrating the data to account for atmospheric absorption [e.g., based on two or more atmospheric calibration measurements, each obtained by detecting light from the illumination source reflected by a corresponding reflective object (e.g., a reflector panel; e.g., an in-scene reflector (e.g., a natural object such as concrete, wood, asphalt, dirt, grass, and the like, present in the scene, e.g., on the target surface), wherein each corresponding reflective object is at different distance (e.g., a known distance) from the optical sensor and has a same spectral reflectivity, and wherein a location of each corresponding reflective object is such that absorption along a path traversed by light from the corresponding reflective object to the optical sensor is due solely to atmospheric absorption (e.g., the path does not cross any gas clouds of compounds of interest)].

In certain embodiments, step (f) comprises calibrating the data to account for a spectral dependence of reflectivities of in-scene reflective objects [e.g., natural objects (e.g., concrete, wood, asphalt, dirt, grass, etc.) which may have different wavelength dependent reflectivities][e.g., using adaptive gains specific to different materials (e.g., previously determined adaptive gains; e.g., adaptive gains determined using measurement from different spectral filters)].

BRIEF DESCRIPTION OF THE DRAWING

The patent or application file contains at least one drawing executed in color. Copies of this patent or patent application publication with color drawing(s) will be provided by the Office upon request and payment of the necessary fee.

The foregoing and other objects, aspects, features, and advantages of the present disclosure will become more apparent and better understood by referring to the following description taken in conjunction with the accompanying drawings, in which:

FIG. 1C is a block diagram of a leak imaging and quantification system, according to an illustrative embodiment:

FIG. 1D is a block diagram of an imaging system comprising a scanned optical sensor and illuminator, according to an illustrative embodiment:

FIG. 3 is a diagram of an embodiment of the illuminator-sensor system monitoring a gas well pad, with a sensor and illuminator mounted on a pan-tilt unit atop a mast, according to an illustrative embodiment;

Figure 1A:
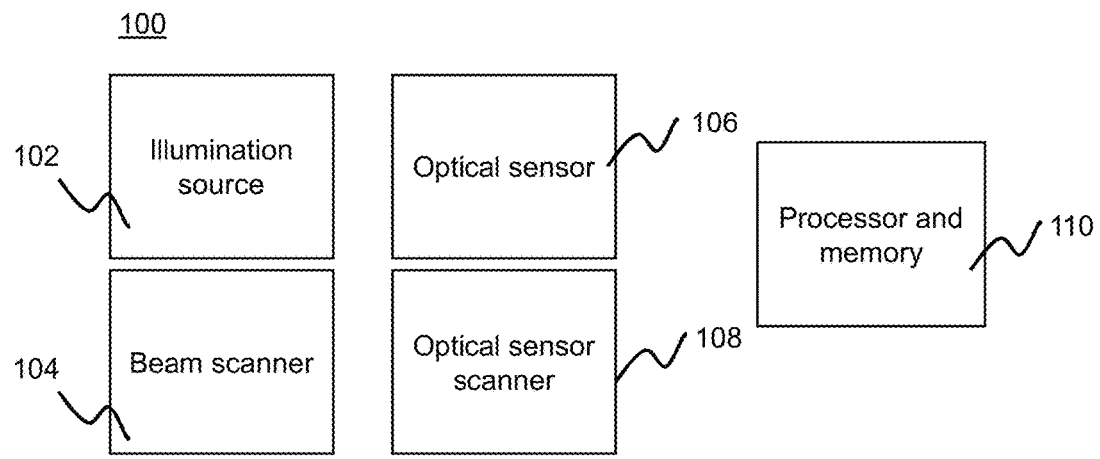
FIG. 1A is a block diagram of a system for obtaining a multispectral absorption image of a scene using a structured illumination beam scanned in synchrony with an instantaneous field of view (ifov) of a scanning optical sensor.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

Elements of embodiments described with respect to a given aspect of the invention may be used in various embodiments of another aspect of the invention. For example, it is contemplated that features of dependent claims depending from one independent claim can be used in apparatus, articles, systems, and/or methods of any of the other independent claims.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are provided for the convenience of the reader—the presence and/or placement of a header is not intended to limit the scope of the subject matter described herein.

The systems and method described herein relate to multispectral optical sensors that are used to obtain multispectral absorption images of scenes, for example to detect leaking gas. In certain embodiments, the optical sensors described herein comprise multiple detectors (e.g., spectral detectors), each aligned and operable to detect light with in a particular associated spectral band. As used herein, the term "detector", as used in reference to a detector of an optical sensor, refers to an individual detector element, such as a photodiode, or, in the context of a focal plane array, which comprises multiple detector pixels, a single detector pixel.

In such an optical sensor, each detector has its own individual detector instantaneous field of view (ifov), such that light from (e.g., emitted by and/or reflected by objects within) a scene within a particular detector's individual ifov is captured, incident on the particular detector, and detected. The overall ifov of the optical sensor corresponds to the combined ifov of the individual detectors that it comprises. As used herein with respect to an optical sensor comprising multiple detectors, the term "instantaneous field of view (ifov)", as in a "sensor ifov", an "ifov of an optical sensor", and the like, refers to the overall ifov of the optical sensor, corresponding to the combined ifov of all the individual detectors that it comprises.

As described above, improved systems and methods are needed to detect gas leaks. In certain embodiments, in order to repair such leaks, it is necessary to also localize the leak, and in order to prioritize repairs it is desirable to quantify the leak in terms of leak rate or emission flux. Estimating gas emission flux may also be needed to assess environmental impact of greenhouse gases. Moreover, it may be desirable to have a means to monitor or inspect wide areas for such leaks and do so quickly from a safe and practical standoff distance, while maintaining the ability to pinpoint the leak location and estimate the leak rate. It may also be desirable to conduct effective leak monitoring in the presence of naturally occurring ambient gases and vapors, such as water vapor, and regardless of the relative temperature between leaked gas and the background environment. The systems and methods described herein provide a cost-effective solution to the problems described above, and elsewhere herein, that may be broadly adopted and utilized.

Gas detectors can be classified according to their coverage extent, as either spot sensors, line sensors or area sensors. Spot sensors, often referred to as sniffers, draw in a local sample of air and detect the presence of a combustible or toxic gas by means of various analytical methods. They can be fixed in place for continuous monitoring, or hand-portable for inspections, but they require direct sampling in place and provide very limited coverage. They may provide concentration measurements but do not provide leak rate estimates. Other instrumentation is available to locally sample (as opposed to image) known leaks in order to provide an estimate of leak rate, but they too provide only local coverage and require direct collection of gas from the leaking component.

Optical line sensors, also known as open-path gas detectors, employ optical means to detect gas that lies along the line between a dedicated light emitter (e.g., laser, tunable laser, or narrowly focused broadband source) and a dedicated photo-detector (or multiple photo-detectors). Such detectors exploit the absorption of light (typically in different parts of the infrared spectrum) at select wavelengths characteristic of the molecular composition of the gas of interest. These sensors detect gas present anywhere along the line between the light emitter and the photo-detector (or between combined emitter/detector assembly and a remote reflector if the optical path is folded), but they cannot determine where along the path the gas is, nor from where it came. Optical line sensors also have limited coverage, which includes only the narrow open path between emitter and detector. By utilizing multiple wavelengths of light, such sensors can measure column density of gas along the open path but cannot measure or estimate concentration nor leak rate. Open-path sensors can be installed in place, hand-portable, or mobile aboard ground and air vehicles. In order to achieve area coverage from a standoff distance, it is recognized herein that imaging sensors offer many advantages over spot and line sensors, in that they can detect the presence of gas and possibly localize the leak source.

Previous gas imaging technologies are all based on the absorption of infrared light at wavelengths characteristic of the molecules of interest. For methane and hydrocarbons in general, most imagers operate in select bands of the mid-wave infrared and long-wave infrared spectrum. Commercially available gas imaging sensors commonly operate in only a single narrow band of the mid-wave infrared spectrum, and do not provide quantitative data. Instead, these gas imaging sensors only provide images to be interpreted by a human operator. Other imaging sensors utilize multiple spectral bands in the long-wave infrared (the so-called "molecular fingerprint region") to detect and discriminate among different hydrocarbon gases, and to quantify the column density of gas at each pixel of the image. The present disclosure encompasses the recognition that such systems are both expensive and have significant shortcomings. These mid-wave and long-wave infrared sensors rely on thermally emitted light from the background to illuminate the gas that will absorb at select wavelengths as detected by the imaging sensors. This requires that the background and gas differ in temperature by at least several degrees Celsius. Otherwise the light absorbed (or emitted) by the gas will not provide sufficient signal contrast to be reliably detected by the human operators of these thermal sensors. For example, in the case of surface emissions of natural gas due to an underground pipe leak, or methane emissions from a landfill, the gas percolates up through the soil and reaches thermal equilibrium with the soil by the time it emerges from the ground. Thus, there may be little or no thermal contrast between the gas and the ground. Therefore, gas cannot always be reliably detected by a thermal infrared sensor.

The present disclosure also encompasses the recognition of another major shortcoming of mid-wave and long-wave gas imaging sensors, namely their poor performance in the presence of water vapor (e.g., high humidity, e.g., steam), fog, and light rain. Performance of these conventional systems is poor in the presence of water vapor (e.g., high humidity, e.g., steam), fog, and light rain because the spectrum of water overlaps with key spectral features of methane in both the mid-wave and long-wave infrared spectral regions. Thus, water vapor will mask the presence of a methane leak, and conversely, water vapor will trigger a false alarm for methane. As both water vapor and methane are less dense than air, they both rise due to buoyancy and look alike in a spectrally filtered mid-wave or long-wave infrared image. Additionally, all mid-wave infrared and some long-wave infrared gas imaging sensors require cryogenic cooling, which is both expensive and unreliable. It is preferable to utilize only thermo-electric cooling to reduce dark current in gas imaging sensors. The present disclosure also encompasses the recognition of the problem that none of the available gas imaging sensors provides a capability to estimate leak rate from a hole, or emission flux from a surface.

In order to overcome the above-cited shortcomings of thermal infrared based imaging sensors for gas detection, it is possible to utilize differential absorption gas imaging in the short-wave infrared part of the spectrum, as described in certain embodiments of the systems and methods of the present disclosure. Atmospheric scientists using satellite-borne sensors like Landsat and SCIAMACHY have exploited this. Differential absorption gas imaging allows the detection of methane, other hydrocarbons, carbon dioxide, and other gases in the atmosphere based on molecular absorption of natural sunlight, without interference from intervening water vapor. Such space-based imaging technologies provide synoptic scale maps of column densities of greenhouse gases and other air pollutants.

This approaches described herein include an illuminator designed to project short-wave infrared light in a narrow stripe that is scanned across a scene, whereby a multispectral optical gas detection sensor scans the scene in synchrony with the illuminator. This illuminator provides the required intensity of light, e.g., in the absence of sufficient natural sunlight, for the sensor to detect the short-wave infrared spectral absorption signature of gases of interest (including hydrocarbons such as methane, ethane, propane, and butane and other gases of interest such as carbon dioxide and ammonia) as well as liquid oil spills on soil, sand, salt water, salt ice, and man-made surfaces.

The systems and methods of the present disclosure have applications in environmental monitoring for gaseous emissions, as well as applications related to gas safety. Several embodiments described herein support hand-portable battery-powered inspection of a site at ranges from approximately ¼- 5 meters, extended monitoring of a site using a mast-mounted configuration of powered illuminator and sensor at ranges of approximately 2-20 meters, and truck-mounted illuminator and sensor surveying of areas at extended ranges of approximately 5-50 meters.

In certain embodiments, the present disclosure describes an apparatus for providing short-wave infrared illumination structured in the form of a stripe that extends vertically or radially over objects or a surface (e.g., the ground), and is scanned in an orthogonal direction such that the illuminated stripe sweeps across a scene which may comprise one or more objects or sites of interest, e.g., a well pad, a compressor, or the ground above buried pipelines. This source of structured illumination may be used in the absence of sufficient sunlight and in combination with a multispectral short-wave infrared optical sensor designed to detect gaseous emissions, and possibly quantify the flux of such emissions. In certain embodiments, a scanning illuminator is synchronized with the scanning sensor, such that the sensor rapidly scans along the projected light stripe and both illuminator and sensor scan across the scene. Described herein are efficient embodiments of scanning optical gas sensors that are synchronized with a scanning illuminator. Embodiments and components of scanning optical sensors, appropriate for use in the systems and methods described herein are also described in U.S. patent application Ser. No. 15/598,052, entitled "Hydrocarbon Leak Imaging and Quantification Sensor", filed May 18, 2017 and U.S. Patent Application No., entitled "Scanning IR Sensor for Gas Safety and Emissions Monitoring", filed Mar. 16, 2018, the contents of each of which are hereby incorporated by reference in their entirety.

The systems described herein—which comprise, in certain embodiments, a short-wave infrared illuminator and a multispectral sensor—have several key advantages over thermal infrared gas imaging sensors that operate in the mid-wave and long-wave infrared regions of the spectrum. These advantages include, for example, the ability to detect and quantify leaked gas with no temperature difference relative to the background, as the presently described systems and methods may utilize short-wave infrared light provided by natural sunlight and/or by an illuminator of appropriate color temperature. Thus, the systems and methods described herein do not rely on thermal contrast between gas and background or a background of varying temperature. Moreover, in certain embodiments, the detectors suitable for use in this invention do not require cryogenic cooling. Rather, thermo-electric cooling may be used. Thermo-electric coolers are more reliable and less expensive than cryogenic coolers such as a Stirling engine or liquid nitrogen. The systems and methods described herein can also be used to detect gas leaks in the presence of humid air, steam and fog, because hydrocarbon features detected in short-wave infrared do not overlap spectral regions where water vapor absorption is significant, which is a problem for gas imagers operating in other parts of the infrared spectrum (i.e., mid-wave and long-wave infrared). Moreover, the systems and methods described herein can also be used to detect other gases including carbon dioxide and ammonia, and hydrocarbons in non-gaseous states, including liquids, emulsions, powders, and solids. The embodiment of a scan imager provides a cost-effective design, by allowing the use of a small number of discrete photo-diodes or small photo-diode array.

In many applications, gas imaging is conducted in the absence of sufficient sunlight. For example, sunlight may be insufficient as a sole illumination source for imaging outdoors in the shade or shadows, under overcast skies, and in darkness (e.g., at night). Likewise, indoor operations require artificial illumination. The desired illumination spans the spectral range of approximately 1000 to 2500 nanometers and is characteristic of a blackbody radiator at a temperature of approximately 1200° C. Such illumination can be efficiently generated using a carbon filament illuminator, which typically emits approximately 75 watts per inch of filament (sometimes coiled in a loose helical pattern). Other sources of short-wave infrared illumination include Xenon arc lamps. However, Xenon arc lamps are of much higher color temperature and, therefore, emit most of their energy in the visible region of the spectrum. Other light sources with illumination in the desired spectral range might be used as well. The proposed scanning illuminator can also be implemented with other filaments and/or tubes that emit preferentially in other parts of the spectrum, including ultra-violet, visible, near-infrared, mid-wave infrared, and long-wave infrared. Such light sources may be useful, for example, with multispectral optical sensors designed for detection of other gases, liquids, emulsions, powders, and solids.

In principle, one can use an array of carbon tube lamps arranged around a site, in order to completely illuminate the site, whereby one could then use the optical gas sensor to image the site and inspect for gaseous emissions. However, it is often not practical to illuminate an entire site with short-wave infrared light, as it requires electrical power and lighting fixtures around the site. It is also not practical to illuminate an entire site using battery-powered illuminators, as the power consumption is excessive. A practical implementation allows the use of an illuminator that is localized near the sensor, and may be transported together with the sensor around a site during an inspection, or mounted upon a mast together with the sensor so that it may overlook a fixed site, or mounted upon a vehicle together with the sensor so that it may be transported from site to site and operate while located on the vehicle (at rest, or possibly while the vehicle is in motion). A preferred implementation allows the short-wave infrared illumination (i) to be projected as a structured light pattern (e.g., a structured beam of illumination) that is well matched to the sensor instantaneous-field-of-view (ifov), and (ii) to be scanned across the site in synchrony with the scanning sensor. This synchronous scanning is particularly advantageous for a battery-powered illuminator, as it projects the light only where it is needed at any given moment to allow the sensor to detect the possible presence of gaseous emissions without wasting energy to illuminate portions of a site that are not being addressed by the sensor at the given moment. Moreover, using a vertically or radially projected light stripe of illumination that sweeps across a scene is well suited for inspecting objects or a ground surface using a sensor with a scan pattern well matched (e.g., synchronized) to the sweeping motion of the projected stripe.

The systems and methods described herein are useful in detecting, localizing, imaging, and quantifying natural gas leaks from components along the entire gas supply chain, from the well head to compressors, transmission pipelines, gate stations, and underground distribution networks. The systems and methods described herein have also been shown to be useful in detecting liquid oil spills on land, sand, seawater, and sea ice. Therefore, certain embodiments of the systems and methods described herein can be used to detect oil emulsions at sea and tar balls on beach. Certain embodiments of the systems described herein are suitable for packaging in the form of hand-portable leak inspection sensor-illuminator systems, installed or relocatable fixed-site monitoring sensor-illuminator systems, relocatable work-site safety sensor-illuminator systems, and truck-mounted (or airborne) area surveying sensor-illuminator systems, each of which may utilize small numbers of short-wave infrared detectors and spectral filters in a scanning configuration that is synchronized with a scanning structured beam of illumination.

A. Systems for Obtaining a Multispectral Absorption Image of a Scene i. System with Independently Scanned Illuminator and Optical Sensor FIG. 1A depicts an illustrative embodiment of a system 100 for obtaining a multispectral absorption image of a scene using a structured illumination beam synchronized with an instantaneous field of view (ifov) of an optical sensor 106. As shown in FIG. 1A, the system includes an illumination source 102 (e.g., illuminator), which is aligned and operable to produce a structured illumination beam. The structured illumination beam has a first beam size along a first beam axis that is greater than (e.g., by a factor of 10 to 100 times) an extent of the ifov of the optical sensor 106. In certain embodiments, the structured illumination beam is approximately shaped as a rectangular stripe. In certain embodiments, the structured beam of illumination produced by illumination source 102 comprises light having wavelengths within a short-wave infrared spectral range (e.g., light having wavelengths ranging from approximately 1 to 2.5 microns). In certain embodiments, the illumination source comprises one or more emitters of light having wavelengths within the short-wave infrared spectral range. For example, the emitter may have a color temperature of approximately 1000 to 1500° C. The emitter may, for example, be a carbon or tungsten filament. As described more below, in certain embodiments, the structured illumination beam is structured to compensate for dilution of projected power with distance from the source. For example, one or more reflectors or lenses may be used to structure the structured illumination beam and/or the illumination source may include a plurality of emitters, each emitting at a different power level and arranged to compensate for the dilution of projected power.

The system 100 also includes a beam scanner 104 aligned and operable to scan the structured illumination beam across an imaged scene. The illumination beam is scanned in a direction that is substantially orthogonal to the first beam axis. For example, the beam scanner 104 may be a rotational stage to which the illumination source 102 is mechanically coupled. As used herein, the term "scanning illuminator" is sometimes used to refer to an illumination source that is mechanically coupled to a beam scanner.

Still referring to FIG. 1A, system 100 also includes an optical sensor comprising one or more detectors. Illustrative examples of the one or more detectors are described herein with respect to FIGS. 13A, 13B, 14A, 14B, 15A, and 15B. In certain embodiments, the one or more detectors are responsive to light having a wavelength within the shortwave infrared spectral range (e.g., ranging from approximately 1.0 to 2.5 microns). In other embodiments, at least one of the one or more detectors is responsive to light from other spectral regions (e.g., ultra-violet or visible or thermal infrared) associated, for example, with the detection of hydrocarbons or toxins in gaseous or non-gaseous states, including liquids, emulsions, powders, and solids. In certain embodiments, optical sensor 106 comprises one or more spectral filters, each transmissive to light within a primarily different spectral range. Optical sensor 106 is aligned and operable to capture light from (e.g., emitted and/or reflected by objects within) an imaged scene within an instantaneous field of view (ifov) and direct the captured light, for detection, onto the one or more detectors. As used herein, the term "instantaneous field of view" (ifov) refers to a spatial extent that is observed by a detector of an optical sensor at a given moment in time or when the optical sensor is in a given configuration. For example, an ifov may be an angle (i.e., a solid angle) corresponding to the extent of a scene that is observed by a detector of an optical sensor at a given time. In the context of a multispectral detector array, an ifov may be an angle (i.e., a solid angle) corresponding to the extent of a scene that is observed by a multispectral detector array of an optical sensor at a given time.

System 100 also includes an optical sensor scanner 108 aligned and operable to scan the ifov of the optical sensor along a first scan axis (e.g., a fast axis) and a second scan axis (e.g., a slow axis), so as to raster scan the ifov across a scene and thereby detect light from a plurality of sampled locations within the scene. Each location within the scene corresponds to a particular position of the ifov within the raster scan. The scan is performed such that the first scan axis is substantially parallel to the first beam axis and the second scan axis is substantially parallel to the illumination scan direction. Moreover, optical sensor scanner 108 is operable to scan the ifov along the first scan axis sufficiently fast such that at least one scan of the ifov across an extent of a projection of the first beam size can be completed while maintaining overlap between the ifov and the structured illumination beam as the structured illumination beam is scanned. In order to maintain overlap between the ifov and the structured illumination beam, the optical sensor scanner 108 and beam scanner 104 are synchronized and aligned.

System 100 also includes a processor and memory 110. The memory includes instructions stored which are executed by the processor, causing the processor to retrieve and/or access data corresponding to the detected light for each of the sampled locations. For each of at least a portion of the plurality of sampled locations, the processor uses the detected light at the sampled location to determine a corresponding level of absorption for each of one or more spectral bands, thereby obtaining a multispectral absorption image of the scene. For example, the resulting multispectral absorption image may comprise a plurality of pixels, each corresponding to a particular set of one or more sampled location and having one or more intensity values, where each intensity value is based on a determined level of absorption at a particular spectral band of the one or more spectral bands. In certain embodiments, at least one of the one or more spectral bands is associated with a hydrocarbon compound of interest (e.g., methane, ethane, propane, or butane). A spectral band associated with a hydrocarbon compound of interest may include one or more absorption lines of the hydrocarbon compound of interest. For example, the spectral band associated with a hydrocarbon compound of interest may span approximately 100 nanometers or more.

Figure 1B:
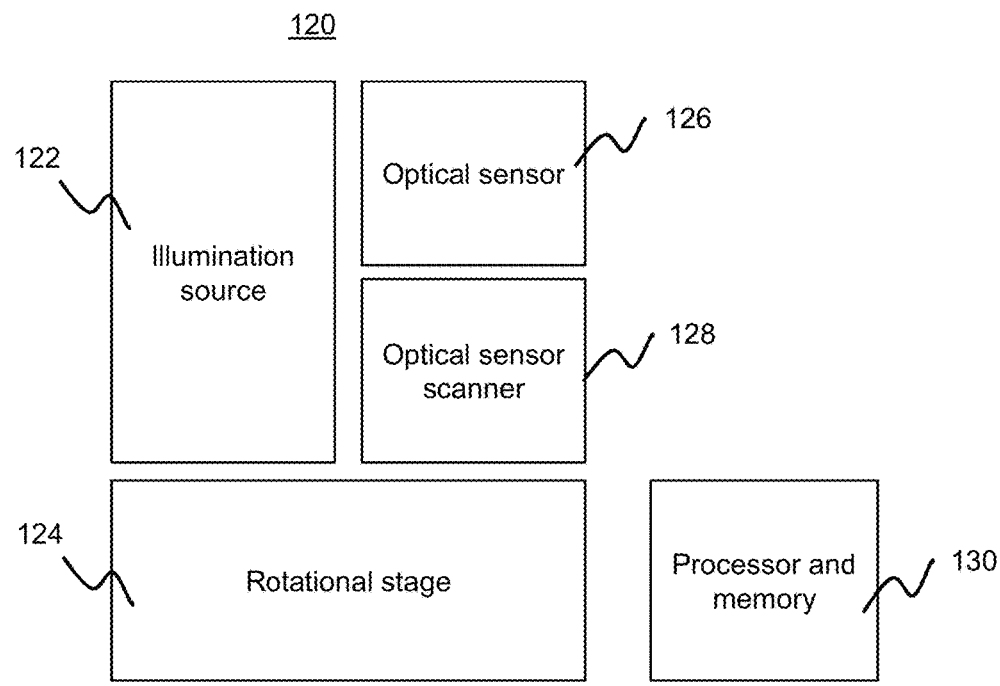
FIG. 1B is a block diagram of a system for obtaining a multispectral absorption image of a scene using a structured illumination beam produced by an illumination source mechanically coupled to a scanning optical sensor, according to an illustrative embodiment.

As described more below, system 100 is configured to maintain overlap between the ifov of the optical sensor and the structured illumination beam of the illumination source. In certain embodiments, this is achieved by synchronizing and aligning the optical sensor scanner 108 and beam scanner 104 such that (i) scanning the ifov along the first scan axis (e.g., fast scan axis) scans the ifov in a direction along the first beam axis and across a region of the scene illuminated by the structured illumination beam, and (ii) scanning the ifov along the second scan axis (e.g., slow scan axis) maintains overlap between the ifov and the structured illumination beam as it is scanned along the illumination scan direction. In other words, system 100 is configured to maintain positioning of the ifov over the region of the scene that is illuminated by the structured illumination beam as the structured illumination beam is scanned along the illumination scan direction. The first scan axis may be a fast axis of the optical sensor scanner 108 and the second scan axis may be a slow axis of the optical sensor scanner 108, such that the optical sensor scanner 108 is operable to scan the ifov along the first scan axis at a rate greater than along the second scan axis. For example, in certain embodiments, a frequency of a scan along the fast axis is 4-10 times a frequency of a scan along the slow axis. In other embodiments, a frequency of a scan along the fast axis is 10-100 times a frequency of a scan along the slow axis. In still other embodiments, a frequency of a scan along the fast axis is greater than 100 times a frequency of a scan along the slow axis.

ii. System with Illuminator and Optical Sensor Mechanically Coupled to Rotation Stage FIG. 1B is a block diagram of a system 120 for obtaining a multispectral absorption image of a scene using a structured illumination beam produced by an illumination source 122 mechanically coupled to a scanning optical sensor 126, according to an illustrative embodiment. The system includes an illumination source 122, an optical sensor 126, an optical sensor scanner 128, and a rotational stage 124 on which the illumination source 122, optical sensor 126, and optical sensor scanner 128 are mounted.

Illumination source 122 is aligned and operable to produce a structured illumination beam having a first beam size along a first beam axis. Illumination source 122 of FIG. 1B may, for example, be the same as illumination source 102, described herein with respect to FIG. 1A. Optical sensor 126 includes one or more detectors and is aligned and operable to capture light from a scene within an instantaneous field of view (ifov) and direct it, for detection, onto one or more detectors. Optical sensor scanner 128 is aligned and operable to scan the ifov of the optical sensor along a first scan axis (e.g., a fast scan axis) that is substantially parallel to the first beam axis.

Rotational stage 124, on which the illumination source, optical sensor, and optical sensor scanner are mounted, is aligned such that at least a portion of the first scan axis is substantially coincident with the first beam axis. Thus, scanning of the ifov along the first scan axis scans the ifov in a direction along the first beam axis, overlapping with the structured illumination beam (e.g., over a region of the scene illuminated by the structured illumination beam). Rotational stage 124 is operable to rotate about a rotational axis that is substantially parallel to the first scan axis and/or the first beam axis, such that (i) rotation of the rotational stage scans the structured illumination beam and ifov together in a second scan direction that is substantially orthogonal to the first scan axis, and (ii) scanning of the ifov by the optical scanner 128 in combination with rotation of the rotational stage 124 raster scans the ifov across the scene. Thus, light is detected from a plurality of sampled locations within the scene, each corresponding to a particular position of the ifov within the raster scan.

System 120 also includes a processor and memory 130 with instructions stored thereon. The instructions, when executed by the processor, cause the processor to retrieve and/or access data corresponding to the detected light for each of the sampled locations, and obtain a multispectral absorption image of the scene (e.g., as described above with respect to FIG. 1A).

iii. Other Embodiments of Scanning Sensors

FIGS. 1C and 1D illustrate various scanning, illumination, optical sensor, and processing components of the systems described herein. FIG. 1C is a block diagram of a multispectral imaging system 140 that does not include an illumination source. Beginning with the SWIR camera (SWIR), it consists of one or more of the SWIR photo-detector arrays (e.g., linear, dual-linear, or two-dimensional, e.g., as shown in FIGS. 13A, 13B, 14A, 14B. 15A, and 15B) together with its corresponding read-out circuitry and video timing circuitry. This SWIR camera has a SWIR lens (L) that is transmissive to at least the spectral range spanning the wavelengths of interest to sense the hydrocarbon features, approximately 1.0 through 2.5 microns. Positioned between the SWIR lens (L) and the SWIR camera (SWIR) may be a spectral filter array positioner (F) which may include a motor and/or mechanical fixture to properly locate the correct filter(s) in front of the photo-detector array(s) during the exposure of each frame. This combination of SWIR detector array plus filter array corresponds to the various embodiments as shown, e.g., in FIGS. 13A, 13B, 14A, 14B, 15A, and 15B. The SWIR imaging sub-system also includes a scanning mirror (SM) that sweeps the scene across the field-of-regard. The scanning mirror (SM) is typically a one-dimensional scanner that sweeps in a direction perpendicular to the orientation of the filters positioned over one-dimensional detector arrays or the stripes over two-dimensional detector arrays. An electronic driver (D) controls the scanning mirror (SM). Synchronization between the scanning mirror (SM), filter positioner (F), and SWIR camera (SWIR) is provided by a micro-controller (C). Two-dimensional image assembly is performed on a microprocessor (P1).

Figure 2A:
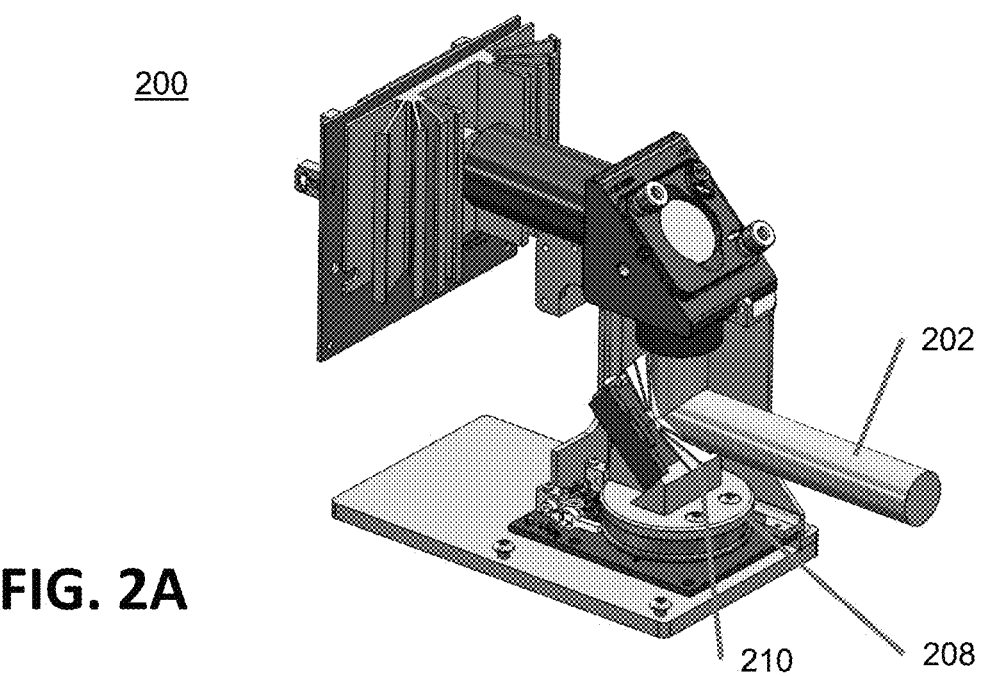
FIG. 2A is a solid model drawing of a scanning multi spectral short-wave infrared optical sensor, according to an illustrative embodiment.
Figure 2B:
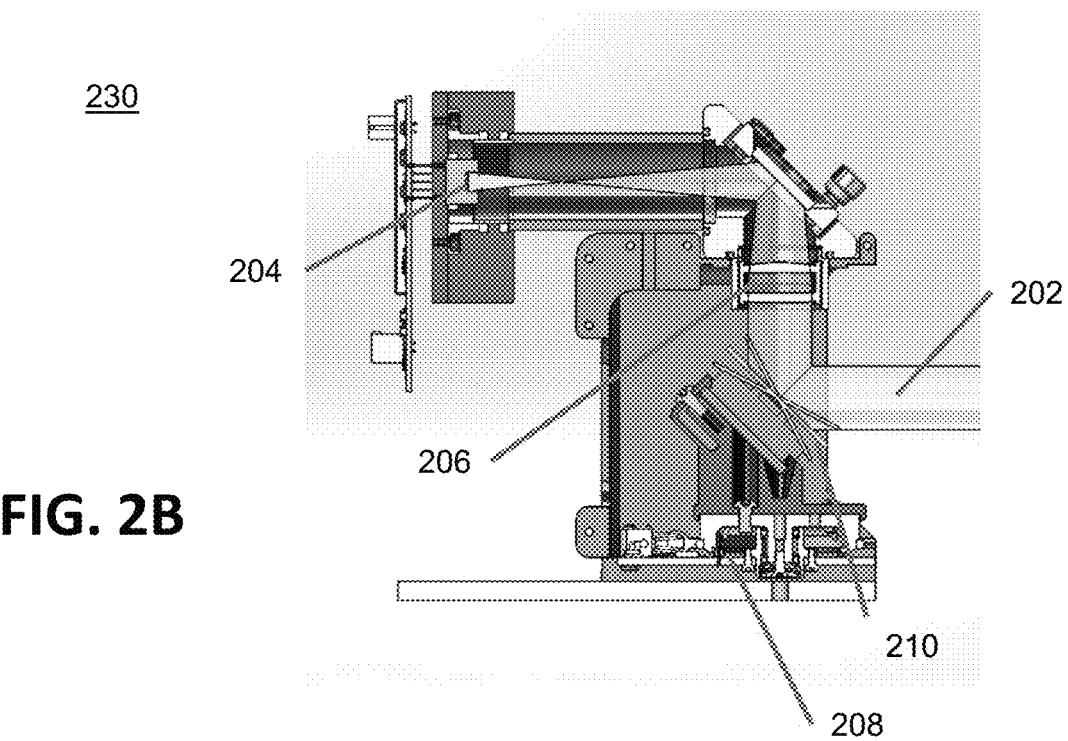
FIG. 2B is a diagram of a cross-section of a scanning multi spectral short-wave infrared optical sensor, according to an illustrative embodiment.

FIG. 1D is a block diagram of a multispectral imaging system 150 which includes an illumination source (Lum), according to another illustrative embodiment. In this illustrative embodiment, the discrete photo-detectors and spectral filter mosaic (SFM), e.g., of FIG. 14B form a single multispectral pixel by means of a lens (L), and this sensor and illuminator (Lum) are mounted on a pan-tilt unit (PTU) controlled by micro-controller (C2). Two-dimensional imagery is created by raster scanning across a desired, and possibly variable, field-of-regard. In order to create imagery of higher resolution than that obtained directly by scanning this sensor with its own narrow ifov, it may be useful to employ spatial over-sampling in combination with super-resolution image processing. Two-dimensional scanning can be accomplished using the PTU, or in a compact configuration, for example, by a pair of scanning mirrors or a pair of rotating prisms. Two-dimensional imaging can also be achieved using a single scanning mirror combined with physical movement of the imaging sensor (e.g., translation or rotation in a direction perpendicular to the scan mirror motion) such as by mounting the sensor upon a moving platform (e.g., truck-mounted, airborne, rail-mounted) or rotating the sensor in a mast-mounted configuration (e.g., as depicted in FIG. 3). Moreover, two-dimensional imaging can be achieved using a single scanning mirror (which scans along a fast axis) which itself is mounted upon a rotation stage that rotates the scanning mirror in a direction that is orthogonal to its fast scanning axis. This arrangement of optical scanner and multispectral detector array is shown in FIGS. 2A and 2B.

Each imaging system of FIGS. 1C and 1D may also include one or more visible color (e.g., RGB) or black and white cameras, laser range finder (LRF) to measure distance from the sensor to a detected leak and/or surface, global positioning system (GPS) sensor to determine sensor location (e.g., and indirectly leak location), inertial measurement unit (IMU) to sense linear and rotational accelerations including direction of gravity, magnetic sensor (Mag) to sense the earth's magnetic field acting as a compass, and/or weather sensors (Wx) to relay local atmospheric conditions including wind speed and direction, all of which is packaged together with one or more processors (P1, P2). In order to optically register the visible imagery with the SWIR imagery and resulting gas absorption imagery, as shown in FIG. 1C, a beam splitter (BS) is incorporated that is preferably dichroic, such that the incident light along the line-of-sight (LOS) is mostly transmitted through the beam splitter for visible wavelengths (approximately 0.4-0.7 microns) and mostly reflected for SWIR wavelengths (approximately 1.0-2.5 microns). The reflected SWIR light is subsequently reflected by the scanning mirror (SM) towards the SWIR lens (L) that focuses this light onto the SWIR camera (SWIR) behind the spectral filter assembly (F). Alternatively, as shown in FIG. 1D, in the absence of a beam splitter, the measured range to possibly each SWIR sample can be used to correct the parallax offset between that SWIR sample and its corresponding location in the visible RGB image, for example, using the known spacing of the SWIR, RGB, and LRF sensors.

As shown in FIGS. 1C and 1D, one processor (P1) may be associated with the multispectral SWIR camera and is responsible for real-time or near real-time processing of the SWIR multispectral data to create gas absorption imagery. A separate processor (P2) may have a path for accepting the visible camera (RGB) imagery and triggers the other low-bandwidth sensors (e.g., LRF, GPS. IMU, and Mag). This processor (P2) may also communicate wirelessly (or via wire) with an external weather sensor (Wx) and a graphical user interface (GUI) implemented on, for example, a touch-screen tablet computer. The tablet, in turn, provides wireless access to an Ethernet or data cloud (E/C), which in turn can be accessed by a remote personal computer or other computing device (PC). This arrangement allows remote (PC) access and control of one or more gas imaging sensor systems. Finally, an artificial illuminator (Lum), as shown in FIG. 1D and described herein, may be controlled by a micro-controller (C2) and incorporated to allow gas imaging in the absence of sufficient sunlight or for indoor locations.

Alternative implementations are possible, such as, for example (but not limited to), a configuration with (i) the display or the controls or the complete user interface physically attached to the imaging device; (ii) the display or the controls or the complete user interface physically remote from the imaging device; (iii) the user interface implemented with physical knobs, buttons, sliders, dials, selectors or similar on the imaging device or separate from it; (iv) the user interface implemented with digital representations of knobs, buttons, sliders, dials or similar using a display where this display can be either physically attached to the imaging device or connected by wired or wireless means; (v) a combination of physical and digital user interface described above; (vi) processors P1 and P2 combined into a single processor or their functions distributed over multiple processors; (vii) some or all of the low-bandwidth sensors being integrated into (a) the imaging device, (b) into a separate unit, or (c) into a display unit; (viii) some or all of a single set of low-bandwidth sensors being connected to one or several processors that is (are) providing data for use by multiple imaging sensor systems.

The various sensor embodiments described above can be operated in many different modes. In one mode the data gathered from the sensor is analyzed by a processor and used for automatic analysis and decisions (such as triggering of an alarm signal or different operating mode, because a certain limit of gas detection or leak rate is exceeded) by the processor without being displayed in real-time or near real-time on a display. In another mode an image of the received data can be shown on a display (for example for monitoring by a human operator) however no real-time analysis like gas quantification is performed. In a third mode an image is displayed and automatic gas quantification is performed, and significant results are automatically stored or sent to remote locations. Other combinations and modes of operation are possible as well, for example in conjunction with the use of low-bandwidth sensors like range and weather sensors.

Elements of the optical sensors and illumination sources described herein may be combined to create scanning multispectral imaging systems of the present disclosure, an illustrative example of which is diagrams 200 and 230 shown in FIGS. 2A and 2B, respectively. The sensor has an instantaneous-field-of-view (bfv) 202 determined by the size of the individual photodetectors 204 in a multispectral detector array and the focal length of the lens 206, which are illustrated in cross-section in FIG. 2B. In particular, the sensor ifov is the combination of all of the individual photodetectors's individual ifov's. For example, for 1 mm diameter detectors and a 100 mm focal length lens, the sensed ifov of a single detector is 10 milliradians. Thus, at a range of 10 meters from the sensor, this single detector ifov covers a spot size of 10 centimeters, and the spot size scales linearly with range. For an array of spectrally filtered detectors, as shown, e.g., in FIGS. 14B, 15A, and 15B, the sensor ifov is determined by the array diameter (e.g., 6 mm) and the lens focal length (e.g., 100 mm) (e.g., resulting in an ifov of 60 milliradians). In this embodiment, the sensor ifov is rapidly scanned along the vertical direction by means of a resonant vibrating mirror 210, as shown in FIG. 2A and in cross-section in FIG. 2B. In this embodiment, the sensor ifov is slowly scanned along the horizontal direction by means of a rotation stage 208 upon which the resonant mirror 210 is mounted, as shown in FIG. 2A.

Typically, the vertical scan occurs with a frequency of approximately 10 to 10) times that of the horizontal scan, though other options like 4 to 10 times or more than 100 times are feasible as well. In order to increase the sensed signal-to-noise ratio, a vertical scan can be repeated multiple times before rotating (i.e., stepping) the vibrating mirror to the next position of the horizontal scan. In some embodiments, the horizontal scan is repeated multiple times, averaging the scanned imagery together in order to increase the sensed signal-to-noise ratio. The overall field-of-regard 262 of the scanning sensor is illustrated in diagram 260 shown in FIG. 2C and may be manually or electronically adjustable in both its vertical and horizontal extent. A practical embodiment is shown in which the vertical field-of-regard is 60° and the horizontal field-of-regard is 90°. In other embodiments, scans are performed rapidly in the horizontal direction and slowly in the vertical direction. In other embodiments, rapid scanning in one direction is combined with slow scanning or stepping in both the horizontal and vertical direction. For example, scanning may be performed horizontally along multiple stripes of increasing range [e.g., where a first scan with a first range (e.g., from 1-10 m) at a first (lowest) illumination power is combined with a second scan at a second range (e.g., from 10-20 m) at a second (increased) illumination power].

iv. Example Scan Patterns for Optical Sensors and/or Illuminators

Figure 2C:
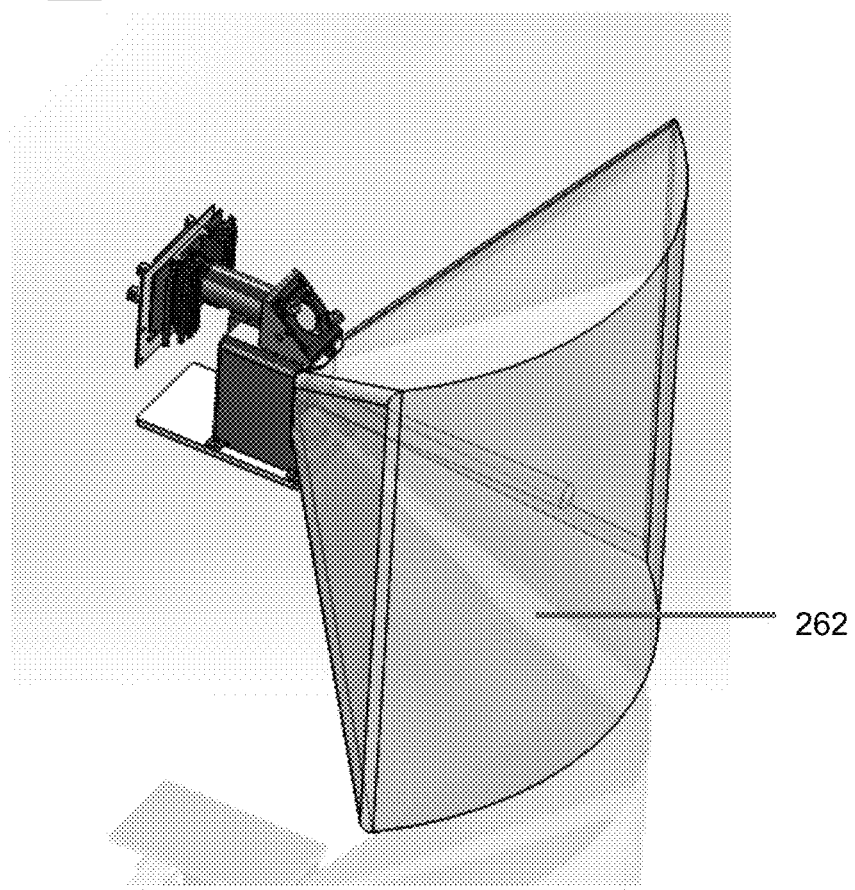
FIG. 2C is a diagram of the field-of-regard achieved with a scanning multi spectral short-wave infrared optical sensor, according to an illustrative embodiment.

With the imaging sensor system, e.g., of FIG. 1A, 1B, 1C or 1D, properly calibrated, mounted atop a mast located next to, or near, a site of interest, e.g., as illustrated in FIG. 3, the sensor can be scanned around the boundary of the site (in one embodiment, with an approximate size of 15 meters on a side) so as to create an optical sheath 320 (e.g., corresponding to a narrow region near the edge of the field-of regard 262 of the system shown in FIG. 2C) that envelops and covers the site and any equipment located upon the site. If a gas leak is present, the gas will migrate (due to buoyancy, wind, and/or diffusion) so as to cross some part of the optical sheath 320. This will result in selective absorption of the illumination within the multiple spectral bands, indicative of the particular species and amount of gas. Thus, a rapid boundary scan may be used to first detect the existence of a leak. Once so detected, a change of scan pattern may be automatically triggered. A more focused scan pattern within the optical sheath allows localization of the leak on the site. Upon localizing the leak to within a predetermined extent, the scanning sensor may automatically switch to a raster scan pattern of the area around the leak. By spatially oversampling the sensor data while scanning its ifov, a progressive-resolution image may be constructed using super-resolution processing techniques. This example sequence of imaging configurations results in a sequence of increasing resolution imagery around the leak, whereby the resolution of an image pixel may exceed the sampling resolution of the detector itself. Super-resolution image processing methods are well documented in the open literature.

In the illustrative embodiment shown in diagram 300 of FIG. 3, a system 305 comprising an optical sensor and an illuminator mounted on a pan-tilt unit is attached to a mast, for example, adjacent to a gas well pad and having the well pad 315 within a respective optical sheath 320 monitored by the system 305. As the sensor of the system 305 scans a closed boundary of the site, it creates an optical sheath 320 that envelopes the site.

Figure 4A:
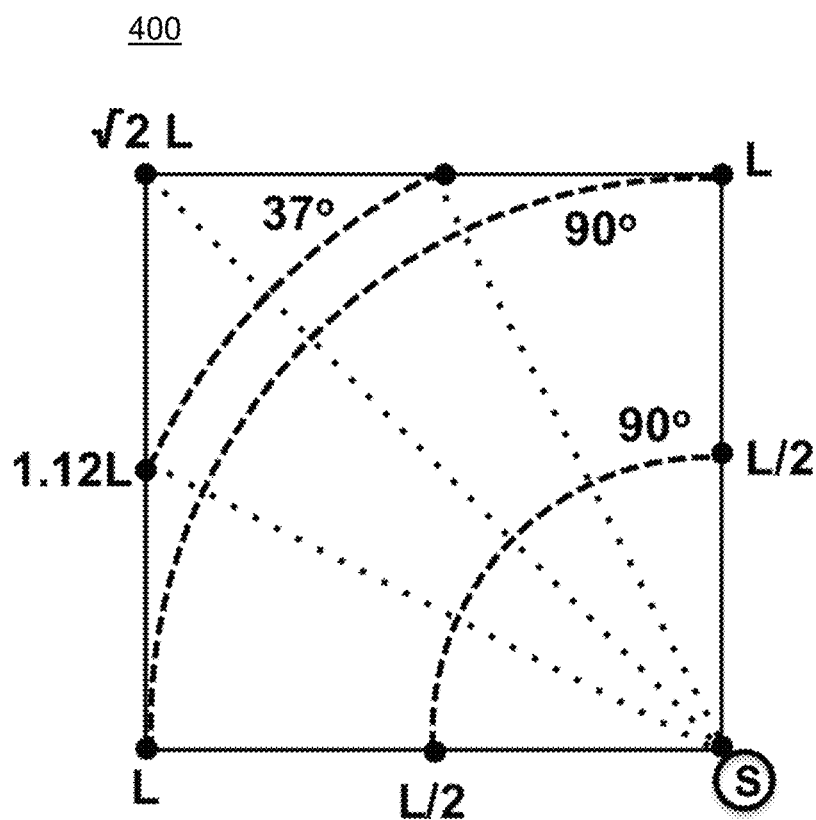
FIG. 4A is a diagram of a plan view of a square site of dimensions L×L (example L=10 meters) with a sensor S located at one corner of the site, according to an illustrative embodiment.

FIG. 4A shows a diagram 400 of a plan view of a square site, such as the gas well pad 315 of FIG. 3, having dimensions of L×L. In an exemplary, non-limiting embodiment. L equals 10 meters. The sensor S is located at one corner of the site. As the sensor pans in angle across the site in azimuth, about a vertical axis of rotation, the line of sight of the sensor traces out polar arcs on the ground plane. As the sensor tilts in elevation, about a horizontal axis of rotation, the sensor line of sight traces radial lines on the ground plane.

Figure 4B:
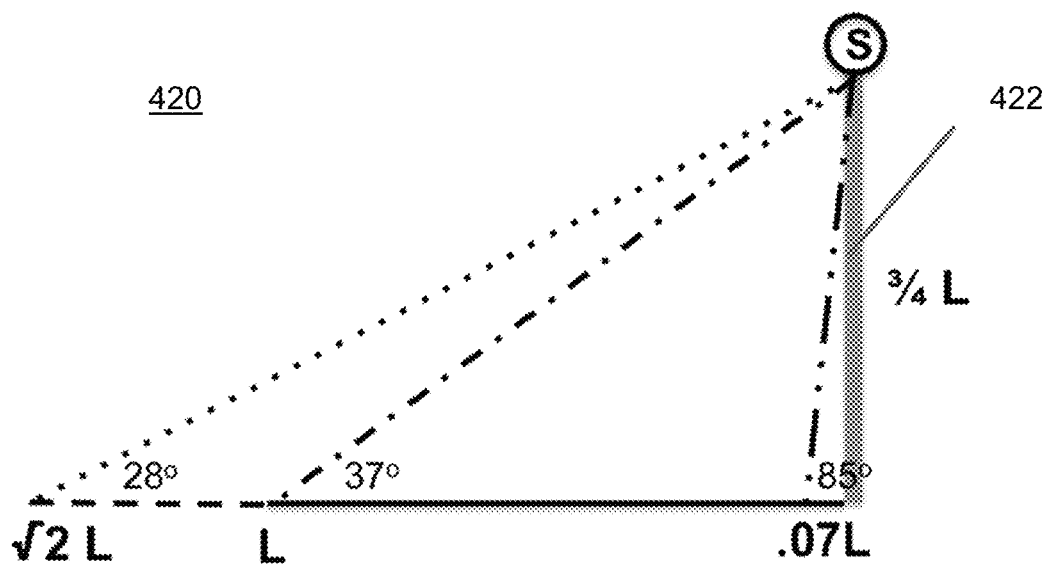
FIG. 4B is a diagram of a side view of an L×L square site, with sensor S mounted atop a mast of height ¾L located at one corner of the, according to an illustrative embodiment.

FIG. 4B shows a diagram 420 of a side view of an L×L site. The sensor S is mounted atop a mast 422 of height ¾L, disposed in one corner of the L×L site. Tilt angles relative to the horizontal are shown as rays from the sensor to various locations on the ground plane, including in the opposite corner of the site, at 28° from a horizontal plane extending from the sensor. Other exemplary rays are illustrated, including one ray intersecting the ground plane a distance L in the ground plane from the mast and 37° from horizontal, and one ray intersecting the ground plane a distance 0.07 L in the ground plane from the mast and 85° from horizontal.

Figure 5:
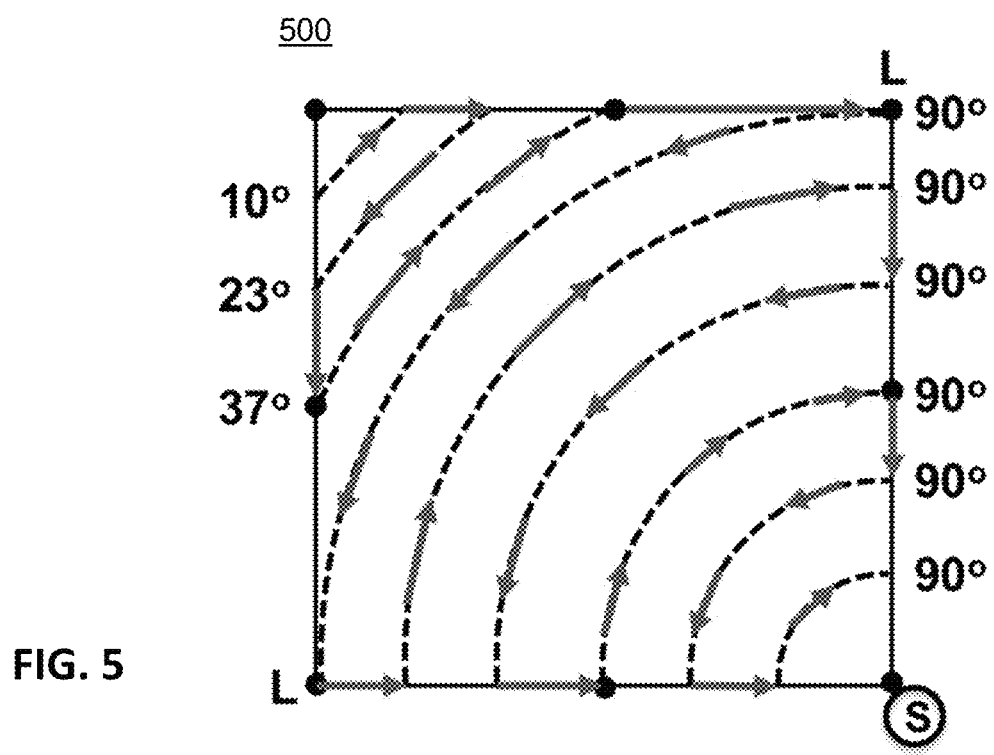
FIG. 5 is a diagram of a plan view of a square site covered by a polar coordinate raster scan pattern relative to sensor S, according to an illustrative embodiment.

FIG. 5 shows a diagram 500 of a square site, covered by a polar coordinate raster scan pattern relative to the sensor S, in plan view. This raster scan pattern provides full coverage over the site and is suitable for monitoring gas emissions across the illustrated site. Such a polar scan provides multispectral imagery that can be super-resolved into high-resolution imagery for the detection and quantification of emissions from anywhere within the site. Various mechanisms and configurations thereof may be used to accomplish optical scanning (e.g., as described above) and can be combined in numerous ways to realize the boundary scan and optical sheath 320 of FIG. 3, the leak localization scan, and the raster scan over an entire site or over an area of interest (e.g., a region around a localized leak).

Figure 6A:
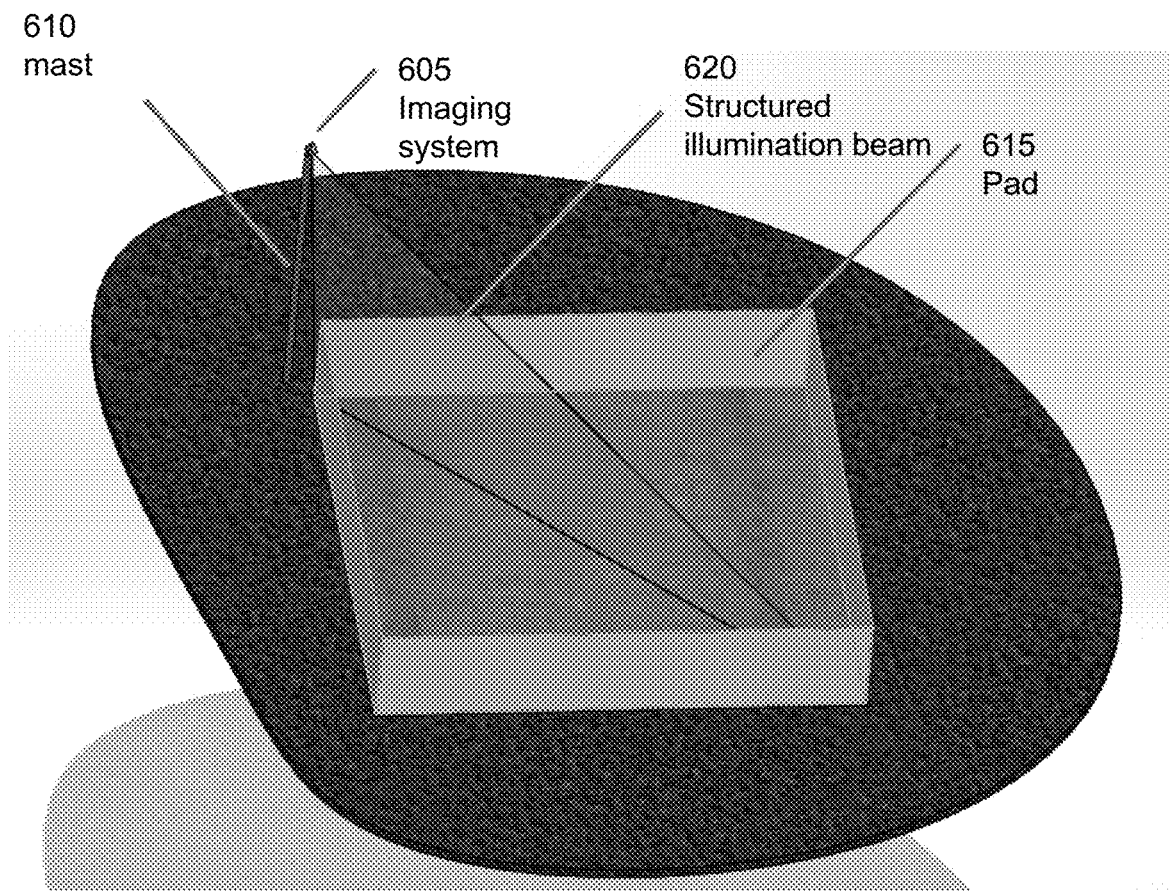
FIG. 6A is a diagram of the illumination and sensing geometry of an elevated system overlooking a site of interest, according to an illustrative embodiment.
Figure 6B:
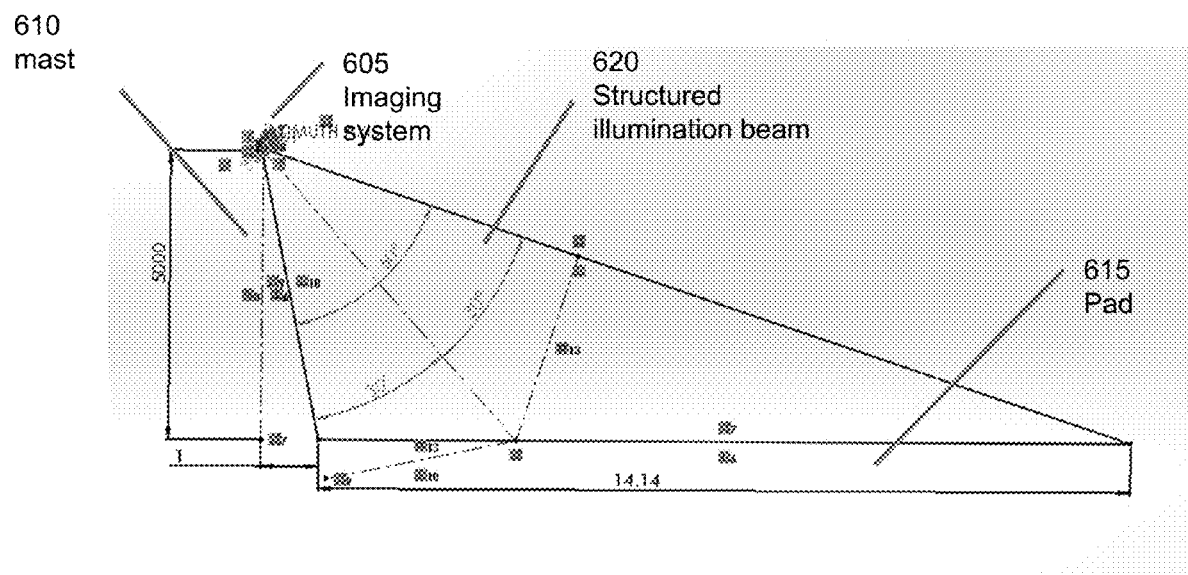
FIG. 6B is a diagram of the illumination and sensing geometry of a 5 m-elevated system overlooking a 10 m×10 m site along its diagonal, according to an illustrative embodiment.

The systems described herein can be utilized in different imaging geometries (e.g., and/or with different scan patterns), such that a preferred implementation requires different distributions of projected light. When used in a hand-portable inspection mode, it is often desired to view objects at a similar height to the imaging system. Therefore, the light may be projected outwards onto an approximately vertical target. In this embodiment, it is preferred that the illuminator projects a vertical stripe of approximately uniformly distributed power with a beam width that covers the spot size sampled by the sensor ifov of the sensor over the intended operating range. When the system is used from an elevated position overlooking a site, the light is to be projected obliquely onto an approximately horizontal ground plane upon which various structures may be located. An illustrative example of this configuration is shown in FIGS. 6A and 6B, where the sensor-illuminator system 605 is mounted atop a 5-meter tall mast 610 located near the vertex of a 10-meter square pad 615 (e.g., a well pad or compressor pad) and oriented downwards at an oblique angle such that the vertical field-of-regard of the scanned sensor covers the entire diagonal extent of the site. In this embodiment, the illuminator will project a structured beam of illumination 620 as a radial stripe on the ground that is scanned horizontally (i.e., azimuthally) across approximately 90° from one side of the site to the other.

Figure 6C:
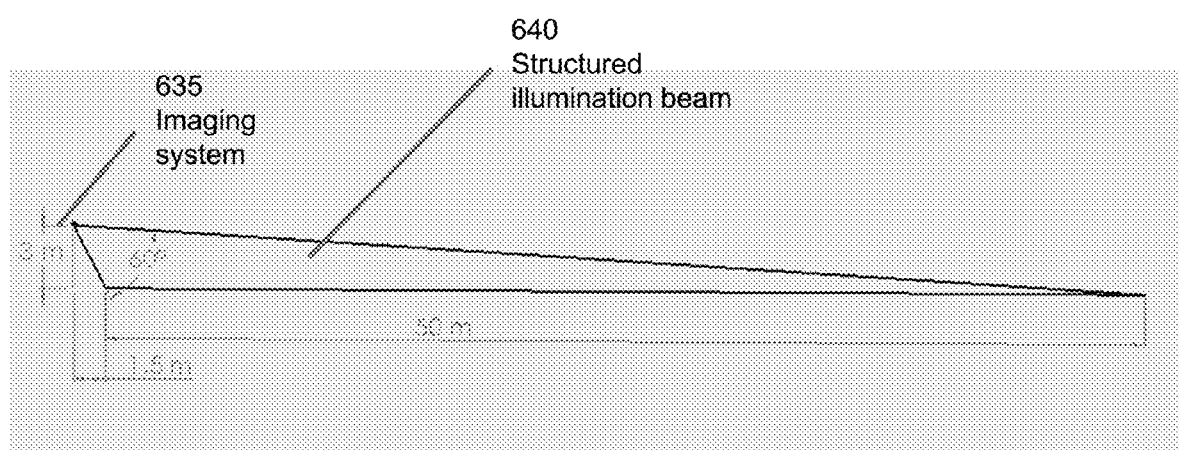
FIG. 6C is a diagram of the illumination and sensing geometry of a 3 m-elevated system overlooking an area ranging from 1.5 m out to 50 m, according to an illustrative embodiment.

In certain embodiments, it is desirable for the power projected radially along the narrow beam be non-uniform, increasing in intensity with range so that upon reflection from the ground, the light reaching the sensor is of similar power. Therefore, in certain embodiments (e.g., when the projected beam is not well collimated), the projected beam is structured to compensate for the inverse-square dilution of projected power. The dilution of projected power may be compensated for by augmenting the reflective optics of the illuminator with a Fresnel prismatic lens at its exit aperture. FIG. 6C illustrates an extended version of this sensing geometry, where the sensor-illuminator system 635 is elevated 3 meters above the ground (e.g., vehicle-mounted) to project a structured beam of illumination 640 to a distance of 50 m, while sensing an area extending out to 50 meters ground distance. In this embodiment, it is preferred to have the Fresnel lens also create a diverging beam from the approximately collimated beam produced by the reflective optics, so that the beam divergence approximately matches the ifov of the sensor optics. This facilitates adequate illumination of distant spots on the ground without wasting illumination power for spots at close and intermediate ranges. In certain embodiments, large range imaging such as that described above (e.g., imaging out to 50 meters) is performed by scanning the site in stripes of increasing range, while adjusting the power projected by the illuminator as range is increased.

Though a preferred embodiment is one in which the structured illumination beam is a structured light stripe that is vertical (or radial) and is scanned horizontally across a site, as this is well-matched to the sensor scanning mechanisms described herein, it is also possible to rotate this scanning pattern by 90° in order to use a projected horizontal stripe that is swept vertically (or radially) across a site. Indeed, a narrow beam may be scanned in any possible direction across a scene, as long as the sensor scan is synchronized to rapidly scan along the projected beam and slowly scan together with the beam across the scene.

Although the sensors described herein are generally able to scan in two-dimensions, rapidly in the vertical direction and slowly in the horizontal direction, it may at times be preferable to have a sensor scan only in the vertical direction along the projected light stripe, and rotate horizontally the combined illuminator and sensor system, rather than independently scanning horizontally the illuminator and sensor, requiring a means to synchronize their separate scans.

v. Example Illuminators

Figure 7A:
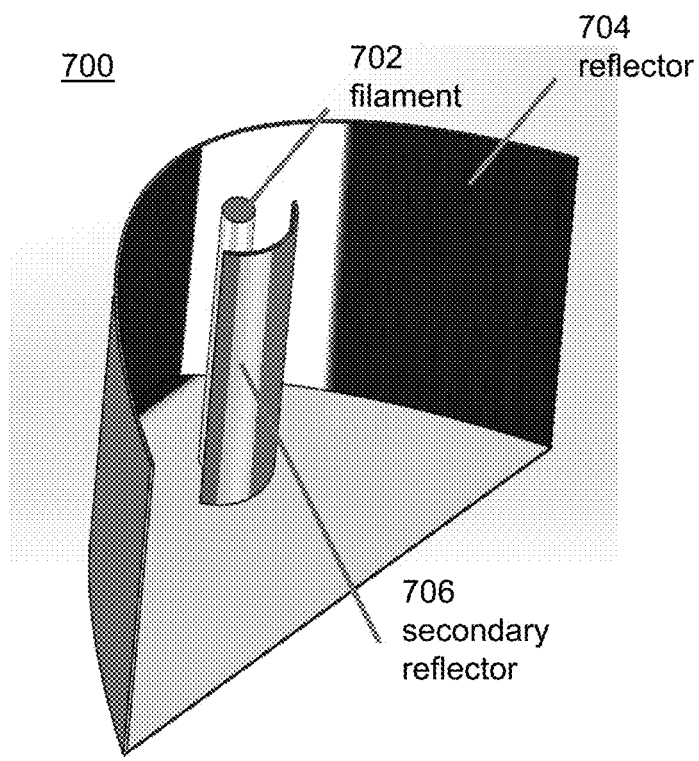
FIG. 7A is a diagram of a carbon infrared emitter tube located at the focus of a parabolic cylindrical reflector, and at the center of a secondary circular cylindrical reflector, according to an illustrative embodiment.
Figure 7B:
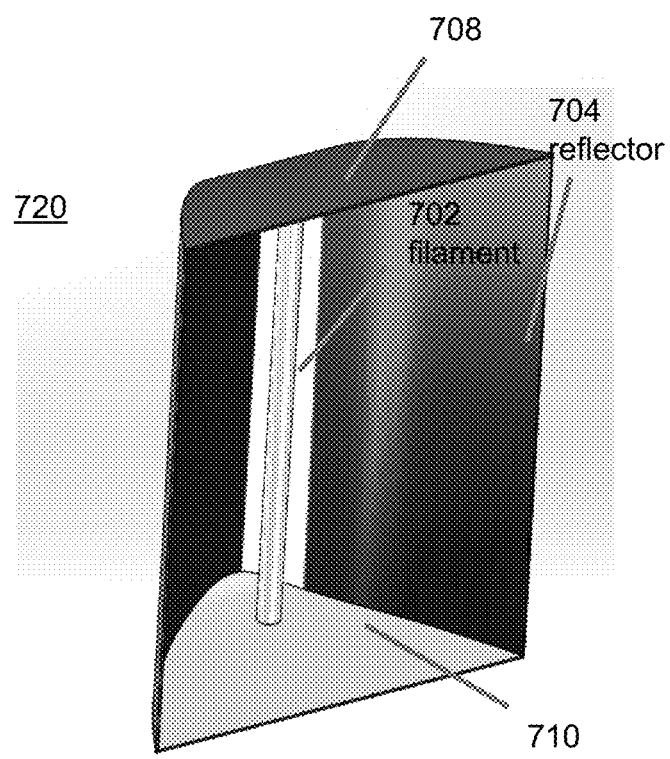
FIG. 7B is a diagram of the emitter and primary parabolic reflector of FIG. 7A, with top and bottom reflectors, according to an illustrative embodiment.

Diagrams 700 and 720 of FIGS. 7A and 7B, respectively, illustrate the reflective elements of an illustrative embodiment of the illuminator (e.g., illumination source) described herein. An emitter filament 702, such as carbon or tungsten, is contained in a cylindrical tube that is located along the focal axis of a parabolic cylinder reflector 704. The parabolic reflector 704 serves as the primary reflector that will collimate rays emitted from the filament that project onto the parabola. In certain embodiments, reflector 704 is not parabolic in shape. For example, alternatives to parabolic-shaped reflectors are well known, and may be used for certain extended illumination sources (e.g., coiled filaments and multiple filaments). In certain embodiments, a secondary reflector 706 in the form of a circular cylinder arc, the focal axis of which coincides with the focal axis of the parabola, is located on the opposite side of the filament 702 from the parabola's vertex. A secondary reflector 706 can be useful because it may increase the projected irradiance onto a distant target. However, in certain embodiments, a secondary reflector is not used (e.g., as shown in FIG. 7B). The angular extent of this circular reflector is chosen to prevent emitted light from exiting forward without first reflecting off the parabola. Thus, rays projected from the filament towards the circular reflector are reflected back through the common focal axis and onto the parabolic reflector. Ideally, all rays exit from this illuminator as a collimated narrow beam whose width is determined by the width of the exit aperture of the parabolic reflector. However, due to the finite size of the emitting filament and the glass tube that encloses the filament, rays will be refracted into non-ideal directions, and this will result in a non-perfectly collimated beam. Such a non-perfectly collimated beam may diverge by a small angle, leading to dilution of projected illumination power with range. Additionally, those rays that are emitted in a non-radial direction from the tube will reflect off the top and bottom of the illuminator. Thus, in certain embodiments, it is desirable to shape the top 708 and bottom 710 reflective surfaces (e.g., as shown in FIG. 7B) so as to guide the rays to be approximately parallel to those that reflect off the parabolic reflector. For example, top and bottom reflectors that assume a macro-focal parabolic geometry with respect to the ends of the emitting filament provide an effective means for redirecting this light. In order to maximize the infrared reflectivity of all interior surfaces of the illuminator, it is preferred to coat these surfaces with a gold film. Other standard infrared reflector coatings may include polished aluminum, protected aluminum, and protected silver.

Figure 7C:
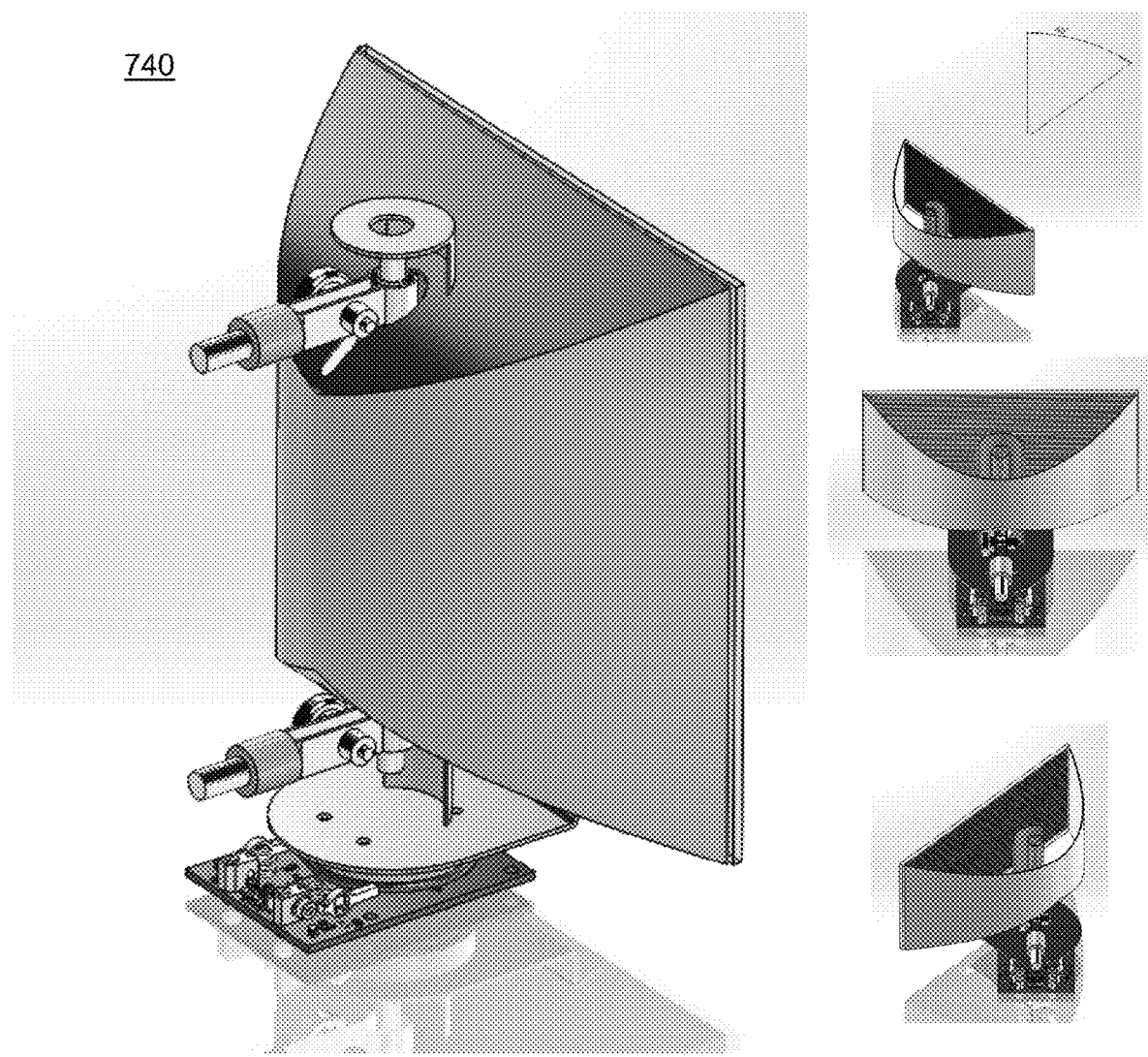
FIG. 7C is a diagram of the illuminator of FIG. 7A and FIG. 7B with reflectors mounted to a rotation stage while the emitter tube remains stationary on the axis of rotation, according to an illustrative embodiment.

The illuminator, as described above, will project a narrow nearly collimated illumination beam (e.g., a stripe) onto a vertical or horizontal surface. The sensor can rapidly sample the light reflected from the surfaces, e.g., by means of a resonant vibrating mirror (e.g., as shown in FIGS. 2A and 2B). In order to scan across the site, it is necessary that the projected light beam be scanned across the site in synchrony with the sensor ifov, which itself is accomplished by means of the rotation stage upon which the resonant mirror is mounted. This horizontal scanning of the structured illumination beam (e.g., of the projected light stripe) can be accomplished in several ways. For example, the illuminator may be rotated on a pan-tilt unit, or more simply on a rotation stage. In certain embodiments, the illuminator and sensor are mounted in vertical alignment, and both are scanned horizontally by the same mechanism (e.g., motor drive). In another embodiment, the exit beam is reflected off of a planar mirror where the mirror itself is scanned on a rotation stage. These approaches require a motor of sufficient torque and accuracy to rotate either the entire illuminator or a planar mirror at the exit aperture. In other embodiments, the primary and secondary reflectors are rotated around their common focal axis, while keeping the emitter tube stationary. The reflectors themselves can be made, for example, from a thin highly-reflective foil attached to a lightweight frame that provides structural support in the desired shape. Other reflectors known in the art can be chosen as well. An illustrative embodiment of this arrangement is shown in FIG. 7C, which depicts an illuminator with reflective elements rotated to different angles (see inset images to FIG. 7C). By keeping the weight of the reflective elements to a minimum, it is possible to employ a low-cost, highly accurate and responsive, zero backlash, piezoelectric motor driven rotation stage. Alternatively, one can use a conventional stepper motor arrangement, or a continuous movement motor, that is geared down and controlled to scan the illuminator at the proper speed. An advantage of this arrangement is that the emitter tube remains stationary and can be cooled by an air column that circulates along the tube between top and bottom reflectors, transporting heated air away from the tube and reflecting surfaces to an outer enclosure responsible for dissipating the heat into the surroundings, and preventing exchange of vapors between the exterior and interior of the enclosure. For operation in hazardous atmospheres, it is essential that the illuminator enclosure remain well below the ignition temperature of any gases that may be present in the environment; a consequence of the very gas leaks the invention aims to detect, image and quantify.

As already noted, in order to achieve similar reflected power levels from near and far range along the projected light stripe, it may be desirable to project a larger light flux to more distant locations along the stripe. This redistribution of emitted light along the vertical axis of the exit aperture can be accomplished with a set of prisms that preferentially direct light upwards as compared to outwards. Such a vertically stacked set of prisms forms a Fresnel prismatic lens. As this redirecting of light is achieved via refraction at the facets of the Fresnel lens, it is important to account for the wavelength dependent nature of refraction, to ensure that all wavelengths in the spectral range of interest are sufficiently redistributed along the projected light stripe.

Figure 8A:
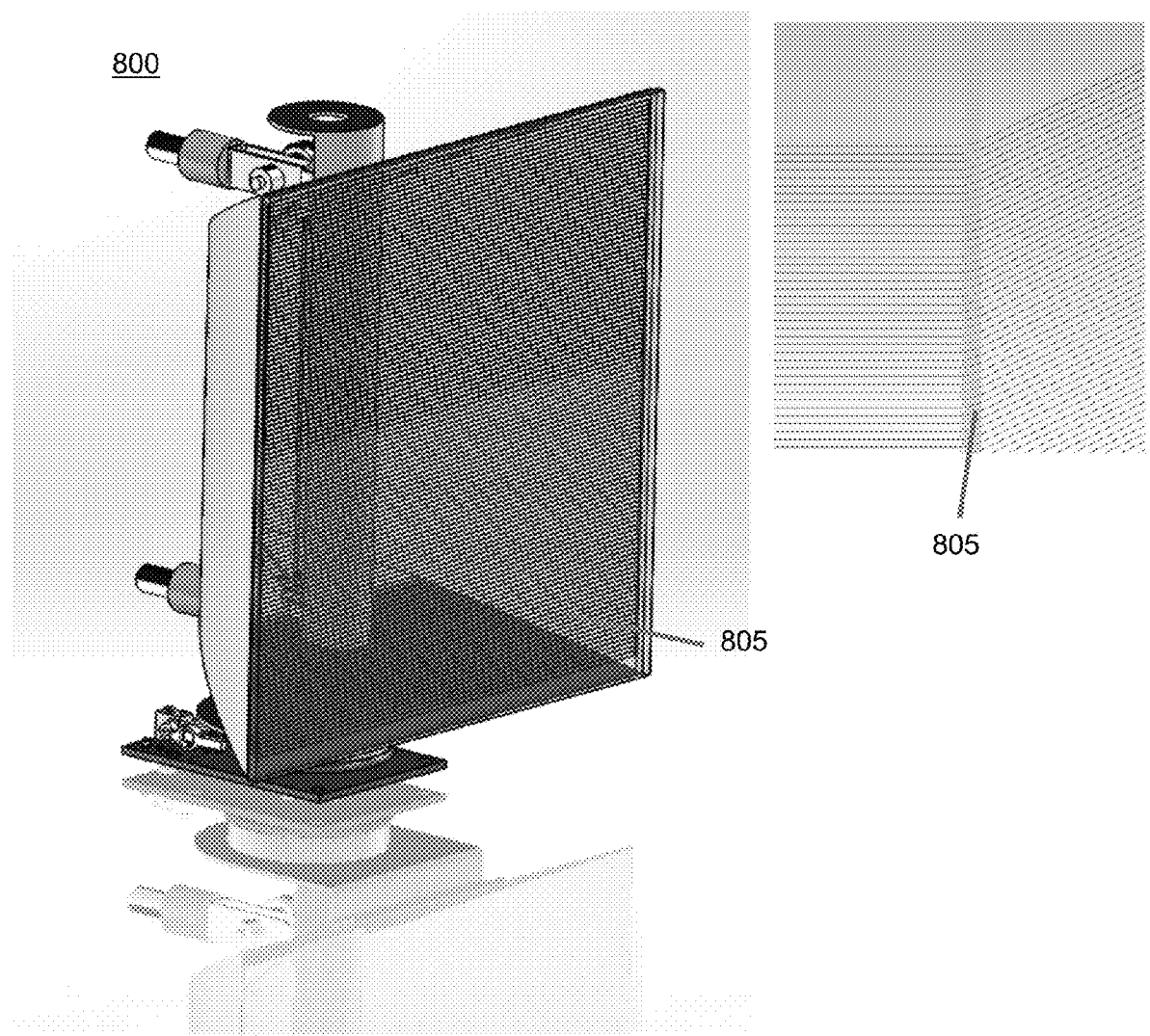
FIG. 8A is a diagram of the illuminator of FIG. 7C with a planar Fresnel prism lens at its exit aperture, according to an illustrative embodiment.
Figure 8B:
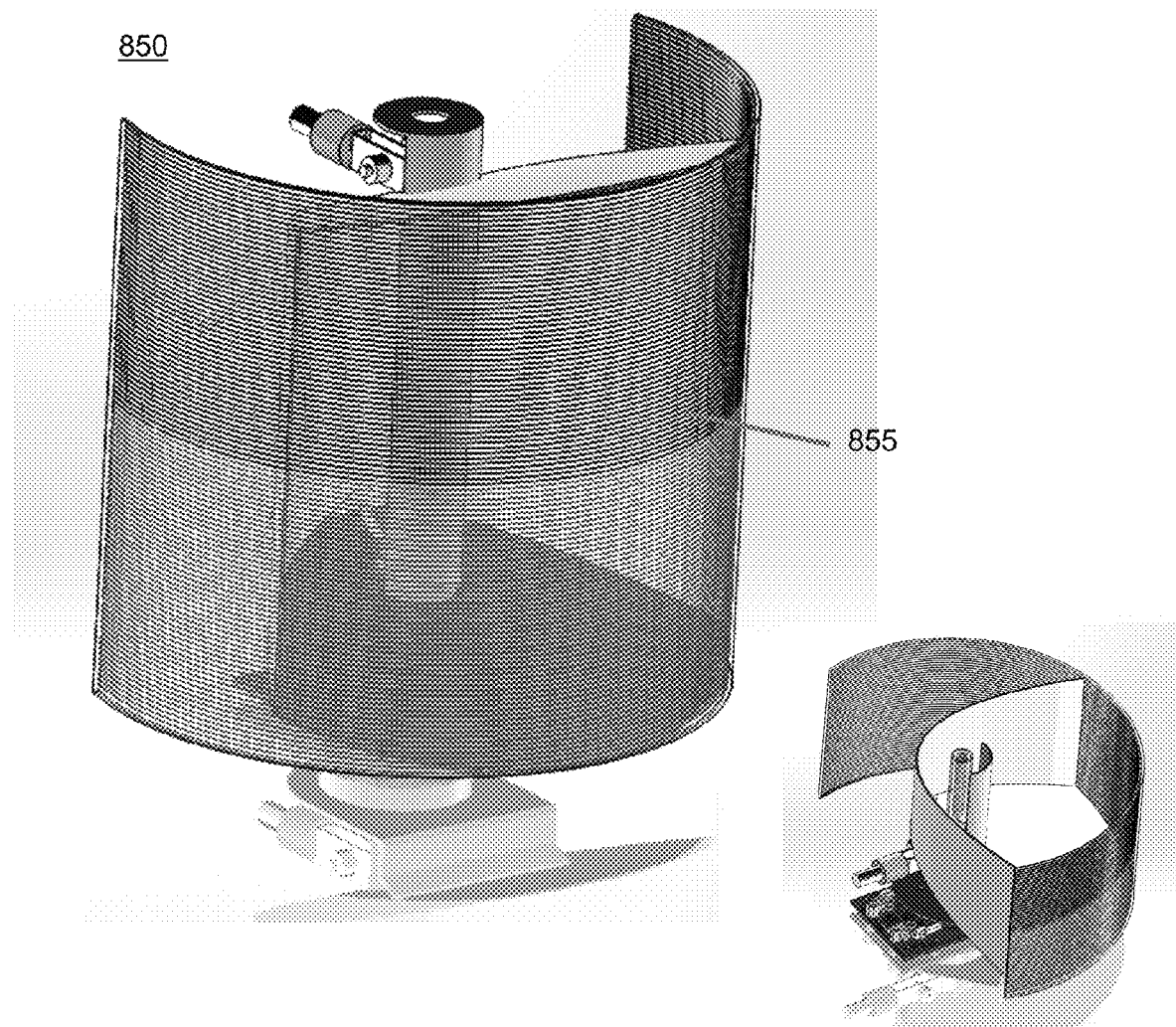
FIG. 8B is a diagram of the illuminator of FIG. 7C with a Fresnel prism lens curved into a cylindrical arc at the exit aperture, according to an illustrative embodiment.

FIG. 8A shows an illustrative embodiment of an illuminator 800 (e.g., as shown in FIGS. 7A and 7B) that is augmented with a planar Fresnel prismatic lens 805. Utilizing the configuration shown in FIG. 7A, it may be necessary to rotate the Fresnel lens together with the reflective surfaces in order to scan the projected light stripe across the scene. Depending on the additional weight of the lens, this may not be practical. The inset to FIG. 8A depicts the redirection of illumination light as it passes through the Fresnel prismatic lens 805. An alternative Fresnel lens is shown in FIG. 8B, whereby a cylindrical (e.g., curved) Fresnel lens 855 is located exterior to the parabolic reflector of illuminator 850, so that as the reflector rotates about the emitting tube, the resulting collimated beam is always directed at a Fresnel prismatic lens which redistributes the light along the vertical axis of the exit aperture. The inset to FIG. 8B shows the system rotated to a different angle. This arrangement is reminiscent of a lighthouse lamp with central light source, a rotating reflector to direct the light, and a set of discrete Fresnel lenses arrayed around the outside to concentrate the beam as it sweeps around the lighthouse tower. In certain embodiments, the illuminator comprises multiple filaments, and may be segmented along its axis to emit higher optical power from bottom to top in order to structure the power along the structured beam of illumination projected by the illuminator.

Figure 9A:
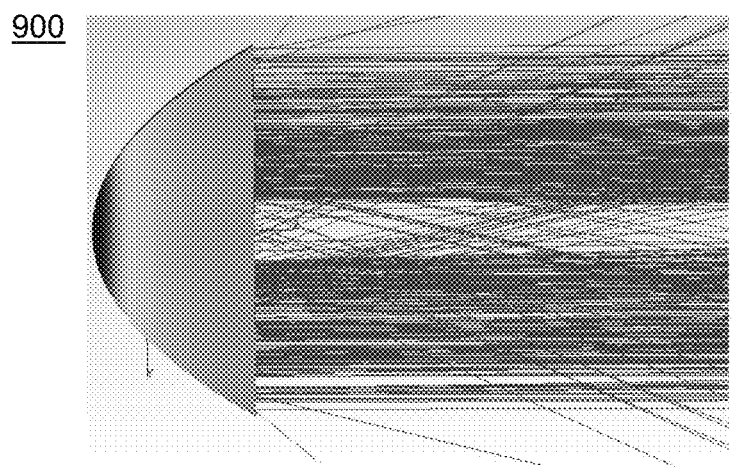
FIG. 9A is a diagram obtained from a ray-tracing model of light exiting the illuminator of FIG. 7A, viewed from above the illuminator, according to an illustrative embodiment.
Figure 9B:
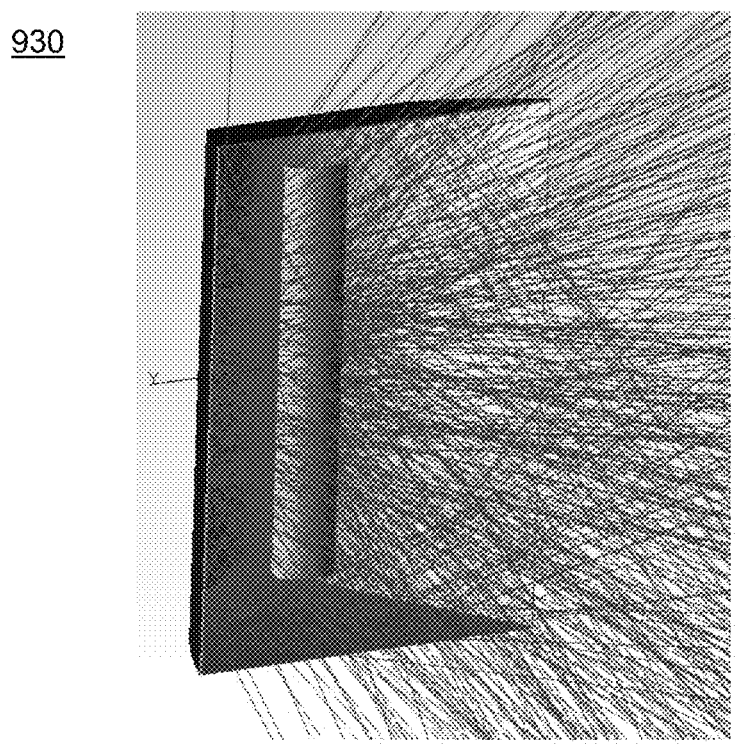
FIG. 9B is a diagram obtained from a ray-tracing model of light exiting the illuminator of FIG. 7A, viewed looking into the illuminator, according to an illustrative embodiment.
Figure 9C:
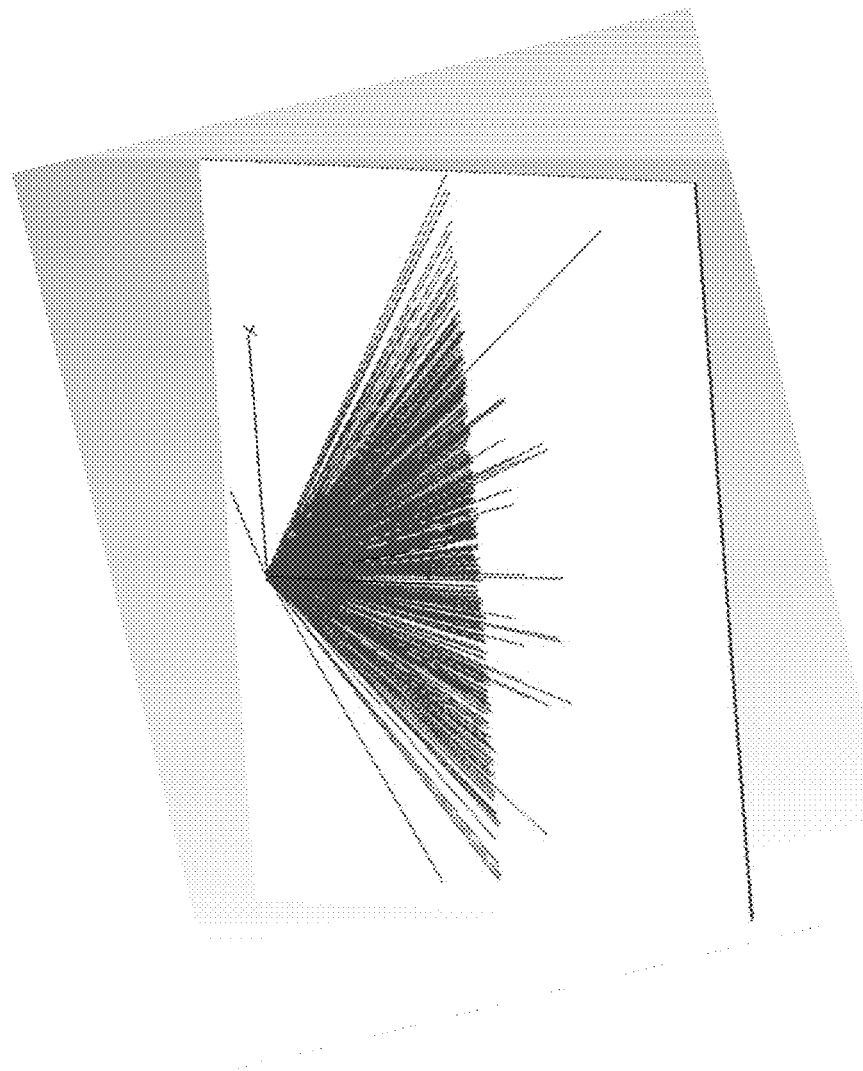
FIG. 9C is a diagram of the illuminator rays, in the form of an approximately collimated striped beam, projected onto a vertical surface, according to an illustrative embodiment.

Purely geometric ray tracing models, the results of which are shown in FIGS. 9A, 9B, and 9C, provide initial insights into how light is directed by the reflective and refractive components of the proposed illuminator optics.

Results of ray tracing are shown in diagram 900 FIG. 9A, whereby the collimated beam formed by the reflectors is apparent (as are the stray light rays). FIG. 9B shows a diagram 930 of the distribution of rays when viewing into the parabolic reflector, in the absence of a Fresnel lens. FIG. 9C shows a diagram 960 of the projection of the structured light stripe onto a vertical target, again in the absence of a Fresnel lens.

Figure 10:
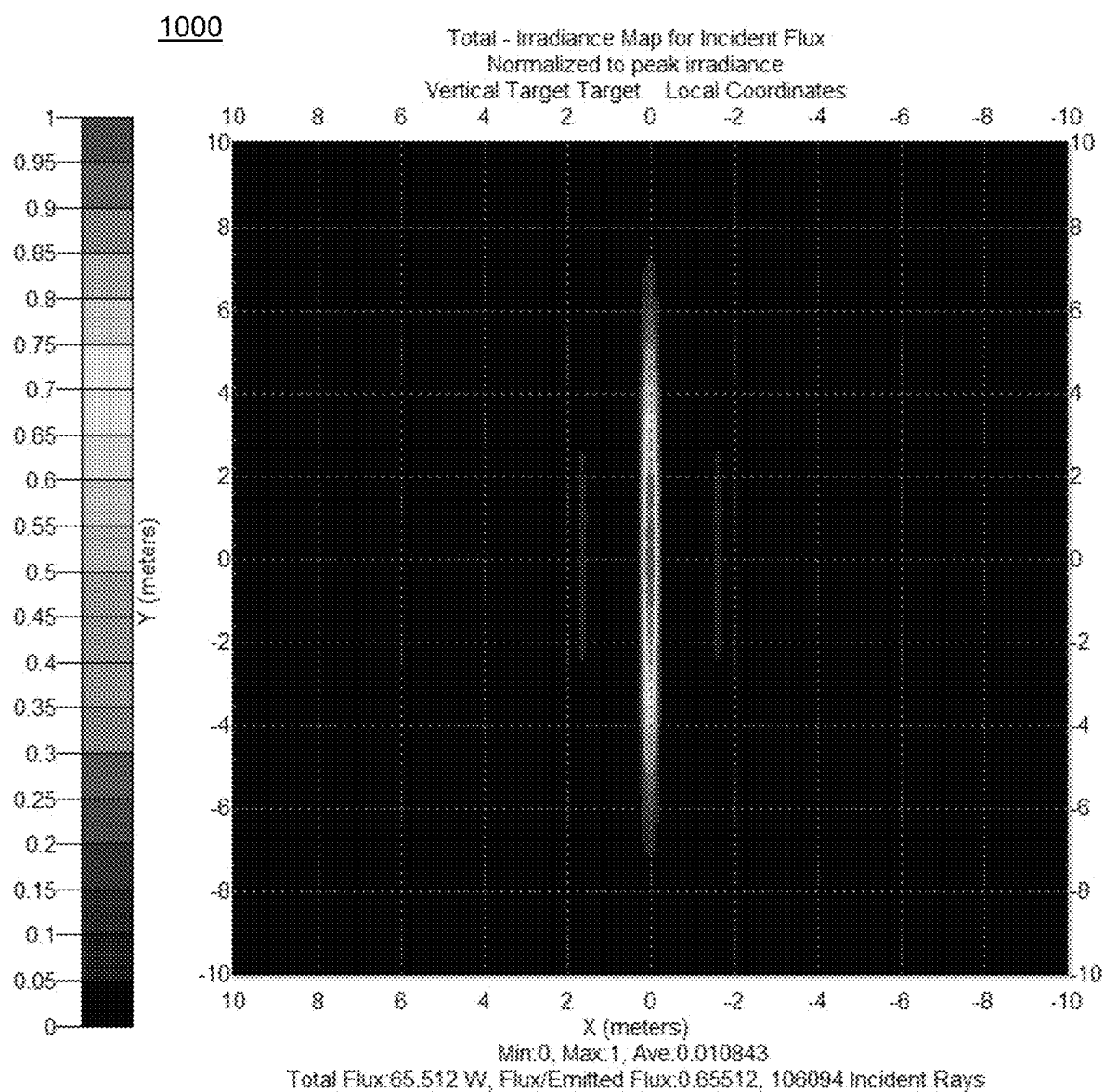
FIG. 10 is a map of the normalized irradiance projected from the illuminator of FIG. 7A onto a vertical surface at 7.5 meters, according to an illustrative embodiment.
Figure 11:
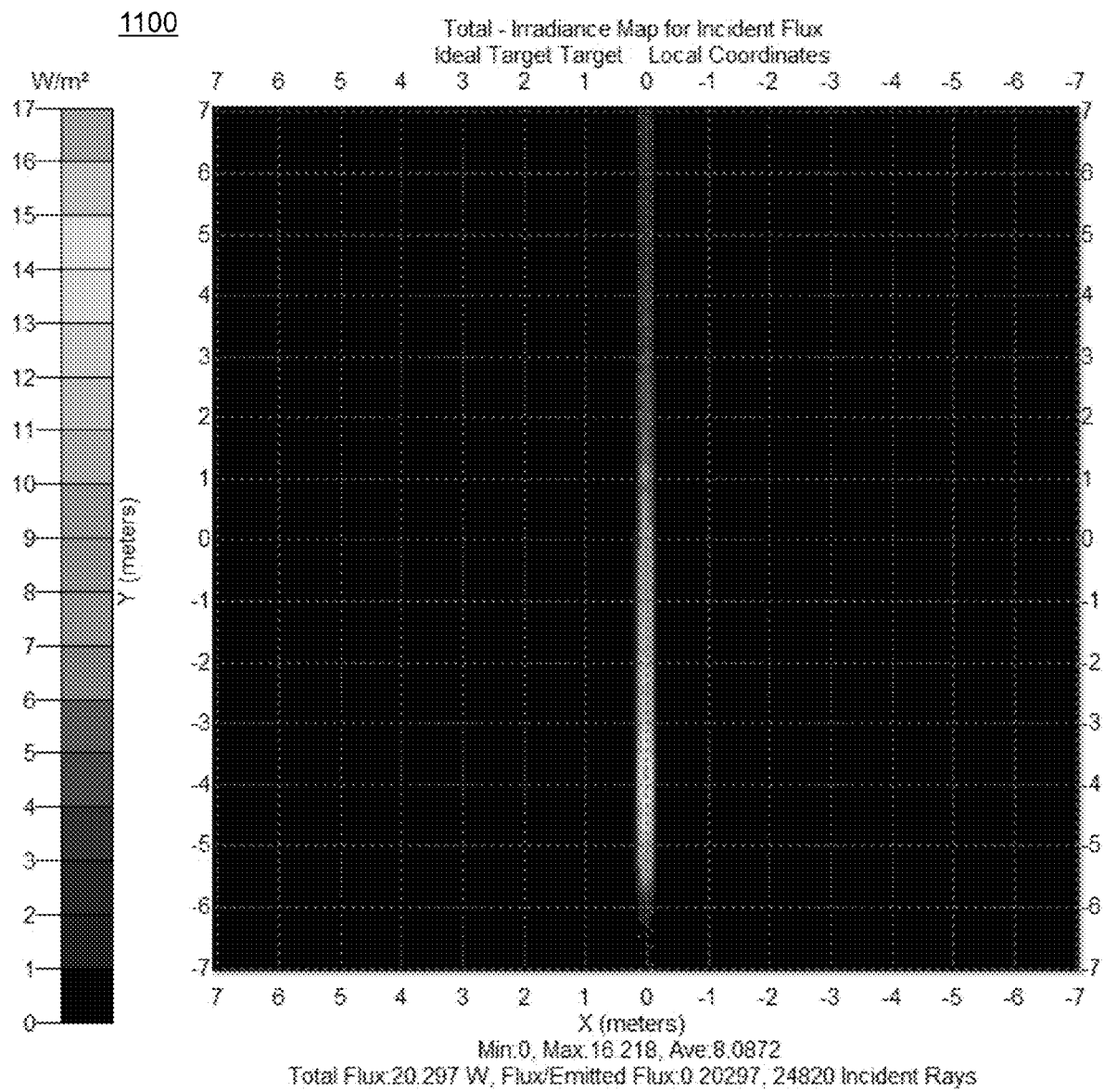
FIG. 11 is a map of the irradiance projected from a 100 watt source onto the ground from the illuminator of FIG. 7A elevated atop a 6 m mast, according to an illustrative embodiment.
Figure 12:
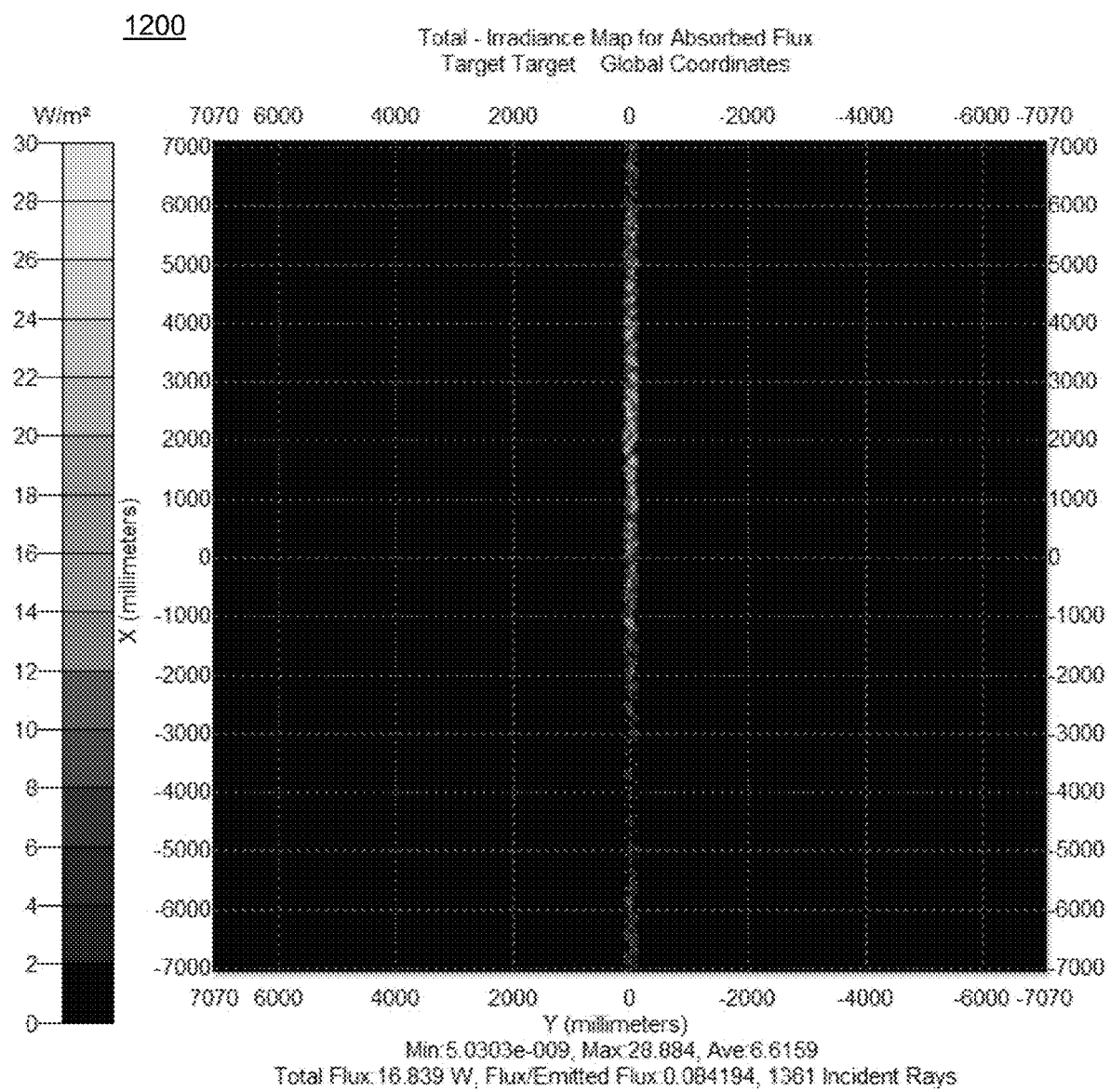
FIG. 12 is an irradiance map demonstrating how the irradiance map of FIG. 11 is altered by the inclusion of a Fresnel lens as in FIG. 8A, constructed using only a single prism angle, according to an illustrative embodiment.

The resulting irradiance pattern projected from a 90 mm coiled filament onto a vertical target at 7.5 meters from the illuminator is shown in irradiance map 1000 of FIG. 10, where irradiance is normalized to its peak value at the center of the projected beam. It is apparent that a fairly constant power distribution extends over an approximately 4 meter vertical extent, with a power reduction by only half extending over an 8-meter extent. It is also apparent that weak side-lobe stripes form at about one-tenth the peak power. They are a consequence of both the extended helical filament source and the refraction of rays by the glass tube that encases the filament. The same illuminator, without a Fresnel lens, is considered mounted on a mast at 6-meter elevation, and aimed obliquely towards a ground plane to project a radial stripe, similar to the geometry shown in FIGS. 6A and 6B. The resulting irradiance pattern 1100 is shown along a 7-inch wide stripe in FIG. 11, where the power flux incident on the ground is shown as normalized to a 100 watt emitter. A 7-inch wide strip is selected to match the width of the exit aperture of the parabolic reflector. It is clear that the flux incident upon the ground stripe first increases with range towards a maximum and then decreases rapidly with increasing range. By adding a Fresnel prismatic lens at the exit aperture, the flux incident upon the ground can be redistributed. Irradiance map 1200 of FIG. 12 illustrates this redistribution of irradiance using a Fresnel prism, where only a single angle prism is repeated. By utilizing multiple prisms of different angles and patterning them vertically at the exit aperture, it is possible to redistribute the flux from the illuminator to achieve a desired irradiance map on the ground.

In a preferred embodiment, the illuminator and sensor are mounted in an arrangement where their alignment is vertical, parallel to the axis of the slow scanning direction of both. This eliminates any parallax between the location of the projected stripe and the location and orientation of the rapid scan direction of the sensor.

The scanning of the sensor instantaneous-field-of-view (ifov) and of the light stripe emitted by the illuminator need to be synchronized such that the ifov of the sensor and the light stripe overlap during operation. In a preferred configuration the synchronization is such that the ifov is completely covered by the light stripe at all times during the process of acquiring an image. One way to achieve this is to have the moving portion of the illuminator and of the sensor mechanically connected and to use one rotation stage (or other means of actuation) to rotate both. However, this mechanical coupling of the two scanning mechanisms might result in a mechanically complex or fragile design, it might place the heat generated by the illuminator close to the sensor (which may be undesirable), and it may make it more difficult to remove, change, or maintain the illuminator.

Thus, in a preferred embodiment the scanning portion of the illuminator and of the sensor are moved by two or more separate means of actuation (e.g., two stepper motors, or two continuous motion motors, or one stepper motor and one continuous motion motor). In this embodiment, a computing unit sends control signals to multiple means of actuation such that each means of actuation moves in such a way that the ifov of the sensor and the light beam are moved by approximately the same amount at approximately the same time such as to maintain the desired overlap. In a preferred implementation, two identical stages are used and identical control signals are sent to both stages resulting in identical movement. In another implementation, different stages are used and the control signals to each stage are configured such as to achieve the movement of each stage such that the desired overlap between sensor ifov and the projected light stripe is maintained. In case the means of actuation provides for information about the absolute positions/orientations of both sensor and illuminator, this information can be sent to the computing unit and used to adjust the control signals such as to maintain the desired overlap.

vi. Example Calibration Procedures

In order to achieve an initial alignment between two means of actuation (i.e., to align the projection of the scanned ifov of the sensor and the spot of the structured illumination beam of the illuminator), or to re-align said means of actuation after a period of operation (e.g., due to drift effects), a calibration procedure is required. Automatic calibration can be implemented by projecting the light stripe onto the scene with the illuminator in a fixed orientation, and allowing the sensor to perform a horizontal scan so that the SWIR detectors find the increased reflected brightness of the projected stripe. This allows the sensor to automatically establish a scan origin that aligns it with the orientation of the illuminator. In a preferred embodiment, the scanning sensor is calibrated such that it is synchronized with the brightest portion of the stripe of illumination or centerline of a nearly uniform stripe of illumination. In another embodiment, the sensor ifov is in a fixed location and the light stripe is moved such that the sensor ifov can be realigned and synchronized with the moving stripe of illumination.

The synchronized scanning of illuminator and sensor can be implemented such that it is stepped or continuous in its movement, or a combination of scan modes may comprise stepwise, continuous, and/or variable speed motion and patterns. During scans in any of these modes, the alignment of the sensor ifov and the light beam are maintained. If, for some reason, synchronicity between movement of sensor ifov and the structured light beam are lost due to mechanical, electrical, or other means, misalignment can be detected by a computing unit connected to the sensor, for example, by repeating a horizontal scan that was completed under valid calibration and comparing new data to previous results.

If misalignment is detected, realignment can be established automatically, using for example, a scheme as described above for establishing initial alignment. For maintaining and reestablishing alignment, a control loop such as, for example, a PID control loop can be utilized.

ii. Example Detectors

Several different embodiments of SWIR imaging sensors for hydrocarbon imaging are described next. There are several different semiconductor materials that can be used to fabricate the basic photo-detector sensitive to the SWIR spectrum of light from approximately 1.0 to 2.5 microns, with a dark-current that can be suitably reduced by thermo-electric cooling. These include so-called extended-response indium gallium arsenide (extended-InGaAs) commonly grown on an indium phosphide (InP) lattice mismatched substrate, and the recently developed type-II quantum wells made from alternating layers of InGaAs and gallium arsenide antiminide (GaAsSb) grown on an InP lattice-matched substrate. These two materials have different spectral response characteristics, but both can be used for detecting the hydrocarbons that comprise natural gas, and in particular, methane as well as VOCs. They also have different manufacturing yields due to their lattice structures. Thus, extended-InGaAs photo-detectors are available as discrete photo-detectors and one-dimensional arrays but only recently introduced as two-dimensional arrays, while type-II InGaAs/GaAsSb photo-detectors are commercially available as two-dimensional arrays in extended-SWIR cameras. Mercury cadmium telluride (MCT) is a common infrared detector material that can also be used for imaging in the extended SWIR; however, its high dark-current requires cryogenic cooling with, for example, a Stirling engine to achieve useful signal-to-noise ratios.

Figure 13A:
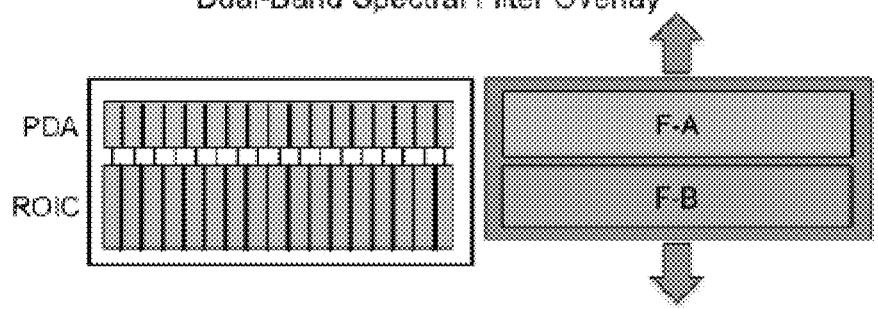
FIG. 13A is a diagram of a one-dimensional photo-detector array with its read-out circuitry, together with a pair of spectral filters that overlays the detector array and alternates between each of the two filters covering the detector array, according to an illustrative embodiment.
Figure 13B:
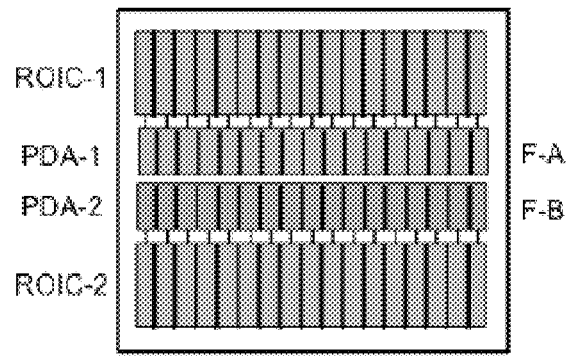
FIG. 13B is diagram of a pair of one-dimensional photo-detector arrays, each with its own read-out circuitry, and each with a different spectral filter positioned over it, according to an illustrative embodiment.

There are several embodiments of photo-detector arrays in combination with multiple spectral filters that yield a suitable sensor for use in a gas leak imaging and quantification system. FIGS. 13A and 13B show diagrams 1300 and 1350, respectively, of one-dimensional SWIR photo-detector arrays used in combination with two spectral filters called F-A and F-B, which can be used to detect one or more hydrocarbons of interest (e.g., to create the Core Band and Wings Band filters for methane detection or other hydrocarbons of interest). A one-dimensional (i.e., linear) 2.5-micron SWIR InGaAs array with 256 detectors is used in a functional prototype methane gas imager. The configuration of FIG. 13A shows a single linear array of photo-detectors with its read-out integrated circuit (ROIC) together with a pair of filters in a frame that is designed to overlay the photo-detector array and alternate between the filters F-A and F-B positioned in front of the detector array. In this example, the photo-detector array and its ROIC are mounted on a small thermo-electric cooler and enclosed inside a hermetically sealed package with a transparent window located above the photo-detectors. The alternating filter assembly is positioned outside the package so that each filter overlays the window as the filters alternate in position. This configuration uses a mechanical means to move the respective filters into place at a sufficiently fast rate to support the desired imaging requirements. Other means of alternating spectrally separated bands of light onto a linear detector array are also possible. The prototype gas imager operates at 20 frames/second. Other image acquisition rates are possible.

Diagram 1350 of FIG. 13B shows another configuration of one-dimensional SWIR photo-detector arrays and filters, where two separate linear arrays with their own ROICs are configured in parallel layout on a common thermo-electric cooler inside a hermetically sealed package with a window located above the pair of photo-detector arrays. Filters F-A and F-B are mounted either in a frame or attached on or near the window, each filter being fixed in place and located above one of the photo-detector arrays. This configuration eliminates the need to mechanically move the filters rapidly and lends itself to higher frame rates.

This configuration of two parallel linear arrays of photo-detectors can also be used with an alternating or otherwise changeable filter array such that a new pair of filters is moved into place to overlay the detector arrays. For example, a four-band imager would be created from a dual-linear detector array with alternating pairs of filters in a quad-filter frame, and could, for example, support separate detection and quantification of methane and volatile organic compounds (VOCs) or methane and carbon dioxide.

Figure 14A:
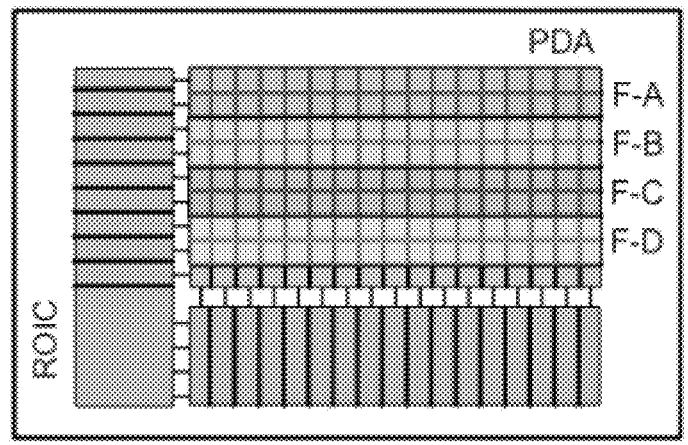
FIG. 14A is a diagram of a two-dimensional photo-detector array and its read-out circuitry, with four different spectral filters, each filter overlaying one or more rows of detectors, according to an illustrative embodiment.

Diagram 1400 of FIG. 14A illustrates the use of a two-dimensional SWIR photo-detector array and ROIC, where an array of four filters. F-A, F-B, F-C, and F-D are configured as stripes that overlay the detector array. The filter stripes can extend across most of the array, with each stripe covering one or more rows of detectors. The detector array and ROIC is to be mounted on a thermo-electric cooler and enclosed in a hermetically sealed package with a transparent window over the detector array. The filter stripes can be configured into an array as a mosaic of individual filters in a frame, or fabricated as a monolithic array, and it is clear that more than four different filters can comprise the array. Two-dimensional 2.5-micron SWIR type-II InGaAs/GaAsSb imaging arrays of size 320×256 pixels are now commercially available. This configuration can be viewed as a collection of many linear arrays covered by a set of spectral filters.

Figure 14B:
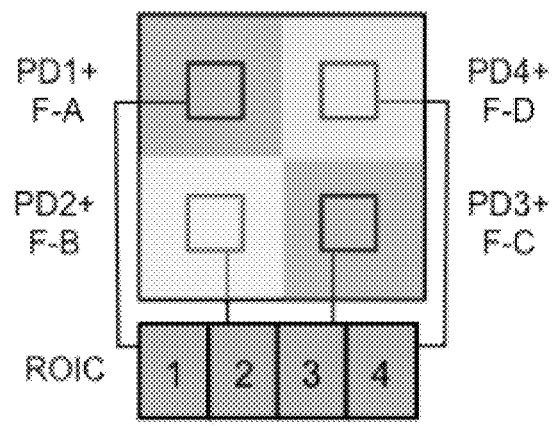
FIG. 14B is a diagram of an array of four discrete photo-detectors with their individual read-out circuits, each detector covered with a separate spectral filter island, where the spectral filters form a spectral filter mosaic, according to an illustrative embodiment.

Diagram 1450 of FIG. 14B shows a configuration of four discrete SWIR photo-detectors, PD1, PD2, PD3, and PD4, arranged in a 2×2 array, each with its own analog read-out circuit and (possibly shared) analog-to-digital converter, and each covered with a separate spectral filter island. In practice, the four discrete photo-detectors may be mounted on a common thermo-electric cooler and enclosed in a hermetically sealed package (e.g., a TO-8 "transistor-outline" metal can) with a transparent window. The spectral filters can be assembled from discrete filters into a spectral filter mosaic, or fabricated as a monolithic array of filter islands, and located outside or on the window aligned with the photo-detectors below. With the appropriate lens, this configuration forms the equivalent of a single multispectral SWIR pixel. This configuration can clearly be extended to more or fewer discrete photo-detectors, each with its own spectral filter. A minimum of two spectrally filtered photo-detectors may be required to construct a scanner that can image and quantify gas emissions. This same type of spectral filter mosaic can also be combined with the two-dimensional photo-detector array shown in FIG. 14A, whereby each filter island of the mosaic overlays a small two-dimensional sub-array of even smaller pixels. Upon read-out of the entire detector array, each sub-array of pixels corresponding to the same filter island can be combined into a macro-pixel. This configuration trades off reduced spatial resolution for increased signal in a two-dimensional array of very small photo-detectors.

Figure 15A:
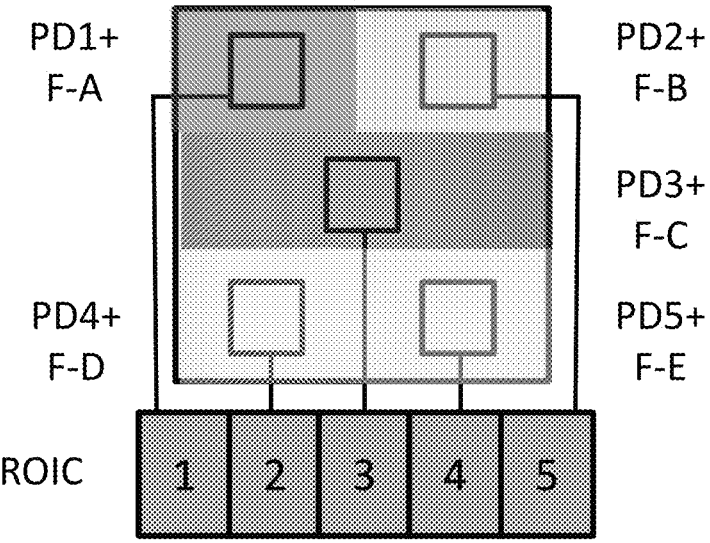
FIG. 15A is a diagram of a 5-element array of discrete photo-detectors with a 5-band spectral filter mosaic positioned over the photo-detector array, according to an illustrative embodiment.

Diagram 1500 of FIG. 15A shows a 5-element array of discrete photo-detectors with a 5-band spectral filter mosaic positioned over the photo-detector array. Five discrete photo-detectors, PD1, PD2, PD3. PD4, and PD5, are arranged in a three-row stack. Each photo-detector has a respective analog readout circuit and either dedicated or optionally shared analog-to-digital converter. Each photo-detector is covered with a separate spectral filter island, F-A, F-B, F-C. F-D, and F-E, respectively. In practice, the five discrete photo-detectors may be mounted on a common thermo-electric cooler and enclosed in a hermetically sealed package with a transparent window. The spectral filters can be located outside the window aligned with the photo-detectors below, or be located on the inside of the window, or serve as the window itself. With the appropriate lens, this configuration forms the equivalent of a single multispectral SWIR pixel, or alternatively a small multispectral detector array. This configuration can clearly be extended to more or fewer discrete photo-detectors, each with its own spectral filter.

Figure 15B:
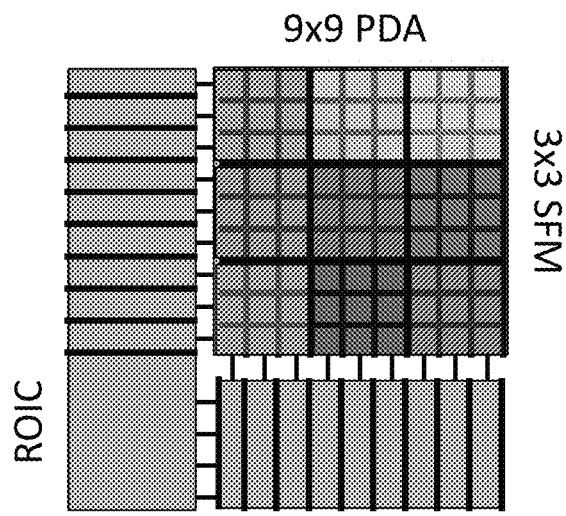
FIG. 15B is a diagram illustrating the use of a small 9×9 element array of photo-detectors where sub-arrays of 3×3 detectors form macro-pixels each covered by a different spectral filter, where the filters are arranged in a 3×3 spectral filter mosaic, according to an illustrative embodiment.

Diagram 1550 of FIG. 15B illustrates the use of a 9×9 element monolithic array of small photo-diode pixels where sub-arrays of 3×3 pixels form macro-pixels, each macro-pixel covered by a different spectral filter, and where the filters are arranged in a 3×3 spectral filter mosaic. While 3×3 pixel sub-arrays are illustrated, each filter island of the mosaic overlays a two-dimensional rectangular sub-array of small pixels. Upon readout of the entire detector array, each sub-array of pixels corresponding to the same filter island can be combined into a macro-pixel. This configuration trades off reduced spatial resolution for increased signal in a two-dimensional array of very small photo-detectors. Two-dimensional 2.5-micron SWIR type-II InGaAsr-GaAsSb imaging arrays of various numbers of pixels, for example 64×64 pixels, can be adapted for use in the illustrated embodiment.

All of the multispectral SWIR detector configurations described and shown, e.g., in FIGS. 13A, 13B, 14A, 14B, 15A, and 15B, may utilize additional scanning and focusing optics in order to create two-dimensional spectral imagery from which a gas absorption image can be created. As is known to one of ordinary skill in the art, all the detector embodiments shown in FIGS. 13A, 13B, 14A, 14B, 15A, and 15B lend themselves to packaging in hand-portable systems, and can also be configured to operate on moving platforms such as ground vehicles, airborne rotorcraft, and fixed-wing platforms, ships, rotating mast-mounted systems, translating rail-mounted systems, and orbiting satellites.

B. Example Approaches to Multispectral Imaging

Figure 16A:
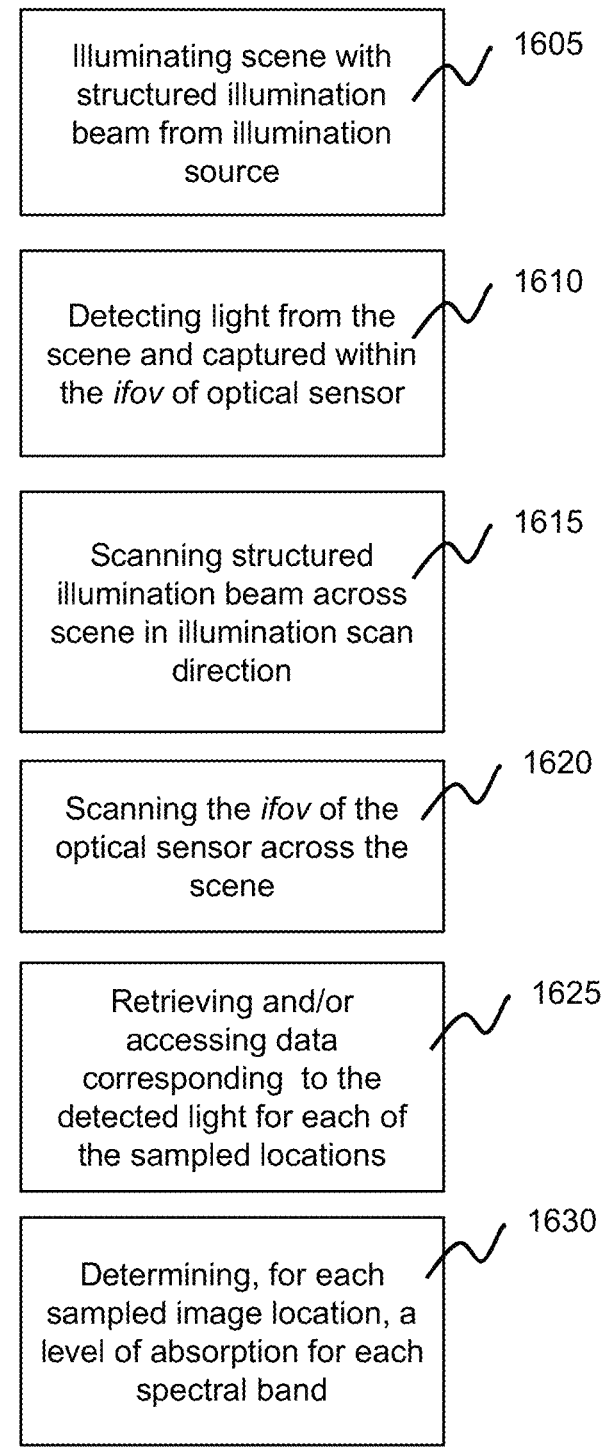
FIG. 16A is a block flow diagram of a method of obtaining a multispectral absorption image of a scene using a structured illumination beam synchronized with an scanned instantaneous field of view (ifov) of an optical sensor, according to an illustrative embodiment.

FIG. 16A is a block flow diagram of a method 1600 for obtaining a multispectral absorption image of a scene using a structured illumination beam synchronized with an instantaneous field of view (ifov) of an optical sensor, according to an illustrative embodiment. In step 1605, a scene to be imaged is illuminated with a structured illumination beam from an illumination source. The structured illumination beam has a first beam size along a first beam axis. For example, the structured illumination beam may be a rectangular stripe. In step 1610, one or more spectral detectors of an optical sensor detect light from the scene and captured within the ifov of the optical sensor. The ifov of the optical sensor is rapidly scanned along a first scan axis that is aligned with the first beam axis. In step 1615, the structured illumination beam is scanned across the scene in an illumination scan direction that is substantially orthogonal to the first beam axis.

In step 1620, the ifov of the optical sensor is scanned along a second scan axis, to raster scan the ifov across the scene, and thereby detect light from a plurality of sampled locations within the scene, each corresponding to a particular position of the ifov within the raster scan. The first scan axis is aligned with the first beam axis, and the second scan axis is aligned with the illumination scan direction. The scanning of the structured illumination beam and the scanning (along the slow axis) of the ifov are synchronized so as to maintain overlap between the ifov and the structured illumination beam. Accordingly, as the illumination spot is scanned 1615, the projection of the sensor ifov is scanned first along the length of the illumination spot 1620 (along the first scan axis) and then scanned along the second scan axis as the illumination spot is moved in the illumination scan direction, to maintain overlap between the projection of the sensor ifov and the illumination spot.

For example, in certain embodiments both the illumination spot and the projection of the sensor ifov are scanned along the illumination scan direction in a stepwise fashion (e.g., via a stepper motor). As the illumination spot is stepped along the illumination scan direction, the projection of the sensor ifov is moved to a location such that it overlaps with the illumination spot. Since the illumination spot may have a width larger than the projection of the sensor ifov, alignment between the steps in the illumination spot scan and those in the sensor ifov scan need not be highly accurate. At each position in the stepwise scan, the projection of the sensor ifov can be scanned (e.g., in a continuous fashion), in the first scan direction, along the length of the illumination spot. In this manner, a grid of sampled image locations can be obtained.

In certain embodiments, the projection of the sensor ifov is scanned along the first and second scan axes in continuous fashion. The first scan axes and second scan axes may be fast and slow axes, respectively, of the optical sensor scanner. The illumination beam may be scanned also in a continuous manner, along the illumination scan direction, at a rate comparable to that at which the projection of the sensor ifov is scanned along the slow axis. The projection of the sensor iv may then be scanned rapidly along the fast axis, such that it can be scanned one or more times along the length of the illumination spot before it moves it an appreciable distance along the slow axis. For example, in certain embodiments, to obtain appropriately spaced samples along the slow axis, the scanning rate for the fast axis needs to be sufficiently fast so as allow the projection of the sensor ifov to be scanned along the length of the illumination spot before it moves an appreciable distance (e.g., corresponding to an ifov of an individual detector of the optical sensor) along the slow axis. In certain embodiments, there is a trade-off between width of the illumination spot and how much it can be displaced during a scan along the fast axis. In certain embodiments, the illumination spot has to be wide enough, and scan slow enough, such that the projection of the sensor ifov is covered with light, yet the sensor ifov will either step or slowly move by a single detector ifov during the fast scan. Accordingly, the illumination spot should be at least as wide as the sensor ifov plus an individual detector ifov.

In certain embodiments, the optical sensor ifov can be scanned in a continuous fashion along the slow axis, while the illumination spot is scanned in a stepwise manner, with the scanning of the sensor ifov and the illumination spot synchronized so as to maintain overlap between the two as both are scanned. Likewise, in certain embodiments, the optical sensor ifov can be scanned in a stepwise fashion along the slow axis, while the illumination spot is scanned in a continuous manner (e.g., slowly), with the scanning of the sensor ifov and the illumination spot synchronized so as to maintain overlap between the two as both are scanned.

In step 1625, a processor of a computing device retrieves and/or accesses data corresponding to the detected light for each of the sampled locations. In step 1630, for each of the plurality of sampled image locations, the processor determines, using the detected light at the sampled image location, a corresponding level of absorption for each of one or more spectral bands, thereby obtaining a multispectral absorption image of the scene. For example, the multispectral absorption image may include a plurality of pixels, each corresponding to a particular sampled image location and having one or more intensity values, each intensity value based on a determined level of absorption at a particular spectral band of the one or more spectral bands.

Figure 16B:
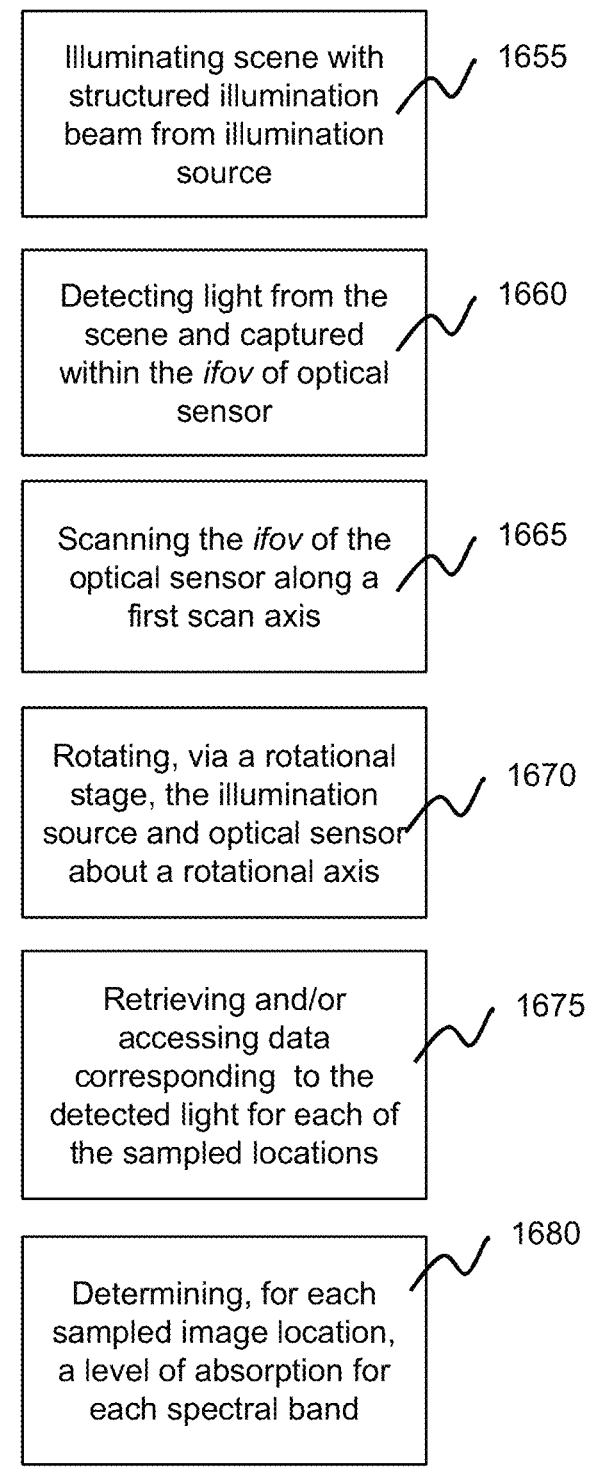
FIG. 16B is a block flow diagram of a method for obtaining a multispectral absorption image of a scene using a structured illumination beam produced by an illumination source mechanically coupled to a scanning optical sensor, according to an illustrative embodiment.

FIG. 16B is a block flow diagram of a method 1650 for obtaining a multispectral absorption image of a scene using a structured illumination beam produced by an illumination source coupled to a scanning optical sensor, according to an illustrative embodiment. In step 1655, a scene to be imaged is illuminated with a structured illumination beam from the illumination source, wherein the structured illumination beam has a first beam size along a first beam axis. In step 1660, one or more spectral detectors of an optical sensor detect light from the scene and captured within the ifov of the optical sensor. In step 1665, the ifov of the optical sensor is scanned along a first scan axis (the fast axis), at least a portion of which is substantially coincident with the first beam axis such that the ifov overlaps with the structured illumination beam as the ifov is scanned along the first scan axis (e.g., so as to scan the ifov over a region of the scene illuminated by the structured illumination beam);

In step 1670, a rotational stage, on which both or each the illumination source and optical sensor are mounted and maintained in substantially fixed alignment with respect to each other, rotates the illumination source and optical sensor about a rotational axis that is substantially parallel to the first scan axis and/or first beam axis, such that (i) rotation of the rotational stage(s) scans the structured illumination beam and ifov (in synchrony) in a second scan direction that is substantially orthogonal to the first scan axis, and (ii) scanning of the ifov along the first scan axis in combination with rotation of the rotational stage(s) raster scans the ifov across the scene, thereby detecting light from a plurality of sampled locations within the scene, each corresponding to a particular position of the ifov within the raster scan.

In step 1675, a processor of a computing device retrieves and/or accesses data corresponding to the detected light for each of the sampled locations. In step 1680, for each of the plurality of sampled image locations, the processor determines, using the detected light at the sampled image location, a corresponding level of absorption for each of one or more spectral bands, thereby obtaining a multispectral absorption image of the scene. For example, the multispectral absorption image may include a plurality of pixels, each corresponding to a particular sampled image location and having one or more intensity values, each intensity value based on a determined level of absorption at a particular spectral band of the one or more spectral bands.

C. Operation of Example Sensor Embodiments

Figure 17A:
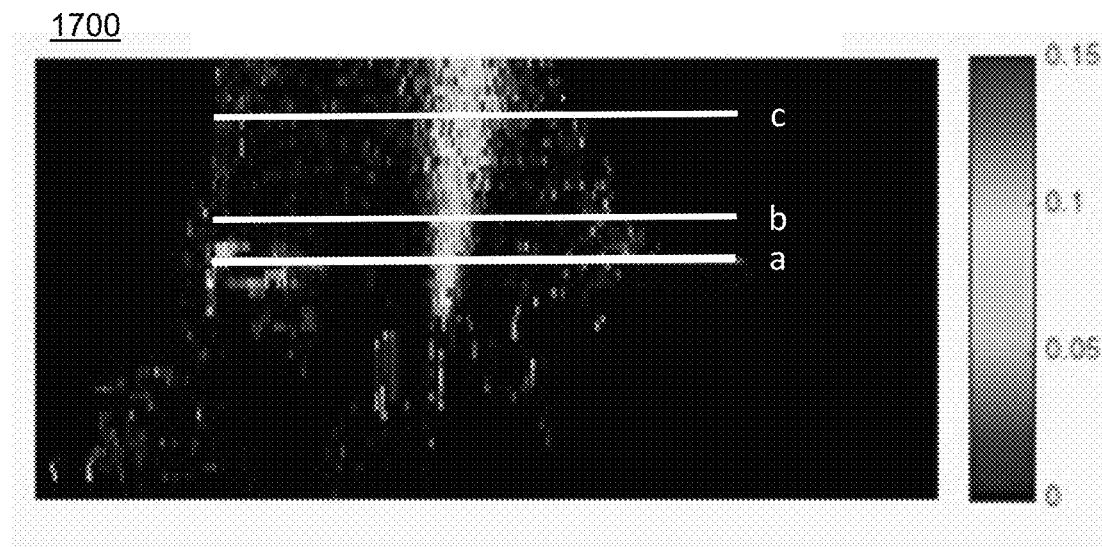
FIG. 17A is a real-time absorption image of a methane gas jet exiting a 1 mm orifice from a test manifold pressurized to 1300 psig, according to an illustrative embodiment.

FIG. 17A is a real-time absorption image 1700 of a methane gas jet exiting a 1 mm diameter round orifice with an internal pressure of 1300 psig (pounds per square inch—psi "gauge", i.e., relative to external atmospheric pressure of approximately 14.5 psi). The absorption image is colored according to a pixel-level differential optical depth scale shown to the right. This pixel-level differential optical depth is directly proportional to the number of methane molecules along each cone of rays between the light source (or reflection of the light source off a background material) and the photo-detector corresponding to each pixel; this is the so-called pixel column density of the gas.

The turbulent structure of the jet is apparent near the top of the jet image. It is clear from the absorption image that the jet diameter grows linearly along the jet axis, as is consistent with the theoretical self-similar solution for turbulent jets. In this image, it is the noise level of the background differential optical depth that delineates the boundary of the jet and so limits the visible diameter.

Figure 17B:
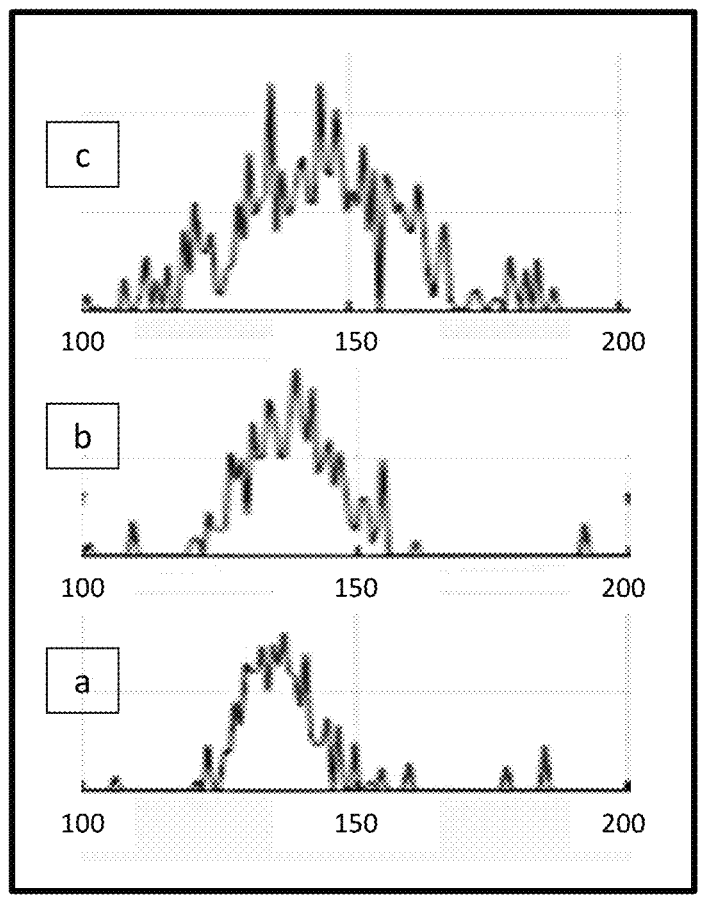
FIG. 17B is plots of differential optical depth across the methane gas jet of FIG. 17A, corresponding to pixel values sampled along the lines labeled a, b, and c, according to an illustrative embodiment.

FIG. 17B shows cross-sectional profiles of the jet absorption image. The graphs plot differential optical depth vs. pixel number across a row of 512 pixels corresponding to the horizontal lines labeled a, b, c in FIG. 17A. It is apparent from these plots that the diameter of these absorption profiles is increasing along the jet axis, and that the turbulence creates fluctuations in absorption through the jet. The general shape of these plots is entirely consistent with the path length through a cross-section of a round jet in combination with a radial concentration profile of Gaussian shape. Superposed on this smooth theoretical profile are fluctuations in concentration due to turbulence.

The maximum of the absorption on each profile should occur on axis of the jet, if the imaging line-of-sight is perpendicular to the jet axis, as this is where the path length through the jet is a maximum and the gas concentration is largest. Based on the self-similar solution for turbulent round jets, the gas concentration on axis will decrease linearly along the jet as it expands, while the diameter increases linearly along the axis, and so the product of axial gas concentration with diameter should remain a constant, suggesting the column density along the jet axis should remain constant. However, due to the turbulent fluctuations, these profiles change over time, and so individual pixel values fluctuate. To cope with these turbulent fluctuations, it is suggested to use spatial averages of quantities across the jet, and then calculate the total absorption of a slice of jet, as it is due to the total mass of gas in that slice and not sensitive to the exact distribution of mass throughout the slice. Each row of pixels along consecutive cross-sections through the jet corresponds to a constant thickness slice, and since the jet diameter varies linearly with axial distance, hence, the slice volume increases as the square of the axial distance. But since the gas concentration dilutes linearly with axial distance in a self-similar round jet, the mass of gas in constant thickness slices is expected to increase linearly with axial distance along the jet. That is, the gas at the front of a jet slice flows slower than the gas at the rear of the jet slice, causing mass to build up between slices of constant thickness. And since the mass of gas in slices increases linearly along the jet axis, so should the absorption due to that mass. Thus, the integrated differential optical depth across each cross-section of the jet image should increase linearly along the jet. Similarly, the jet width in the absorption image should increase linearly along the jet, where the jet boundary is determined by the noise in the background image. Integrating the absorption across jet cross-sections acts to smooth out the effect of turbulent fluctuations on gas concentration in the jet.

Figure 18A:
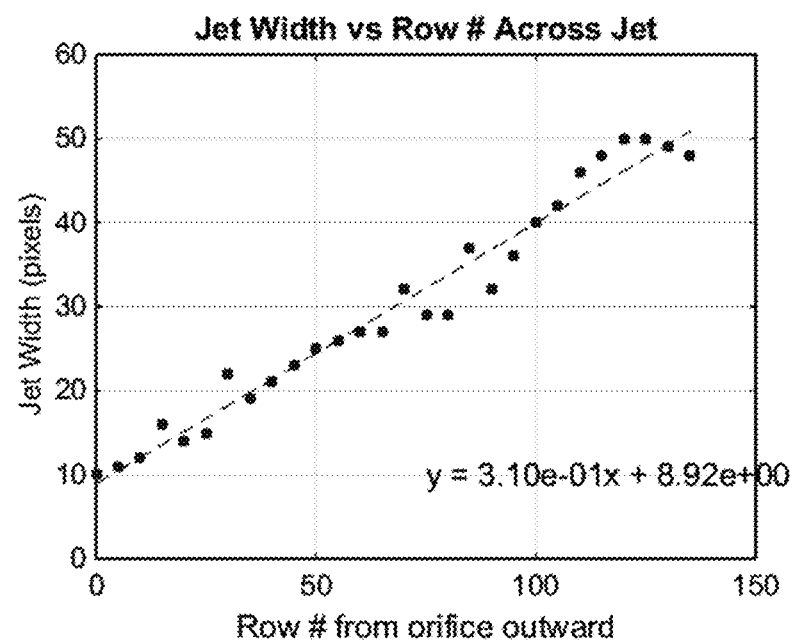
FIG. 18A is a graph of the estimated jet width along the axis of the methane jet of FIG. 17A, and a least-squares linear regression to these data points, according to an illustrative embodiment.
Figure 18B:
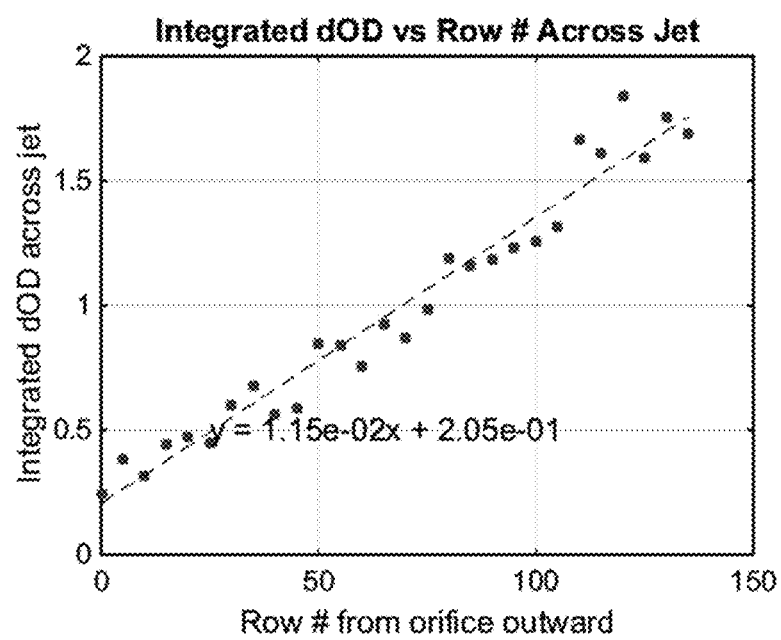
FIG. 18B is a graph of the integrated differential optical depth across the width of the jet, along the axis of the methane jet of FIG. 17A, and a least-squares linear regression to these data points, according to an illustrative embodiment.
Figure 18C:
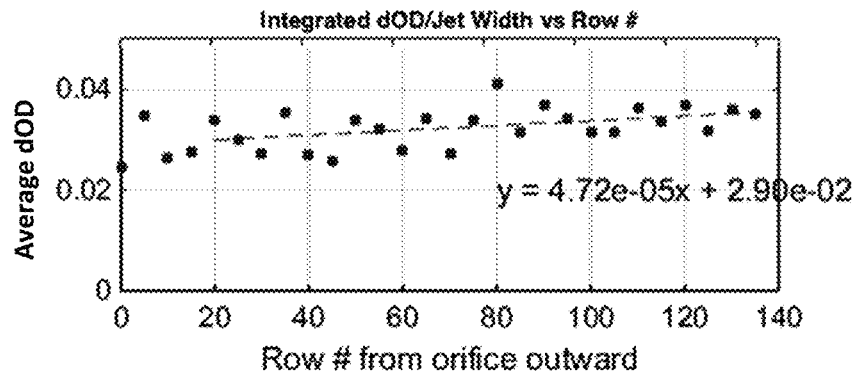
FIG. 18C is a graph of the ratio of integrated differential optical depth to estimated jet width (i.e., the average differential optical depth) along the axis of the methane jet of FIG. 17A, and a least-squares linear regression to these data points, according to an illustrative embodiment.

FIGS. 18A and 18B plot the automatically extracted jet width and corresponding integrated differential optical depth (integrated-dOD), respectively, along the axial distance (approximately the image row number) for the jet image in FIG. 17A. It is apparent that both quantities follow clear linear trends, and so a least-squares regression line is fit to each quantity. Forming the ratio of integrated differential optical depth to jet width yields an average differential optical depth (Avg-dOD) value at each axial location along the jet. This ratio is plotted in FIG. 18C, to which a least-squares regression line is fit (starting away from the orifice to exclude the complex acoustic region just outside the hole). It is apparent from FIG. 18C that the slope of this regression line is very small, and that the intercept of the regression line then corresponds to the average differential optical depth extrapolated back to the effective orifice from which the gas leaks under pressure.

Figure 19:
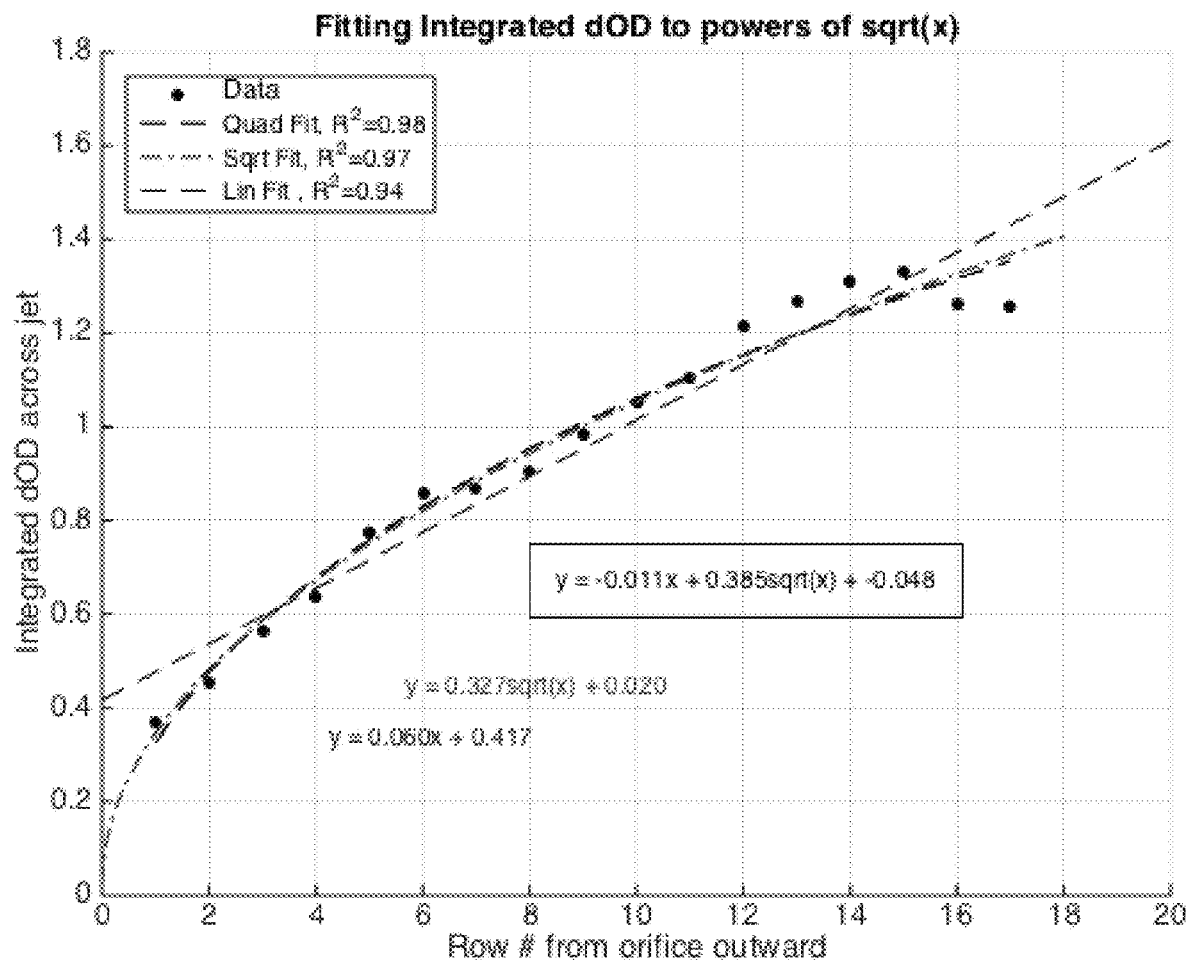
FIG. 19 is a graph of the integrated differential optical depth across the width of a methane jet exiting a narrow slit (i.e., an idealized "crack" with a width of 50 micrometers and length of 1 cm) at a pressure of 60 psig, according to an illustrative embodiment.

FIG. 19 plots the integrated differential optical depth (integrated-dOD) along the axis of a natural gas jet emanating from a narrow (50 micron) slit orifice that is 1 cm long, meant to emulate a crack (instead of a hole) in a pressurized line at 60 psig. Following the same reasoning as above but for a plane turbulent jet (instead of a round turbulent jet), one finds that the integrated-dOD should scale with the square-root of the distance along the axis, as is apparent from the least-squares regression fits in FIG. 19. And since the integrated-dOD across a plane jet is independent of the orientation of the slit relative to the line-of-sight of the sensor, one can use this square-root versus linear behavior to distinguish between a gas leak emanating from a crack or a hole.

i. Mass Flux Across a Range of Pressures and Orifice Sizes

Experiments have been conducted to image the release of methane gas across a range of pressures (50-1400 psig) exiting from round orifices (diameters of 0.75 mm and 1.0 mm). Gas jet boundaries are automatically extracted from the imagery, and the average differential optical depth (Avg-dOD) along the jet axis is computed. Fitting a least-squares regression line to this data determines the intercept of this regression line, which indicates the degree of absorption of the methane at the effective orifice.

Figure 20A:
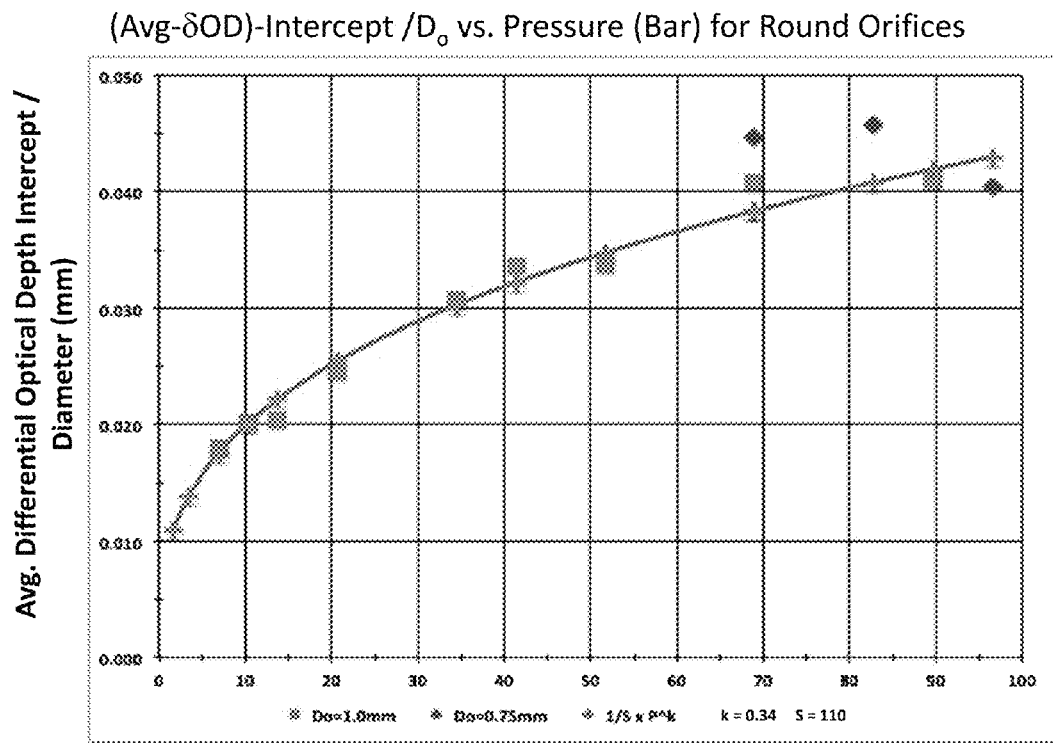
FIG. 20A is a graph of the intercept value of average differential optical depth relative to the diameter of the leak hole vs. the internal pressure (in Bar) driving a methane jet from orifices of 1 mm and 0.75 mm, and compares the data to a smooth power-law curve, according to an illustrative embodiment.

FIG. 20A plots the value of this Avg-dOD intercept (scaled by orifice diameter) against the internal pressure P (in units of Bar, where 1 Bar=14.5 psi, the atmospheric pressure at sea level) for round orifices of 1 mm and 0.75 mm. The data points are consistent with a power-law behavior of pressure, for which the scaling constant and exponent values are shown on the graph. This is expected since the absorption by the methane gas at the effective exit hole (extrapolating back from the linear boundaries of the jet) will be proportional to the product of the effective orifice diameter and the local gas density, while the gas density is proportional to a power-law of the pressure through the adiabatic equation of state using the ratio of heat capacities for methane. Further experiments will determine the general utility of this specific power-law relationship across a range of orifice diameters and (approximately round) shapes. Without wishing to be bound by any particular theory, the scale factor for this power-law relationship is likely to depend on the particular spectral bands used to form the differential optical depth values, because the spectral absorption coefficients form a link between the absorption of radiation by the gas and the hydrodynamics of the turbulent jet.

Figure 20B:
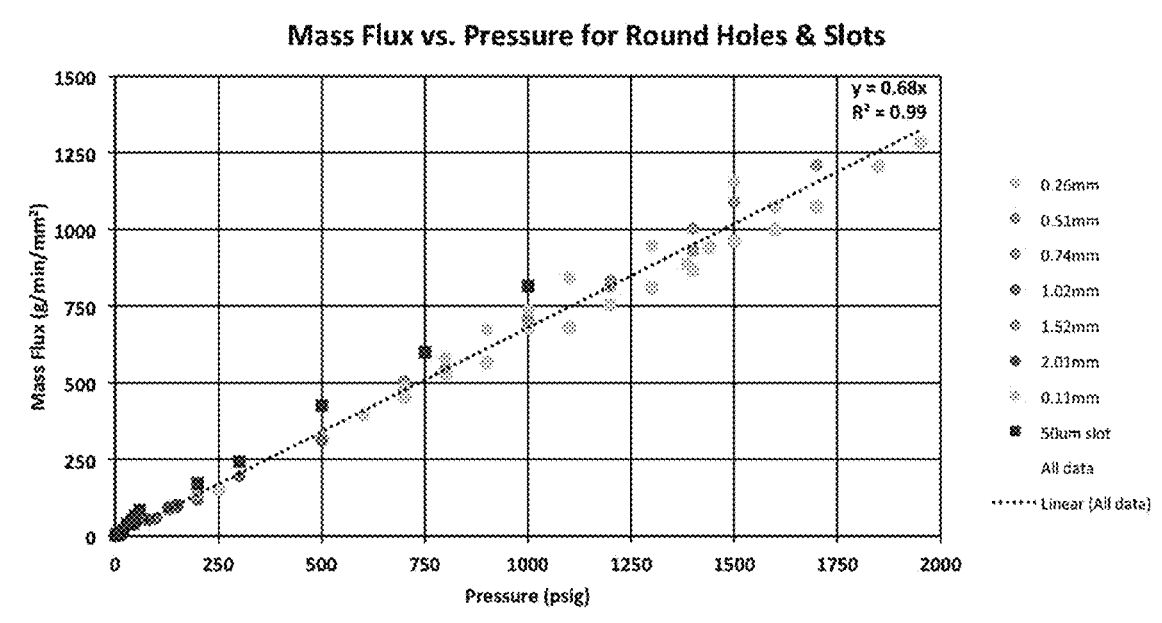
FIG. 20B is a graph, for an extensive set of experiments including round and slit orifices of various sizes, of the measured mass flux of methane (in grams per minute per unit area of the hole) vs. the internal pressure (in psig) driving the methane jet, and a least-squares linear fit to the data, according to an illustrative embodiment.

FIG. 20B plots the measured methane mass flux per orifice area (in grams/sec, divided by orifice area) against internal pressure for numerous experiments using round and slit orifices of different sizes. It is clear they follow the expected linear relationship, with a slope determined by the data. The mass flux out of the orifice is proportional to the product of the area of the orifice and the methane gas density in the pipe (which is proportional to the pressure in the pipe). Thus, while the Avg-dOD intercept curve scales linearly with effective diameter of a round orifice (as implied by FIG. 20A), the mass flow scales like the square of the effective diameter of a round orifice (as implied by FIG. 20B). These relationships taken together are therefore used to estimate the orifice size and mass flux of gas directly from the observed absorption image of a gas jet leaking from a hole under known internal pressure. Thus, it is possible to estimate the size of a leak hole directly from a gas jet absorption image, even if the leak hole itself is not visible in the image. This leads directly to a leak rate or mass flux estimate. Similar relationships apply to a planar gas jet leaking from a narrow crack.

Figure 21A:
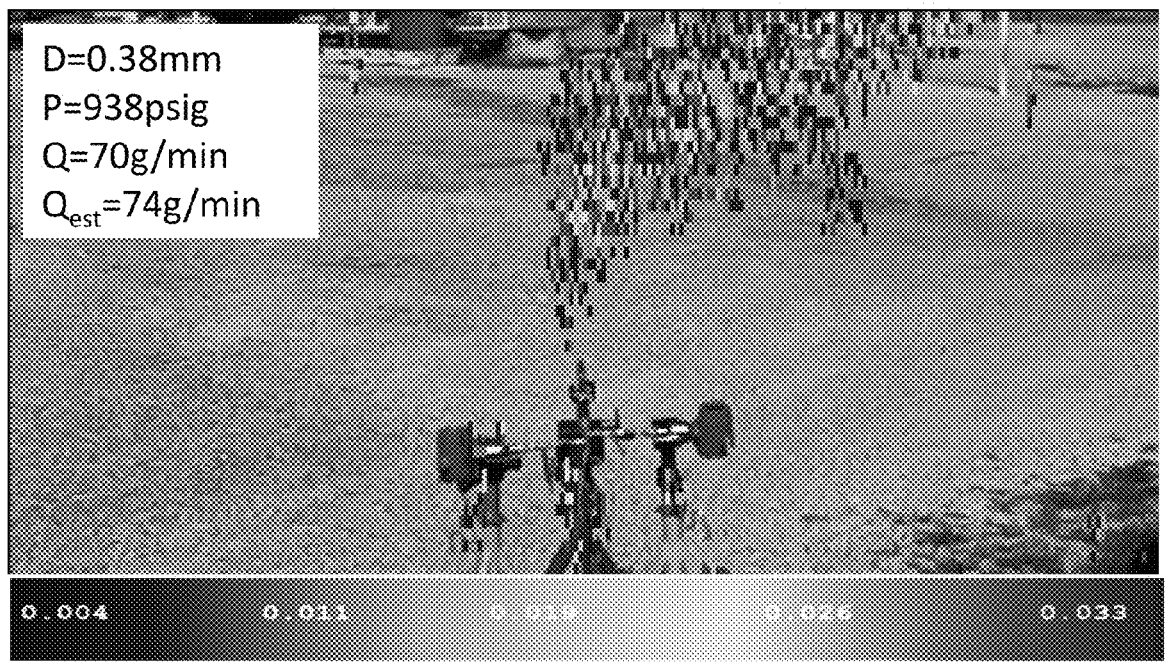
FIG. 21A is an example gas absorption image for a field test of 1000% methane exiting a 0.38 mm round orifice at an exit pressure of 938 psig in wind, according to an illustrative embodiment.

FIG. 21A is an example gas absorption image 2100 of approximately 100% methane exiting from a 0.38 mm round orifice at an exit pressures of 938 psig in wind. Experiments were conducted outdoors in natural sunlight under varying crosswinds. The instrumented mass inflow was measured as 70 grams/minute of methane. The mass flux emitted from the orifice as estimated directly from the imagery using the invented methods is 74 grams/minute.

Figure 21B:
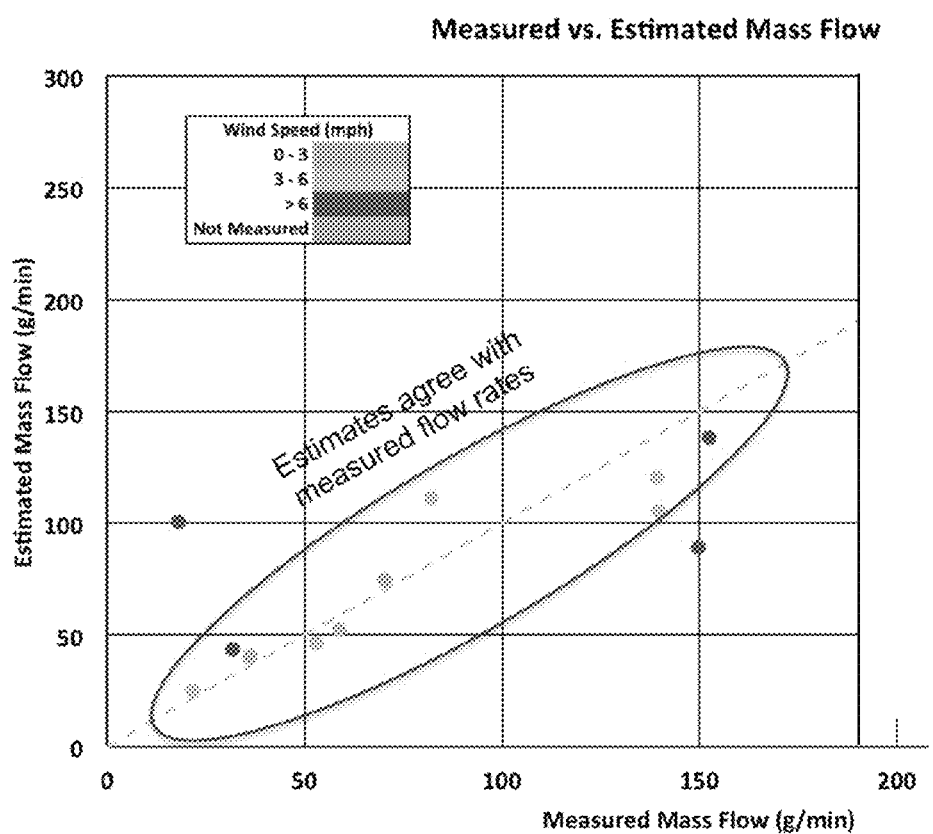
FIG. 21B is a graph comparing image-based estimates of methane mass outflow to instrumented measurements of methane mass inflow, for a set of experiments conducted with round-hole orifices at various exit pressures up to 1000 psig, in winds measured between 0-10 miles/hour, according to an illustrative embodiment.

FIG. 21B graphs the data obtained using the setup in FIG. 21A. Specifically, FIG. 21B compares imagery estimated methane mass outflow (i.e., emission flux) to instrumented measurements of mass inflow for a set of experiments conducted with round-hole orifices at various exit pressures, in winds measured between 0-10 miles per hour. Mass emission flux estimates are shown to agree well with instrumented inflow measurements as taken up to 150 grams/minute. Data is presented for winds of 0-3 mph, 3-6 mph, and >6 mph. This validates the method for estimating gas leak rate (i.e., emission flux) from absorption imagery, for holes in pressurized lines.

Figure 22A:
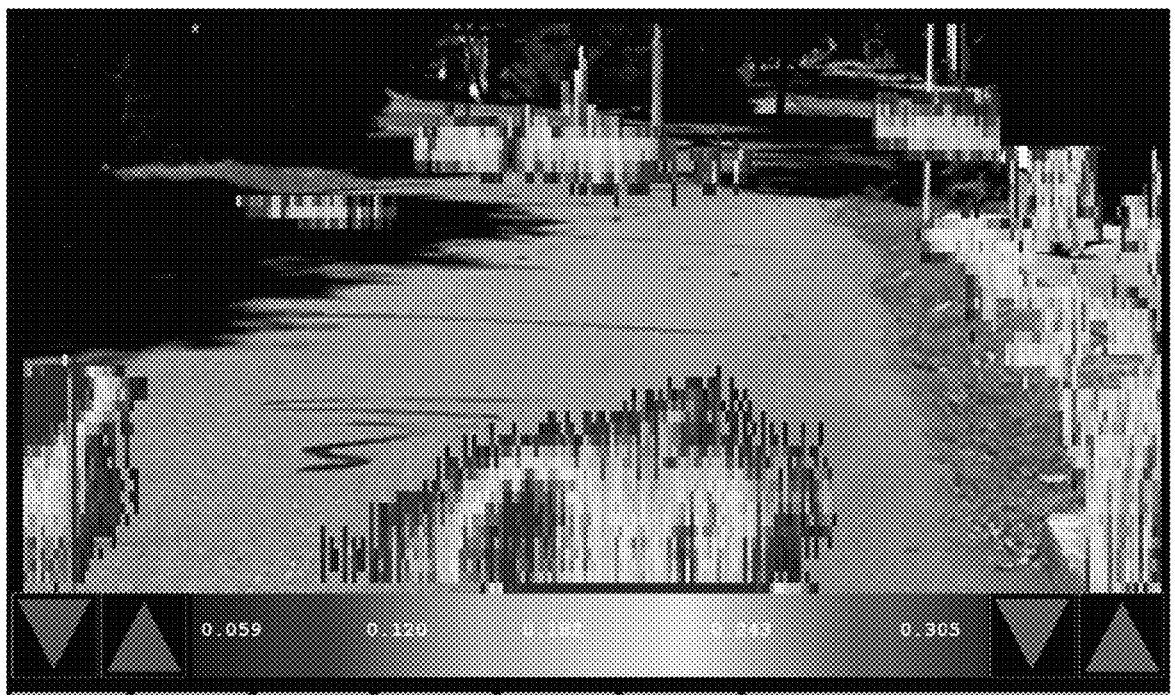
FIG. 22A is an example gas absorption image of a residential street in the Boston area, according to an illustrative embodiment.

An example gas image 2200 is shown in FIG. 22A, where natural gas is leaking from an underground pipe in municipal gas infrastructure in Boston, Mass. Gas emissions due to a leak in the underground pipeline are detected and overlaid on the background visible image. All detections as illustrated were confirmed using a flame ionization gas sensor to sample the air above each surface emission area. By the time the gas percolates up through the soil, it is approximately the same temperature as the ground itself. A sensor system such as presently disclosed can image the gas emissions from the surface in sunlight as shown, or alternatively using artificial illumination projected from an illuminator as described previously, or using a combination of sunlight and projected illumination, where the light reflects off the ground and is absorbed as it passes through the gas (possibly) twice. FIG. 22A illustrates the patchy nature of ground surface emissions, with gas emerging from manholes, storm gratings, cracks in road asphalt and concrete sidewalks, as well as along the side of the road where the asphalt meets dirt and grass. All of these surface emissions may be due to a single leak in a pipe at the bottom of the hill near the end of the street. The spatial distribution of surface leak patches can be useful in bounding the actual leak location in the underground pipe.

Figure 22B:
FIG. 22B is an example absorption image of natural gas leaking from a small pipe at 4 feet below the surface of a field, according to an illustrative embodiment.

FIG. 22B is an example absorption image 2250 of natural gas leaking from a small pipe at 4 feet below the surface of a field. The pipe is fed by the Montreal municipal gas network pressurized to 60 psig. The location of maximum surface emission is clear from the color overlay of gas absorption, and was confirmed using a gas sniffer.

Figure 23A:
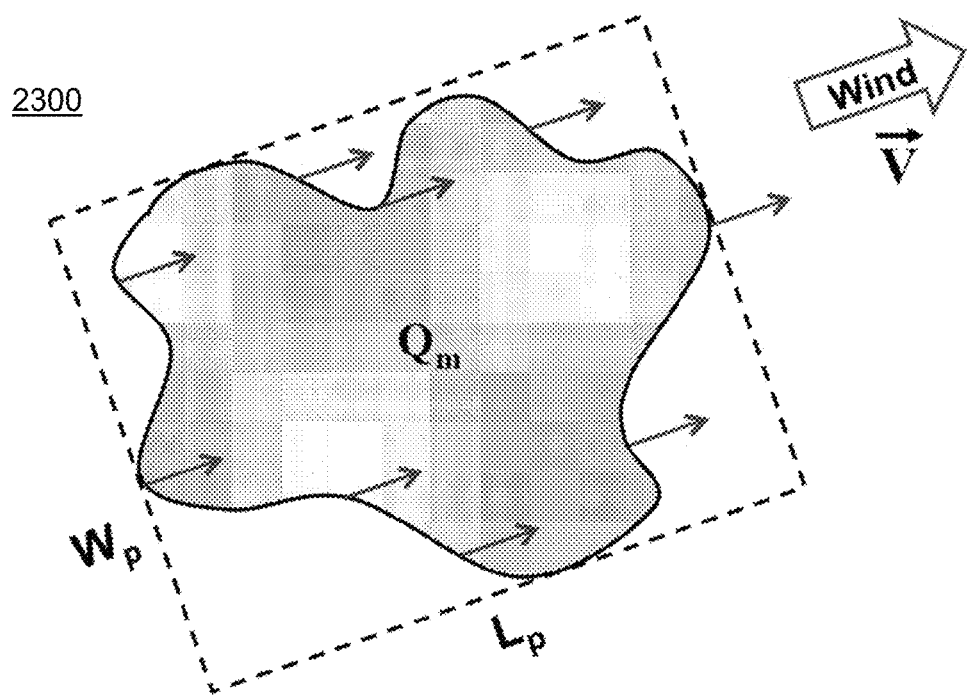
FIG. 23A is a plan view of a surface patch emitting methane (or natural gas) at rate Qm grams/sec on average within its irregular boundary with ground-level winds of speed V, according to an illustrative embodiment.

A plan view of a surface patch emitting methane (or natural gas) at rate Qm grams/sec on average within an irregular boundary is shown in diagram 2300 of FIG. 23A. Ground-level winds, of speed V in the direction shown, determine the orientation of the bounding rectangle of dimensions Lp along the wind direction and Wp across the wind direction. In steady winds, the emission flux up from the ground balances the flux of methane flowing across the downwind boundary.

Figure 23B:
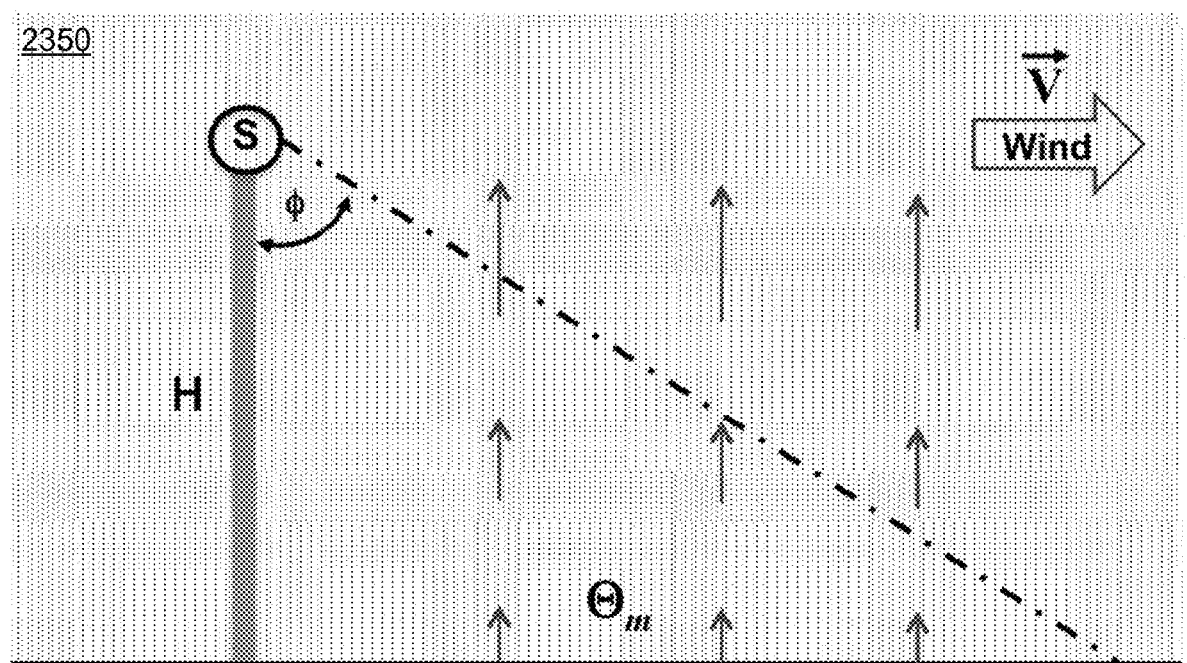
FIG. 23B is a side view of the sensor S mounted atop a mast on the ground within a wide-area surface emission site, according to an illustrative embodiment.

FIG. 23B is a diagram 2350 of a side view of the sensor S mounted atop a mast (with height H) on the ground within a wide-area surface emission site. The methane flux (per unit area) out of the ground establishes a stratified methane atmosphere above the ground, wherein this emission flux balances the buoyancy driven upward flow of methane.

Next, the mathematical formulation of absorption imaging and quantification of gas leaks is described, using methane or natural gas as a specific example.

ii. Example Spectral Filters for Defining the SWIR Spectral Bands

Figure 24A:
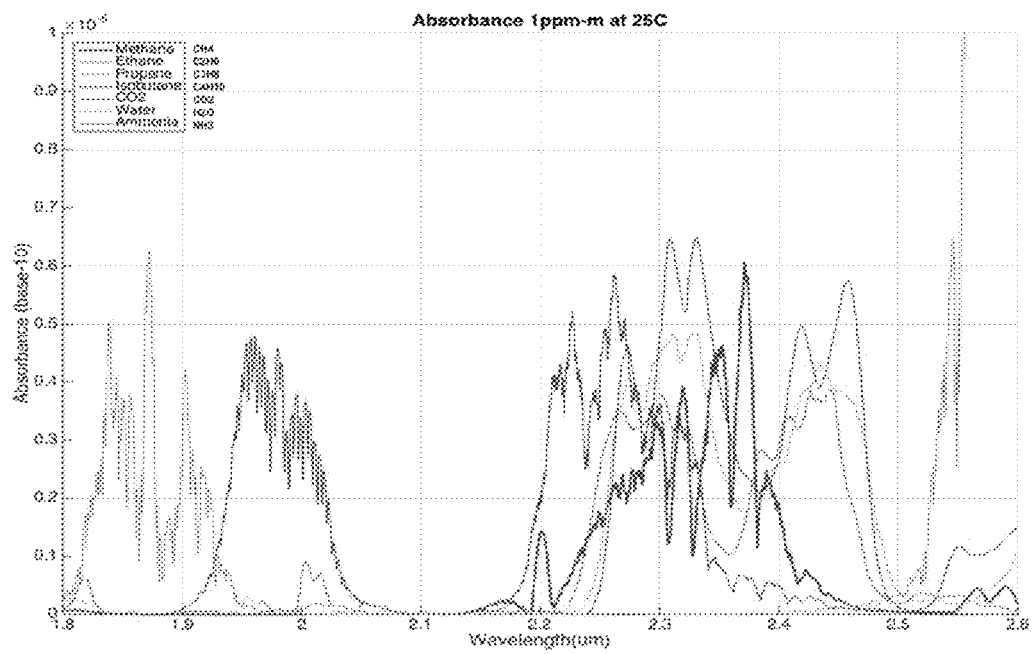
FIG. 24A is the absorption spectra in the 1.8-2.6 micron range of the short-wave infrared for the gases methane, ethane, propane, butane, carbon dioxide, ammonia, and water vapor, according to an illustrative embodiment.
Figure 24B:
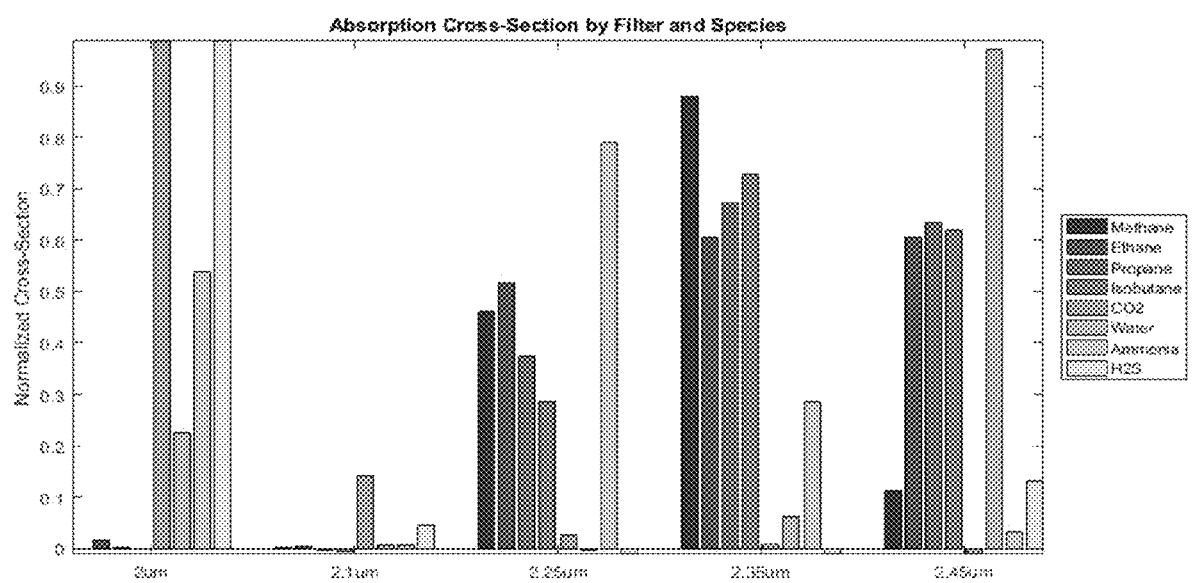
FIG. 24B is the normalized 5-band spectra for the same gases as in FIG. 24A, where the ideal spectral bands have bandwidths of 100 nanometers, and band centers at wavelengths of 2000, 2100, 2250, 2350, and 2450 nanometers, according to an illustrative embodiment.

In certain embodiments, spectral data is collected through multiple filters, each of bandwidth approximately 100 nanometers (nm) with transmission greater than 5%, spanning the wavelength region approximately 1950-2500 nanometers (i.e., 1.95-2.50 microns). This data provides coverage of spectral features (e.g., groups of spectral lines) that characterize methane, ethane, propane, butane, carbon dioxide, ammonia, and possibly other gases of interest, yet avoids the strong water vapor absorption features, as illustrated in FIG. 24A. The data is organized into multiple spectral bands, for example five bands as illustrated in FIG. 24B. The data itself is collected in real-time by the SWIR sensor as it points in directions in space that correspond to locations on the ground, or objects on the site, being monitored by the scanning SWIR sensor. One of the multiple spectral bands is selected to include only weak or no features of the gases of interest, and is referred to as the "reference band." as exemplified by the 100 nm wide band centered near 2100 nm in FIG. 24B. Refer to this spectral band filter as the Reference Filter with transmission $F_{ref}(\lambda)$ and integrated transmission $F_{ref}$. The other spectral band filters are simply referred to as Spectral Filter B (where B is the band number), each with transmission $F_B(\lambda)$, and integrated transmission $F_B$.

Data collected at each spectral band will be corrected for the integrated transmission associated with its corresponding spectral filter $F_B$, to form $I_B$ the intensity in band B. The intensity of each band is then measured relative to $I_{ref}$ the data collected at the reference band corrected by the transmission of the reference filter $F_{ref}$. The resulting transmission corrected data are a set of spectral band ratios forming a spectral pattern $P_S$ (a vector) defined as:

$$P_S = \text{Set of Band Ratios}\{I_B/I_{ref}\} \quad \text{(Eq. 1)}$$

Each gas of interest is characterized by its own spectral pattern of band ratios, and will be detected in the measured data by spectral pattern recognition methods, including spectral pattern unmixing in the case of gas mixtures. It can be shown that the 5-element spectral patterns associated with the gases shown in FIG. 24B enable separation of the gases of interest, including mixtures that characterize natural gas from geographically different locations and from processed distribution gas. Separation of pure methane from distribution gas is the most challenging, as distribution gas is typically 95% methane. The selection of spectral bands can be tailored to speciate and not confuse a desired set of gases and mixtures, or group together numerous gases (e.g., light hydrocarbons) to be recognized as a gas within the group.

iii. Examples of Adapting Sensor to Ambient Environment

The optical depths in each spectral band B and the reference band, as measured in the ambient environment, are denoted herein as $\tau_B^{(\alpha)}$ and $\tau_{ref}^{(\alpha)}$, in certain embodiments. These optical depths are the products of the absorptivity and r, the path length through the environment. The band intensities resulting from the radiative transfer are:

$$I_B^{(\alpha)} = S_B(r) Q_B F_B R_B \exp\text{-}[\tau_B^{(\alpha)}] \quad \text{(Eq. 2a)}$$

$$I_{ref}^{(\alpha)} = S_{ref}(r) Q_{ref} F_{ref} R_{ref} \exp\text{-}[\tau_{ref}^{(\alpha)}] \quad \text{(Eq. 2b)}$$

Here. $S_B$ is the illumination source function (combining both solar and artificial illumination), $Q_B$ is the quantum efficiency of the detector, $F_B$ is the integrated transmission of the filter, and $R_B$ is the reflectance of the background material (which can be a calibration panel or the natural surrounding materials), all corresponding to spectral band B and similarly for the reference band.

Form the pattern $P_B$ of spectral band ratios, and note the spectral illumination source function ratio $S_B/S_{ref}$ is independent of path length r and only a function of wavelength.

The cross-channel gain is $G_B$. The ambient spectral differential absorption coefficient is $\delta\alpha_B^{(\alpha)}$, and the path length from sensor to a reflector panel is $L_R$. Eq. 2a and Eq. 2b may be combined to obtain:

$$\frac{I_B^{(\alpha)}}{I_{ref}^{(\alpha)}} = \frac{[S_B(0)Q_B F_B R_B]}{[S_{ref}(0)Q_{ref} F_{ref} R_{ref}]} \exp\text{-}[\tau_B^{(\alpha)} - \tau_{ref}^{(\alpha)}] \quad \text{(Eq. 3a)}$$

$$\frac{I_B^{(\alpha)}}{I_{ref}^{(\alpha)}} = G_B \exp\text{-} 2L_R[\alpha_B^{(\alpha)} - \alpha_{ref}^{(\alpha)}] = G_B \exp\text{-} 2L_R[\delta\alpha_B^{(\alpha)}] \quad \text{(Eq. 3b)}$$

The factor $$\frac{[S_B(0)Q_B F_B R_B]}{[S_{ref}(0)Q_{ref} F_{ref} R_{ref}]}$$

of Eq. 3a corresponds to $G_B$ of Eq. 3b, and $[\tau_B^{(\alpha)} - \tau_{ref}^{(\alpha)}]$ of Eq. 3a corresponds to $2L_R[\delta\alpha_B^{(\alpha)}]$ of Eq. 3b.

The SWIR illumination reflecting from a calibration reflector panel (an example of which is Spectralon) is measured in each spectral band B at two distances, the spot or image average intensities are calculated, and the log of their ratio is formed to solve for the unknowns $G_B$ and $\delta\alpha_B^{(\alpha)}$. In certain embodiments, more than two distances are used, and these unknown quantities are obtained using least squares analysis.

Each gain $G_B$, as defined in Eq. 3b, incorporates the ratios of filter band transmissions, detector quantum efficiencies, and band reflectivities of the calibration panel. Each gain $G_B$ is rescaled (utilizing in-scene background reflectors) by the ratio of in-scene band reflectivities. $\delta\alpha_B^{(\alpha)}$ and spectral samples of the in-scene background materials (e.g., cement, asphalt, dirt, grass, etc.) are used to determine the rescaled gain $G_B$ for each reflecting material. In certain embodiments, it is desired, but not essential, that the sensor automatically recognize the background materials that comprise a site being inspected or monitored.

iv. Examples of Detecting and Imaging Gas Leaks

In an illustrative embodiment, a system samples or images in the direction of a possible gas leak of extent $D_J$ (e.g., jet width) and measures/senses the range $L_R$ to the reflecting surface in the background (e.g., with either the reflector panel or in-scene material serving as a reflector). $\tau_B^{(g+\alpha)}$ is the band-B optical depth of the combined possible gas jet in the ambient environment from the sensor to the reflector at $L_R$ and back to the sensor. Thus, the intensities in the bands (including reference band) are:

$$I_B^{(g)} = S_B(r) Q_B F_B R_B \exp\text{-}[\tau_B^{(g+\alpha)}] \quad \text{(Eq. 4a)}$$

$$I_{ref}^{(g)} = S_{ref}(r) Q_{ref} F_{ref} R_{ref} \exp\text{-}[\tau_{ref}^{(g+\alpha)}] \quad \text{(Eq. 4b)}$$

Form each ratio of spectral band intensities, the expression for the cross-channel gain (rescaled for background surface reflector), may be substituted to define the differential spectral absorption coefficient of gas ($\delta\alpha_B^{(\alpha)}$), and terms may be rearranged to obtain:

$$\frac{I_B^{(g)}}{I_{ref}^{(g)}} = G_B \exp\text{-}\{2D_J[\delta\alpha_B^{(g)} - \delta\alpha_{ref}^{(\alpha)}] + 2L_R[\delta\alpha_B^{(\alpha)}]\} \quad \text{(Eq. 5)}$$

The Excess Differential Spectral Absorptivity of the gas leak (for example, diluted natural gas) over that of the ambient atmosphere environment is then given by:

$$\Delta_B^{(g-\alpha)} \equiv \delta\alpha_B^{(g)} - \delta\alpha_B^{(\alpha)} = [\alpha_B^{(g)} - \alpha_{ref}^{(g)}] - [\alpha_B^{(\alpha)} - \alpha_{ref}^{(\alpha)}] \quad \text{(Eq. 6)}$$

The Differential Spectral Optical Depth image due to the gas leak is thus obtained from the measured spectral intensities and calibration parameters:

$$\delta OD_B = [\Delta_B^{(g-\alpha)}]D_J = -\frac{1}{2}\ln\left[\frac{1}{G_B}\frac{I_B^{(g)}}{I_{ref}^{(g)}}\right] - [\delta\alpha_B^{(\alpha)}]L_R \quad \text{(Eq. 7a)}$$

In the case of negligible atmospheric absorption over range 2r compared to the gas leak itself, the 2nd term on the right can be neglected, yielding:

$$\delta OD_B = -\frac{1}{2}\ln\left[\frac{1}{G_B}\frac{I_B^{(g)}}{I_{ref}^{(g)}}\right] \quad \text{(Eq. 7b)}$$

The factor of ½ comes from the (possible) double path length through the gas due to reflection of incident light off the background at range r. In the case of single pass transmission (e.g., sunlight through the gas), this factor is dropped.

D. Network and Computer Implementation

Figure 25:
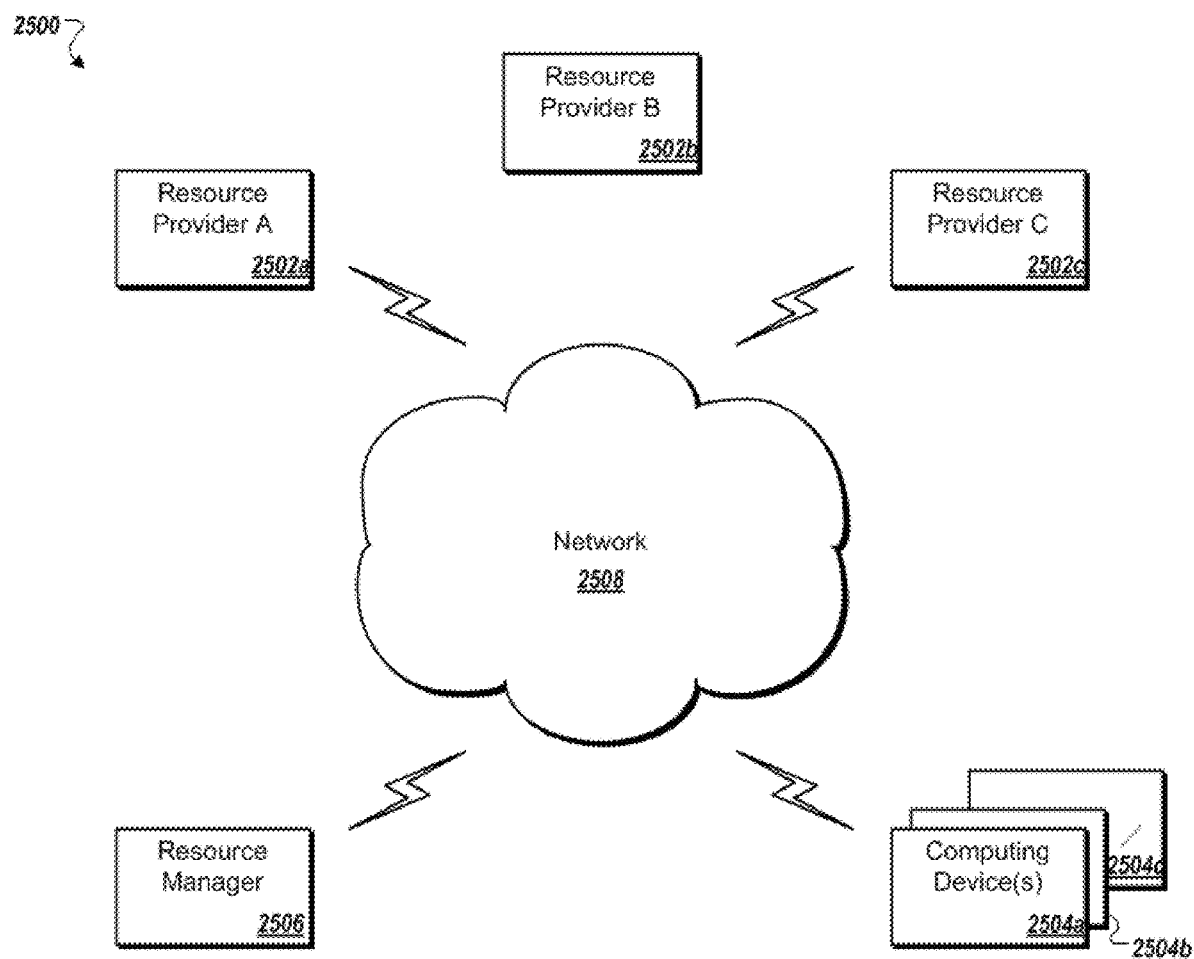
FIG. 25 is a block diagram of an example network environment for use in the methods and systems described herein, according to an illustrative embodiment.

As shown in FIG. 25, an implementation of a network environment 2500 for use in the systems, methods, and architectures described herein for obtaining a multispectral absorption image of a scene, is shown and described. In brief overview, referring now to FIG. 25, a block diagram of an exemplary cloud computing environment 2500 is shown and described. The cloud computing environment 2500 may include one or more resource providers 2502a. 2502b, 2502c (collectively, 2502). Each resource provider 2502 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 2502 may be connected to any other resource provider 2502 in the cloud computing environment 2500. In some implementations, the resource providers 2502 may be connected over a computer network 2508. Each resource provider 2502 may be connected to one or more computing device 2504a, 2504b, 2504c (collectively, 2504), over the computer network 2508. The cloud computing environment 2500 may include a resource manager 2506. The resource manager 2506 may be connected to the resource providers 2502 and the computing devices 2504 over the computer network 2508. In some implementations, the resource manager 2506 may facilitate the provision of computing resources by one or more resource providers 2502 to one or more computing devices 2504. The resource manager 2506 may receive a request for a computing resource from a particular computing device 2504. The resource manager 2506 may identify one or more resource providers 2502 capable of providing the computing resource requested by the computing device 2504. The resource manager 2506 may select a resource provider 2502 to provide the computing resource. The resource manager 2506 may facilitate a connection between the resource provider 2502 and a particular computing device 2504. In some implementations, the resource manager 2506 may establish a connection between a particular resource provider 2502 and a particular computing device 2504. In some implementations, the resource manager 2506 may redirect a particular computing device 2504 to a particular resource provider 2502 with the requested computing resource.

Figure 26:
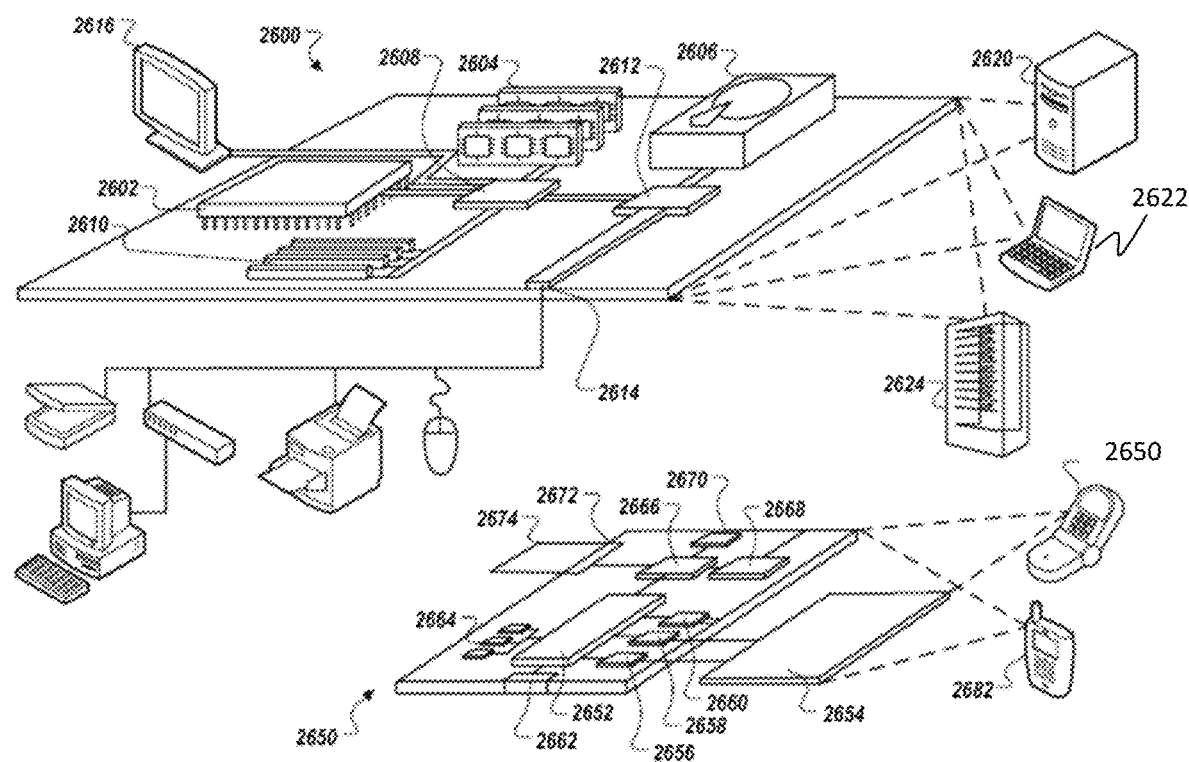
FIG. 26 is a block diagram of an example computing device and an example mobile computing device, for use in illustrative embodiments of the invention.

FIG. 26 shows an example of a computing device 2600 and a mobile computing device 2650 that can be used in the methods and systems described in the present disclosure. The computing device 2600 is intended to represent various forms of digital computers, such as industrial single board computers, laptops, desktops, workstations, personal digital assistants, servers, blade servers, mainframes, and other appropriate computers. The mobile computing device 2650 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 2600 includes a processor 2602, a memory 2604, a storage device 2606, a high-speed interface 2608 connecting to the memory 2604 and multiple high-speed expansion ports 2610, and a low-speed interface 2612 connecting to a low-speed expansion port 2614 and the storage device 2606. Each of the processor 2602, the memory 2604, the storage device 2606, the high-speed interface 2608, the high-speed expansion ports 2610, and the low-speed interface 2612, are interconnected using various busses, and may be mounted on a common motherboard or in other manners as appropriate. The processor 2602 can process instructions for execution within the computing device 2600, including instructions stored in the memory 2604 or on the storage device 2606 to display graphical information for a GUI on an external input/output device, such as a display 2616 coupled to the high-speed interface 2608. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number (one or more) of processors of any number (one or more) of computing devices (e.g., in a distributed computing system, e.g., associated with a virtual computing system, e.g., of a cloud-based computing system).

The memory 2604 stores information within the computing device 2600. In some implementations, the memory 2604 is a volatile memory unit or units. In some implementations, the memory 2604 is a non-volatile memory unit or units. The memory 2604 may also be another form of computer-readable medium, such as a magnetic or optical disk.

The storage device 2606 is capable of providing mass storage for the computing device 2600. In some implementations, the storage device 2606 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 2602), perform one or more methods, such as those described above. The instructions can also be stored by one or more storage devices such as computer- or machine-readable mediums (for example, the memory 2604, the storage device 2606, or memory on the processor 2602).

The high-speed interface 2608 manages bandwidth-intensive operations for the computing device 2600, while the low-speed interface 2612 manages lower bandwidth-intensive operations. Such allocation of functions is an example only. In some implementations, the high-speed interface 2608 is coupled to the memory 2604, the display 2616 (e.g., through a graphics processor or accelerator), and to the high-speed expansion ports 2610, which may accept various expansion cards (not shown). In the implementation, the low-speed interface 2612 is coupled to the storage device 2606 and the low-speed expansion port 2614. The low-speed expansion port 2614, which may include various communication ports (e.g., USB, Bluetooth®, Ethernet wireless Ethernet) may be coupled to one or more input/output devices, such as a keyboard, a pointing device, a scanner, or a networking device such as a switch or router, e.g., through a network adapter.

The computing device 2600 may be implemented in a number of different forms, as shown in the figure. For example, it may be implemented as a standard server 2620, or multiple times in a group of such servers. In addition, it may be implemented in a personal computer such as a laptop computer 2622. It may also be implemented as part of a rack server system 2624. Alternatively, components from the computing device 2600 may be combined with other components in a mobile device (not shown), such as a mobile computing device 2650. Each of such devices may contain one or more of the computing device 2600 and the mobile computing device 2650, and an entire system may be made up of multiple computing devices communicating with each other.

The mobile computing device 2650 includes a processor 2652, a memory 2664, an input/output device such as a display 2654, a communication interface 2666, and a transceiver 2668, among other components. The mobile computing device 2650 may also be provided with a storage device, such as a micro-drive or other device, to provide additional storage. Each of the processor 2652, the memory 2664, the display 2654, the communication interface 2666, and the transceiver 2668, are interconnected using various buses, and several of the components may be mounted on a common motherboard or in other manners as appropriate.

The processor 2652 can execute instructions within the mobile computing device 2650, including instructions stored in the memory 2664. The processor 2652 may be implemented as a chipset of chips that include separate and multiple analog and digital processors. The processor 2652 may provide, for example, for coordination of the other components of the mobile computing device 2650, such as control of user interfaces, applications run by the mobile computing device 2650, and wireless communication by the mobile computing device 2650.

The processor 2652 may communicate with a user through a control interface 2658 and a display interface 2656 coupled to the display 2654. The display 2654 may be, for example, a TFT (Thin-Film-Transistor Liquid Crystal Display) display or an OLED (Organic Light Emitting Diode) display, or other appropriate display technology. The display interface 2656 may comprise appropriate circuitry for driving the display 2654 to present graphical and other information to a user. The control interface 2658 may receive commands from a user and convert them for submission to the processor 2652. In addition, an external interface 2662 may provide communication with the processor 2652, so as to enable near area communication of the mobile computing device 2650 with other devices. The external interface 2662 may provide, for example, for wired communication in some implementations, or for wireless communication in other implementations, and multiple interfaces may also be used.

The memory 2664 stores information within the mobile computing device 2650. The memory 2664 can be implemented as one or more of a computer-readable medium or media, a volatile memory unit or units, or a non-volatile memory unit or units. An expansion memory 2674 may also be provided and connected to the mobile computing device 2650 through an expansion interface 2672, which may include, for example, a SIMM (Single In Line Memory Module) card interface or a DIMM (Double In Line Memory Module) card interface. The expansion memory 2674 may provide extra storage space for the mobile computing device 2650, or may also store applications or other information for the mobile computing device 2650. Specifically, the expansion memory 2674 may include instructions to carry out or supplement the processes described above, and may include secure information also. Thus, for example, the expansion memory 2674 may be provided as a security module for the mobile computing device 2650, and may be programmed with instructions that permit secure use of the mobile computing device 2650. In addition, secure applications may be provided via the DIMM cards, along with additional information, such as placing identifying information on the DIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 2652), perform one or more methods, such as those described above. The instructions can also be stored by one or more storage devices, such as one or more computer- or machine-readable mediums (for example, the memory 2664, the expansion memory 2674, or memory on the processor 2652). In some implementations, the instructions can be received in a propagated signal, for example, over the transceiver 2668 or the external interface 2662.

The mobile computing device 2650 may communicate wirelessly through the communication interface 2666, which may include digital signal processing circuitry where necessary. The communication interface 2666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 2668 using a radio-frequency. In addition, short-range communication may occur, such as using a Bluetooth®, Wi-Fi™, or other such transceiver (not shown). In addition, a GPS (Global Positioning System) receiver module 2670 may provide additional navigation- and location-related wireless data to the mobile computing device 2650, which may be used as appropriate by applications running on the mobile computing device 2650.

The mobile computing device 2650 may also communicate audibly using an audio codec 2660, which may receive spoken information from a user and convert it to usable digital information. The audio codec 2660 may likewise generate audible sound for a user, such as through a speaker, e.g., in a handset of the mobile computing device 2650. Such sound may include sound from voice telephone calls, may include recorded sound (e.g., voice messages, music files, etc.) and may also include sound generated by applications operating on the mobile computing device 2650.

The mobile computing device 2650 may be implemented in a number of different forms, as shown in the figure. For example, it may be implemented as a cellular telephone 2680. It may also be implemented as part of a smart-phone 2682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A system for obtaining a multispectral absorption image of a scene using a structured illumination beam that is scanned in a synchronized fashion with an instantaneous field of view (ifov) of an optical sensor, the system comprising:
   (a) an illumination source aligned and operable to produce the structured illumination beam and direct the structured illumination beam towards a target surface within the scene, thereby illuminating an illumination spot corresponding to a projection of the structured illumination beam onto the target surface, the illumination spot having a length and a width, wherein the length is greater than or equal to the width;
   (b) a beam scanner operable to scan the illumination spot in a beam scan direction that is substantially parallel to the width of the illumination spot;
   (c) an optical sensor comprising one or more spectral detectors, each aligned and operable to detect light having wavelengths within a particular associated spectral band, wherein the optical sensor is aligned and operable to capture light from the scene within a sensor instantaneous field of view (ifov) corresponding to a combined ifov of the one or more spectral detectors and direct the captured light, for detection, onto the one or more spectral detectors, thereby detecting light from a particular sampled image location corresponding to a projection of the sensor ifov onto the target surface;
   (d) an optical sensor scanner aligned and operable to scan the projection of the sensor ifov across the scene, so as to detect light from a plurality of sampled image locations within the scene, wherein the optical sensor scanner is synchronized with the beam scanner so as to maintain overlap between the projection of the sensor ifov and the illumination spot as both are scanned;
   (e) a processor of a computing device; and
   (f) a memory having instructions stored thereon, wherein the instructions, when executed by the processor, cause the processor to:
      retrieve and/or access data corresponding to the detected light from each of the sampled image locations; and
      use the data to create a multispectral absorption image of the scene,
   wherein the structured beam of illumination comprises short wave infrared (SWIR) light, and the one or more spectral detectors are responsive to SWIR light.

2. The system of claim 1, wherein the structured illumination beam is structured spatially to compensate for dilution of projected power with range.

3. The system of claim 2, wherein the illumination source comprises a plurality of emitters each of which outputs illumination light, wherein the illumination light output from the plurality of emitters is combined to produce the structured beam of illumination.

4. The system of claim 1, wherein the multispectral absorption image comprises a plurality of image pixels, each (i) corresponding to a particular physical location within the scene and (ii) having one or more intensity values each representing a level of absorption within a corresponding particular spectral band and determined using the data corresponding to the detected light from each of the sampled image locations.

5. The system of claim 4, wherein for each of at least a portion of the intensity values, the corresponding particular spectral band comprises a plurality of absorption lines of a specific compound of interest.

6. The system of claim 5, wherein the particular spectral band is an extended spectral band, spanning approximately 50 nanometers or more.

7. The system of claim 4, wherein the optical sensor comprises at least one spectral filter positioned in front of at least a portion of the one or more spectral detectors, wherein the at least one spectral filter is substantially transmissive to light having a wavelength within a specific spectral band of the corresponding particular spectral band(s) and substantially opaque to light having a wavelength outside of the specific spectral band.

8. The system of claim 1, wherein the structured beam of illumination comprising SWIR light provides illumination that spans a spectral range of approximately 1000 to 2500 nanometers.

9. The system of claim 1, wherein the illumination source produces illumination characteristic of a blackbody radiator at a temperature of approximately 1200° C.

10. A method of obtaining a multispectral absorption image of a scene using a structured illumination beam that is scanned in a synchronized fashion with an instantaneous field of view (ifov) of an optical sensor, the method comprising:
(a) directing the structured illumination beam from an illumination source towards a target surface within the scene, thereby illuminating an illumination spot corresponding to a projection of the structured illumination beam onto the target surface, wherein the illumination spot has a length and a width, wherein the length is greater than or equal to the width;
(b) scanning the illumination spot in a beam scan direction that is substantially along its width;
(c) detecting, with one or more spectral detectors of an optical sensor, light from the scene and captured within the ifov of the optical sensor, thereby detecting light from a particular sampled image location corresponding to a projection of the sensor ifov onto the target surface;
(d) scanning the projection of the sensor ifov across the scene, so as to detect light from a plurality of sampled image locations within the scene, wherein the optical sensor scanner is synchronized with the beam scanner and so as to maintain overlap between the projection of the sensor ifov and the illumination spot as both are scanned;
(e) retrieving and/or accessing, by a processor of a computing device, data corresponding to the detected light for each of the sampled image locations; and
(f) creating, by the processor, using the data, a multispectral absorption image of the scene,
wherein the structured beam of illumination comprises short wave infrared (SWIR) light, and the one or more spectral detectors are responsive to SWIR light.

11. The method of claim 10, wherein the structured illumination beam is structured spatially to compensate for dilution of projected power with range.

12. The method of claim 11, wherein the illumination source comprises a plurality of emitters each of which outputs illumination light, wherein the illumination light output from the plurality of emitters is combined to produce the structured beam of illumination.

13. The method of claim 10, wherein the multispectral absorption image comprises a plurality of image pixels, each (i) corresponding to a particular physical location within the scene and (ii) having one or more intensity values each representing a level of absorption within a corresponding particular spectral band and determined using the data corresponding to the detected light from each of the sampled image locations.

14. The method of claim 13, wherein for each of at least a portion of the intensity values, the corresponding particular spectral band comprises a plurality of absorption lines of a specific compound of interest.

15. The system of claim 14, wherein the particular spectral band is an extended spectral band, spanning approximately 50 nanometers or more.

16. The method of claim 13, wherein the optical sensor comprises at least one spectral filter positioned in front of at least a portion of the one or more spectral detectors, wherein the at least one spectral filter is substantially transmissive to light having a wavelength within a specific spectral band of the corresponding particular spectral band(s) and substantially opaque to light having a wavelength outside of the specific spectral band.

17. The system of claim 10, wherein the structured beam of illumination comprising SWIR light provides illumination that spans a spectral range of approximately 1000 to 2500 nanometers.

18. The system of claim 10, wherein the illumination source produces illumination characteristic of a blackbody radiator at a temperature of approximately 1200° C.

19. A system for obtaining a multispectral absorption image of a scene using a structured illumination beam that is scanned in a synchronized fashion with an instantaneous field of view (ifov) of an optical sensor, the system comprising:
(a) an illumination source aligned and operable to produce the structured illumination beam and direct the structured illumination beam towards a target surface within the scene, thereby illuminating an illumination spot corresponding to a projection of the structured illumination beam onto the target surface, the illumination spot having a length and a width, wherein the length is greater than or equal to the width, and wherein the structured illumination beam is structured spatially to compensate for dilution of projected power with range;
(b) a beam scanner operable to scan the illumination spot in a beam scan direction that is substantially parallel to the width of the illumination spot;
(c) an optical sensor comprising one or more spectral detectors, each aligned and operable to detect light having wavelengths within a particular associated spectral band, wherein the optical sensor is aligned and operable to capture light from the scene within a sensor instantaneous field of view (ifov) corresponding to a combined ifov of the one or more spectral detectors and direct the captured light, for detection, onto the one or more spectral detectors, thereby detecting light from a particular sampled image location corresponding to a projection of the sensor ifov onto the target surface;
(d) an optical sensor scanner aligned and operable to scan the projection of the sensor ifov across the scene, so as to detect light from a plurality of sampled image locations within the scene, wherein the optical sensor scanner is synchronized with the beam scanner so as to maintain overlap between the projection of the sensor ifov and the illumination spot as both are scanned;
(e) a processor of a computing device; and
(f) a memory having instructions stored thereon, wherein the instructions, when executed by the processor, cause the processor to:

retrieve and/or access data corresponding to the detected light from each of the sampled image locations; and use the data to create a multispectral absorption image of the scene.

20. The system of claim 19, wherein the illumination source comprises a plurality of emitters each of which outputs illumination light, wherein the illumination light output from the plurality of emitters is combined to produce the structured beam of illumination.

21. The system of claim 19, wherein the structured beam of illumination comprising SWIR light provides illumination that spans a spectral range of approximately 1000 to 2500 nanometers.

22. The system of claim 19, wherein the illumination source produces illumination characteristic of a blackbody radiator at a temperature of approximately 1200° C.

* * * * *